United States Patent [19]
Glick

[11] Patent Number: 6,080,588
[45] Date of Patent: Jun. 27, 2000

[54] THERAPEUTIC METHODS FOR BENZODIAZEPINE DERIVATIVES

[75] Inventor: Gary D. Glick, Ann Arbor, Mich.

[73] Assignee: The Regents of the University of Michigan, Ann Arbor, Mich.

[21] Appl. No.: 08/881,037

[22] Filed: Jun. 23, 1997

Related U.S. Application Data

[62] Division of application No. 08/443,540, May 18, 1995, abandoned.

[51] Int. Cl.$^7$ .................................................. G01N 33/564
[52] U.S. Cl. ........................ 436/508; 436/506; 424/140.1; 424/184.1
[58] Field of Search ................................... 436/506, 508; 424/140.1, 184.1, 810; 435/7.1

[56] References Cited

U.S. PATENT DOCUMENTS

| | | |
|---|---|---|
| 4,690,905 | 9/1987 | Diamond . |
| 5,225,326 | 7/1993 | Bresser et al. . |

OTHER PUBLICATIONS

Andrzejewski, C., Jr., et al., "Antigen–Binding diversity and idiotypic cross–reactions among hybridoma autoantibodies to DNA" (1981) *J. Immunol.* 126(1):226–231. (Abstract only).

Ballard, D., et al., "Base specificity and idiotypy of anti–DNA Autoantibodies reactive with synthetic nucleic acids" (1985) *J. Immunol.* 135(5):3372–3380.

Ben–Chetrit, E., et al., "Specific inhibition of the DNA anti–DNA immune reaction by low molecular weight anionic compounds" (1988) *Immunology* 65:479–485.

Brinkman, K., et al., "Anti–DNA antibodies and lupus nephritis: The complexity of cross–reactivity" (1990) *Immunology Today* 11:232–234.

Campbell, "Monoclonal Antibody Technology" in *Laboratory Techniques in Biochemistry and Molecular Biology*, Burdon et al., Eds., New York, Elsevier (1984) vol. 13, pp. 168–169.

Chmielewski et al., "Monoclonal antibodies with sequence specific affinity for a stem–loop structure in DNA" (1991) *Tetrahedron* 47(14/15):2563–2572.

Edberg, J.C., et al., "Quantitative aspects of lupus anti–DNA autoantibody specificity" (1986) *J. Immunol.* 136:4581–4587.

Eilat, D., "Cross–reactions of anti–DNA and the central dogma of lupus nephritis" (1985) *Immunology Today* 6:123–127.

Eilat, D., "Monoclonal autoantibodies: An approach to studying autoimmune disease" (1982) *Mol. Immunol.* 19(7):943–955.

Eilat, D., et al., "Structure–function correlates of autoantibodies to nucleic acids: Lessons from immunochemical, genetic and structural studies" (1994) *Mol. Immunol.* 184:1377–1390.

Foster, M.H., et al., "Nephritogenic autoantibodies in systemic lupus erythematosus: Immunochemical properties, mechanisms of immune deposition, and genetic origins" (1993) *Lab. Invest.* 69:494–507.

Fukada et al., "Monoclonal anti–DNA antibody: Preparation and availability" *Nucl. Acids Res.* (1988) Symposium Series No. 19, pp. 69–72.

Glick, G.D., et al., "Trapping and isolation of an alternate DNA conformation" (1992) *J. Am. Chem. Soc.* 114:5447–5448.

Herron, J.N., et al., "An autoantibody to single–stranded DNA: Comparison of the three–dimensional structures of the unliganded Fab and a deoxynucleotide–Fab complex" (1991) *Proteins* 11:159–175.

Isenberg D.A., et al., "The origin, sequence, structure and consequences of developing anti–DNA antibodies: A human perspective" (1994) *Arthritis Rheum.* 37:169–180.

Koffler, D., et al., "Immunological studies concerning the nephritis of systemic lupus erythematosus" (1967) *J. Exp. Med.* 126:607–623.

Koffler, D., et al. "Antibodies to polynucleotides in human sera: antigenic specificity and relation to disease" (1971) *J. Exp. Med.* 134:294–312.

Lafer, E.M., et al., "Polyspecific monoclonal lupus autoantibodies reactive with both polynucleotides and phospholipids" (1981) *J. Exp. Med.* 153(4):897–909. (Abstract only).

Lee, J., et al., "Specificity of autoimmune monoclonal Fab fragments binding to single–stranded deoxyribonucleic acid" *Biochem.* (1982) 21:4940–4945.

Papalian, M., et al., "Reaction of systemic lupus erythematosus anti–native DNA antibodies with native DNA fragments from 20 to 1200 base pairs" (1980) *J. Clin. Invest.* 65:469–477.

Pisetsky, D., et al., "Binding specificity of a monoclonal anti–DNA antibody" (1982) *Mol. Immunol.* 19(5):645–650. (Abstract only).

Pollard, K., et al., "Polynucleotide specificities of murine monoclonal anti–DNA antibodies" (1986) *Clin. Immunol. Immunopathol.* 40(2):197–208. (Abstract only).

Radic, M.Z., et al., "Genetic and Structural evidence for antigen selection of anti–DNA antibodies" (1994) *Ann. Rev. Immunol.* 12:487–520.

(List continued on next page.)

*Primary Examiner*—Laurie Scheiner
*Attorney, Agent, or Firm*—Morrison & Foerster,LLP

[57] ABSTRACT

This invention provides an antibody with high affinity for single-stranded DNA, low or no affinity for double-stranded DNA, and capable of specifically binding a DNA hairpin and the hybridoma cell lines which produces these monoclonal antibodies. A chimeric mouse comprising these hybridoma cell lines and a histocompatible mouse is further provided. A method for screening for an agent which will inhibit anti-DNA antibody•DNA binding. One such agent is a benzodiazepine derivative. This invention therefore provides a method of inhibiting the binding of an anti-DNA antibody to its DNA ligand in a sample by contacting the sample with an effective amount of a benzodiazepine derivative.

3 Claims, 21 Drawing Sheets

OTHER PUBLICATIONS

Radic, M.Z., et al., "Residues that mediate DNA binding of autoimmune antibodies" (1993) *J. Immunol.* 150:4966–4977.

Rumbley, C.A., et al., "Construction, characterization, and selected site–specific mutagenesis of an anti–single–stranded DNA single–chain autoantibody" (1993) *J. Biol. Chem.* 268:13667–13674.

Stevens, S.Y., et al., "Application of the gel shift assay to study the affinity and specificity of anti–DNA antibodies" (1994) *J. Immunol. Methods* 177:185–190.

Stevens, S.Y., et al., "Evidence for induced fit in antibody–DNA complexes" (1993) *J. Am. Chem. Soc.* 115:1585–1586.

Stollar, D., et al., "The antigenic determinants of denatured DNA reactive with lupus erythematosus serum" (1962) *Proc. Natl. Acad. Sci. USA* 48:874–880.

Swanson et al., "Ligand recognition by murine anti–DNA autoantibodies II." *J. Clin. Invest.* (1996) 97(7):1748–1760.

Swanson, P.C., et al., "High resolution epitope mapping of an anti–DNA autoantibody using model DNA Ligands" (1994) *J. Immunol.* 152(5):2601–2612.

Tan, E.M., "Antinuclear antobodies: diagnostic markers for autoimmune diseases and probes for cell biology" (1989) *Adv. Immunol.* 44:93–151.

Termaat, J–H., et al., "Anti–DNA antibodies can bind to the glomerulus via two distinct mechanisms" (1992) *Kidney Intl.* 42:1363–1371.

Tetin, S.Y., et al., "Elucidation of anti ssDNA autoantibody BVO4–01 binding interactions with homooligonucleotides" (1993) *Biochemistry* 32:9011–9017.

Tsao, B.P., et al., "Structural characteristics of the variable regions of immunoglobulin genes encoding a pathogenic autoantibody in murine lupus" (1990) *J. Clin. Invest.* 85:530–540.

Voss, E.W. Jr., *Anti–DNA antibodies in SLE*. (1990) E.W. Voss, Jr., ed. Crc Press, Boca Raton, FL. A title page and table of contents were originally submitted.

Wang, H., et al., "Solution structure of a disulfide cross–linked DNA hairpin" (1994) *J. Am. Chem. Soc.* 116:5021–5022.

Watanabe–Fukunaga, R., et al., "Lymphoproliferation disorder in mice explained by defects in Fas antigen that mediates apoptosis" (1992) *Nature* 296:314–317.

Winter, G., et al., "Antibody–based therapy: Humanized antibodies" (1993) *TIPS* 14:139–143.

Oi et al., "Chimeric Antibodies" *BioTechniques* (1986) 4(3):214–221.

Ohnishi et al., "Comparison of pathogenic and non–pathogenic murine antibodies to DNA: antigen binding and structural characteristics" *International Immunology* (1994) 6(6):817–830.

CDR III                                                                           J Region
              270              280              290              300              310              320              330
        TGGGAGTTATTACTGT CAACATCATTATGGTACTCCATTCACG TTCGGGACGGGGACAAAATTGGAAATAAAA
15d8    ................  ............................  ..............................
9f11    ................  ............................  ..............................
15b10   ................  ............................  ..............................
5f3     ................  ............................  ..............................
4b2     ..CC.C.......... ..G..GTGGAG...TAC...CGG...       .TGGA..C..C..C..GC.............
10f4    G..AGT....T....C  TCT.AAG.ACACA.GT...TCCG...      .TGGA..C..C..C..GC.............
7b3     A.CA.CC.........  .TG.AA..A.A.AGGT..G.AT...       .AT....C..C..C..GC.............
8d8     ..CC.C..........  ..G..GTGGAG...TAC...CGG...      .TGGA..C..C..C..GC.............
11f8    ..CA.TG.....T...  ..G..AAG.AGGAAGT...T.CG...      .TGGA..C..C..C..GC.............

V_L Sequences

Framework I              CDR I         Framework II       CDR II         Framework III                          CDR III        J Region
                                  ABCDE
              10       20         30           40                 50             60       70       80               90              100
        ASLSASVGETVTITC RASE    NIYSYLA    WYQQKQGKSPQLLVY NAKILAE GVPSRFSGSGSGTQFSLKINSLQPEDFGSYYC QHHYGTPFT      FGTGTKLEIK
15d8    ............... ....    .......    ............... .......  ................................ .........      ..........
9f11    ............... ....    .......    ............... .......  ................................ .........      ..........
15b10   V.............. ....    .......    ............... .......  ................................ .........      ..........
5f3     ............... ....    .......    ............... .......  ................................ .........      ..........
4b2     .IMA..P..K..M.. S..SS    VSSGNFH    ......P.T..K.WI.  RTSN..S ...A.............SY..T..S..MEA..AAT.. .QWS.Y.R.    .G........
10f4    L..PV.L.DQAS.S. .S.QSLVHN.GNT..H  .L..P.Q..K..I.   KVSNRFS ...D.............D.T....SRVEA..L.V.F. SQSTHV.P.    .G........
7b3     ...AE.L.QKA..S. K..KKVTIFGSI.A.H  ......P.QP.K..I.   .GAK.ES .SA...D...???.T.T.DPVEAD..AAT.. LQNKEV.Y.    .S........
8d8     .IMA..P..K..M.. S..SS    VSPGNFH    ......P.P..K.WI.  RTSN..S ...A.............SY..T..S..MEA..AAT.. .QWS.Y.R.    .G........
11f8    ..AV.L.QS....S. ....SVEY YGT.LMQ   ......P.QP.K..I.   G.SNVES ...A...D...N.HPVEED.IAM.F.        .QSRKV.S.    .G........

THERAPEUTIC METHODS FOR BENZODIAZEPINE DERIVATIVES

This application is a divisional of application Ser. No. 08/443,540, filed May 18, 1995, now abandoned.

This work was performed in part with the government funding under grants from the National Institute of Health 08270) and from a grant from the University of Michigan Multipurpose Arthritis Center (NIH Grant AR 20557). Accordingly, the United States government may have rights in this invention.

FIELD OF THE INVENTION

This invention relates to novel antibodies which bind ssDNA and dsDNA. cl BACKGROUND OF THE INVENTION Throughout this application are publications referenced by arabic numerals within parenthesis. Full citations for these publications may be found at the end of the specification immediately preceding the claims. The disclosures of these publications, as well as issued U.S. Patents and published patent specifications referenced in this application are hereby incorporated by reference into the present disclosure to more fully describe the state of the art to which this invention pertains.

Systemic Lupus Erythematosus ("SLE") is a human autoimmune disease mediated by pathogenic immune complexes. The immune complexes believed to play a key role in the renal pathology of systemic lupus erythematosus ("SLE") comprise anti-DNA autoantibodies (hereinafter "anti-DNA") which localize within the basement membrane of the glomerulus (1–4). However, not all anti-DNA cause renal damage and establishing a relationship between the physical properties of these antibodies, their affinity and mechanisms of antigen binding, and pathogenesis remains a central goal of SLE research (47).

The presence of serum anti-DNA autoantibodies is one of the clinical features of the autoimmune disease systemic lupus erythematosus (SLE). The involvement of anti-dsDNA in the renal pathology of SLE has been inferred from the correlation of disease activity with the presence anti-dsDNA, and the isolation of anti-DNA from renal eluates. However, a clear understanding of the series of events that lead from the production of anti-DNA to their site of tissue localization has not been elucidated.

To this end, early efforts in this area was concentrated to defining the binding properties and physical characteristics of anti-DNA which employed polyclonal sera obtained from both patients afflicted with SLE and murine models of this disorder (10, 11). A great deal of the early research effort was to elucidating the determinants involved in self recognition and the interactions that stabilize DNA•anti-DNA interactions (16). For a variety of reasons, the general features of dsDNA epitopes and the parameters that distinguish high and low affinity anti-dsDNA are not well defined. This point is particularly significant since anti-dsDNA levels seem to correlate with disease activity (3). Indirect evidence from comparative sequence alignments of anti-dsDNA (15), and competition binding experiments using chemically modified dsDNA duplexes (21) suggest that anti-dsDNA may recognize epitopes on the bases in both the major and minor groove, as well as on the phosphate backbone of dsDNA. Binding of dsDNA may also involve more electrostatic interactions than recognition of ssDNA (22).

Thus, a need exists to further elucidate the pathological interaction of DNA with autoantibodies and to relate this interaction to inflammatory glomerulonephritis and SLE. This invention provides the reagents and methods to this end.

SUMMARY OF THE INVENTION

This invention provides a monoclonal antibody with high affinity for single-stranded DNA, low or no affinity for double-stranded DNA, and capable of specifically binding a DNA hairpin. Also provided herein are hybridoma cell lines which produces these monoclonal antibodies.

A chimeric mouse comprising these hybridoma cell lines and a histocompatible mouse is further provided.

A method for screening for an agent which will inhibit anti-DNA antibody-DNA binding is provided herein. The method requires providing an anti-DNA antibody bound to a solid support; contacting the agent to be tested with the receptor bound support under conditions favoring binding of antibody to DNA and contacting detectably-labeled DNA to the solid support of under conditions favoring binding of DNA to anti-DNA. The presence of any complex formed between the antibody and the DNA is then detected, the absence of complex being indicative that the agent inhibits binding of antibody to DNA.

Finally, a method of inhibiting the binding of an anti-DNA antibody to its DNA ligand in a sample by contacting the sample with an effective amount of a benzodiazepine derivative is encompassed by this invention.

DESCRIPTION OF THE FIGURES

In FIG. 4A, fluorescence titration obtained for 9F11. The mAb (0.87 μM) was excited at 295 nm and the emission was monitored from 300–450 nm as a function of DNA concentration (O-2 μM). The spectra shown are baseline corrected. All mAb's exhibit fluorescence quenching in the presence of poly(dT). FIG. 4B is a calculation of the number of bases occluded upon binding. The percent fluorescence quenching was quantified by integrating the fluorescence spectra at each titration point relative to the free protein. The molar concentration of bases was determined using the extinction coefficient for phosphate ($8.1\times10^3$ M$^{-1}$ cm$^{-1}$) as described by Kim et al. (38). The initial and final slopes are determined from best fits to the first and last five data points and extrapolated to the point of intersection. The intersection of the initial and final slopes represent the number of nucleotides occluded in the binding site (36). Similar results are obtained for all mAb's studied when using a ten-fold lower protein concentration, suggesting that protein binding is noncooperative (63). Due to their relatively low affinity, mAb's 4B2, 7B3 and 10F4 do not yield a distinct saturation point. Based on the data for these antibodies, it is estimated that between four to six consecutive nucleotides are occluded upon binding.

FIG. 6A is an autoradiography of cleavage products separated by denaturing gel electrophoresis. Lanes 1 and 2, G+A and T sequencing reactions, respectively; lanes 3 and 4, KMnO$_4$ modification in the absence (lane 3) or presence (lane 4) of nIgG; lanes 5–12, KNbO$_4$ modification in the presence of mAb's 4B2 (lane 5), 7B3 (lane 6), 8D8 (lane 7), 10F4 (lane 8), 9F11 (lane 9), 15B10 (lane 10), 15D8 (lane 11), and 11F8 (lane 12). FIG. 6B is representative densitometry traces comparing KMnO$_4$ reactivity of DNA in the presence of nIgG and mAb's 4B2, 9F11 and 11F8. FIG. 6C shows the difference probability maps calculated from the densitometry plots in B and presented in the same order. The difference in KMnO$_4$ modification at each thymidine is represented by bars and is calculated by subtracting the logarithm of the probability of modification at each position in the free DNA (Fn) from the same position in the complex ($P_n$) according to Rhodes (64). A larger negative value of $\ln(P_n)-\ln(F_n)$ indicates greater protection from modification.

FIGS. 7A and 7B show the anti-DNA $V_H$ chain nucleotide and deduced amino acid sequence. Sequences (SEQ ID NOS: 5–22) were aligned using the SAW software. Nomenclature and numbering were according to Kabat. Sequences begin after the $V_H$ primer at position 23 in codon 8. Identities are indicated by (•) and gaps are indicated by (–).

FIGS. 8A and 8B show the anti-DNA $V_\kappa$ chain nucleotide and deduced amino acid sequence. Sequences (SEQ ID NOS: 23–40) are displayed according to the legend of FIG. 7. Sequences begin after the $V_\kappa$ primer at position 28 in codon 9.

FIG. 9 is the putative consensus $V_H$ and $V_L$ nucleotide (Panel A (SEQ ID NOS: 41–49) and B (SEQ ID NOS: 49–57), respectively) and amino acid sequences (Panel C (SEQ ID NOS: 57–76)) for the 9F11 group, 4B2, and 11F8. The sequences were derived using the SAW software by aligning homologous anti-DNA whose sequences have been published (found in Table I) as well as several antibodies of other specificities obtained from a search of the GenBank database. The statistically most represented nucleotide at each position was defined as the consensus nucleotide at that position. In searching the GenBank database, care was taken to avoid using multiple sequences from the same source. The GenBank accession numbers for unrelated antibodies is as follows. For 9F11 $V_H$: S59838, X64998, Z29586, X00160, K00706; 9F11 $V_\kappa$: Z22096, X69859, S53109, U00929, X01431; 4B2 $V_H$: U09593, L22535, X80958, X13188, J00507; 4B2 $V_\kappa$: M18239, D14630, L09009, J00575, U01851; 11F8 $V_H$: K00723, S50914, S51594, X15471, M36228, L14742; 11F8 $V_\kappa$: X16955, L18942, M34633, M31270, S64047. Sequences are displayed as described in the legend of FIG. 7. The genealogy of the 9F11 group could not be determined due to the lack of sufficient parallel and unique somatic mutations that can be used to elucidate branchpoints in the evolution of these mAb's.

DISCLOSURE OF THE INVENTION

Definitions

Figure 1:
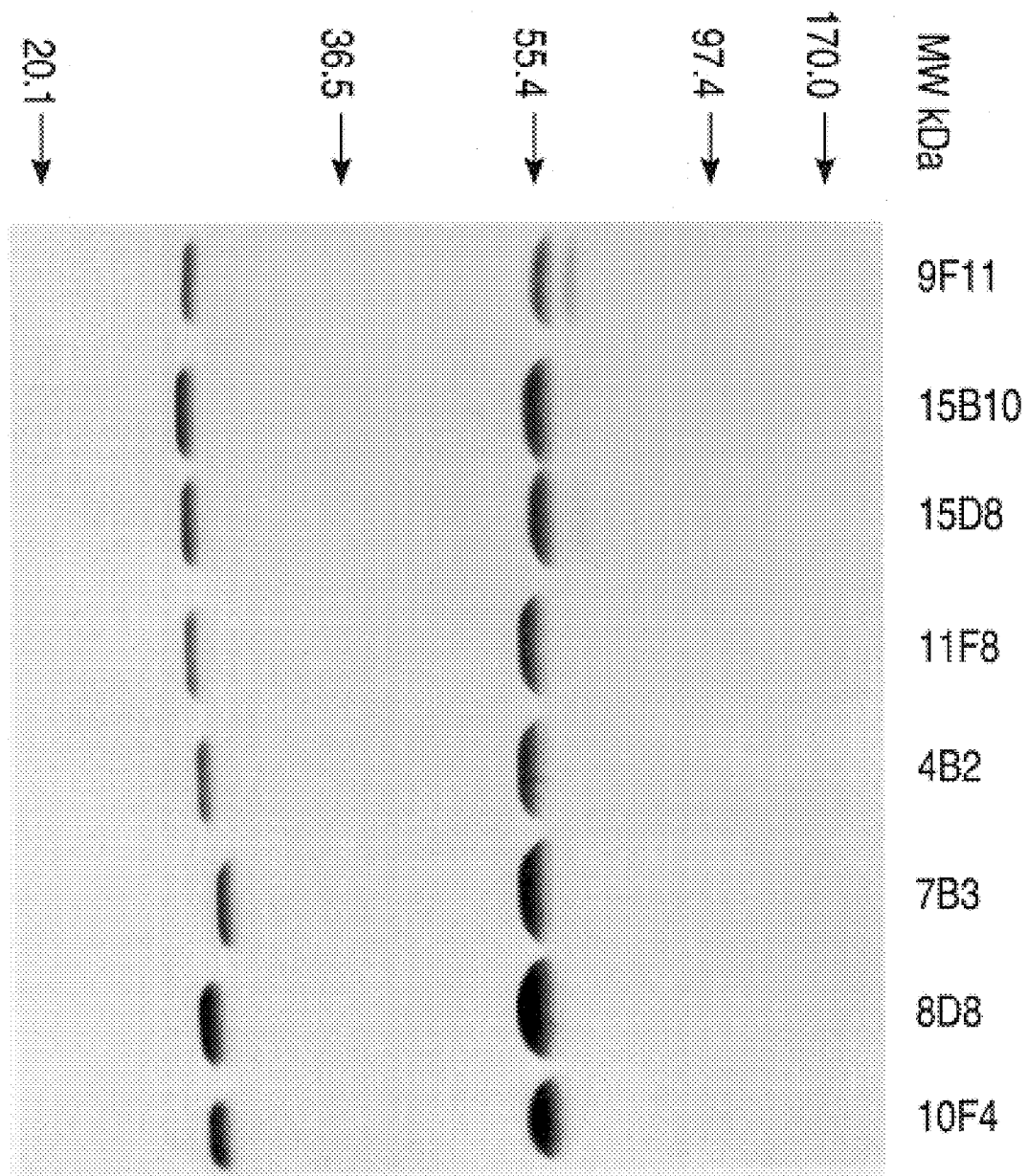
FIG. 1 shows SDS-PAGE of fully purified anti-DNA. Samples (3–5 μg) were electrophoresed on 10% polyacrylamide-SDS gels and stained with commassie blue. The minor band above the heavy chain in lanes containing IgG2b anti-DNA are the result of asymmetric glycosylation of the heavy chain (38).

The terms "proteins", "peptides" and "polypeptides" are used interchangeably and are intended to include molecules containing amino acids linearly coupled through peptide bonds. The amino acids of can be in the L or D form so long as the biological activity of the polypeptide is maintained. These also include proteins which are post-translationally modified by reactions that include glycosylation, acetylation and phosphorylation. Such polypeptides also include analogs, alleles and allelic variants which can contain amino acid derivatives or non-amino acid moieties that do not affect the biological or functional activity of the protein as compared to wild-type or naturally occurring protein. The term amino acid refers both to the naturally occurring amino acids and their derivatives, such as TyrMe and PheCl, as well as other moieties characterized by the presence of both an available carboxyl group and an amine group. Non-amino acid moieties which can be contained in such polypeptides include, for example, amino acid mimicking structures. Mimicking structures are those structures which exhibit substantially the same spatial arrangement of functional groups as amino acids but do not necessarily have both the α-amino and α-carboxyl groups characteristic of amino acids.

"Muteins" are proteins or polypeptides which have minor changes in amino acid sequence caused, for example, site-specific mutagenesis or other manipulations; by errors in transcription or translation; or which are prepared synthetically by rational design. These minor alterations result in amino acid sequences wherein the biological activity of the protein or polypeptide is altered as compared to wild-type or naturally occurring polypeptide or protein.

As used herein, the term "peptide bond" or "peptide linkage" refers to an amide linkage between a carboxyl group of one amino acid and the α-amino group of another amino acid.

As used herein, the term "hydrophobic" is intended to include those amino acids, amino acid derivatives, amino acid mimics and chemical moieties which are non-polar. Hydrophobic amino acids include Phe, Val, Trp, Ile and Leu. As used herein, the term "positively charged amino acid" refers to those amino acids, amino acid derivatives, amino acid mimics and chemical moieties which are positively charged. Positively charged amino acids include, for example, Lys, Arg and His.

"Purified" when referring to an antibody, protein or polypeptide, are distinct from native or naturally occurring antibodies, proteins, polypeptides or antibodies because they exist in a purified state. These "purified" proteins or polypeptides, or any of the intended variations as described herein, shall mean that the compound or molecule is substantially free of contaminants normally associated with the compound in its native or natural environment.

"Native" polypeptides, proteins, antibodies or nucleic acid molecules refer that those recovered from a source occurring in nature or "wild-type".

A "composition" is intended to mean a combination of active agent and another compound or composition, inert (for example, a detectable agent or solid support) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, *Remington's Pharm. Sci.*, 15th Ed. (Mack Publ. Co., Easton (1975)).

The term "nucleic acid" means single and double stranded DNA, cDNA and RNA, as well as the positive and negative strand of the nucleic acid which are complements of each other, including anti-sense RNA. A "nucleic acid molecule" refers to a polymeric form of nucleotides of any length, either ribonucleotides or deoxyribonucleotides, or analogs thereof. An "analog" of DNA, RNA or a polynucleotide, refers to a macromolecule resembling naturally occurring polynucleotides in form and/or function (particularly in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al. (1990) *Chemical Reviews* 90:543–584.

"Isolated" when referring to a nucleic acid molecule, means separated from other cellular components normally associated with native or wild-type DNA or RNA intracellularly or in serum.

An "antisense" copy of a particular polynucleotide refers to a complementary sequence that is capable of hydrogen bonding to the polynucleotide and can therefor, be capable of modulating expression of the polynucleotide. These may be DNA, RNA or analogs thereof, including analogs having altered backbones, as described above. The polynucleotide to which the antisense copy binds may be in singe-stranded form or in double-stranded form.

As used herein, the term "operatively linked" means that the DNA molecule is positioned relative to the necessary regulation sequences, e.g., a promoter or enhancer, such that a promoter will direct transcription of RNA off the DNA molecule in a stable or transient manner.

"Vector" means a self-replicating nucleic acid molecule that transfers an inserted nucleic acid molecule into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above functions.

"Host cell" is intended to include any individual cell or cell culture which can be or have been recipients for vectors or the incorporation of nucleic acid molecules and/or proteins. It also is intended to include progeny of a single cell, and the progeny may not necessarily be completely identical (in morphology or in genomic or total DNA complement) to the original parent cell due to natural, accidental, or deliberate mutation.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

MODES FOR CARRYING OUT THE INVENTION

Significant advances to understanding the involvement of anti-DNA in SLE have been made in the last decade. However, the factors involved in initiating and sustaining the anti-DNA response remain elusive. Analysis of the V-region genes of monoclonal antibodies derived from lupus-prone mice has revealed that anti-DNA are oligoclonal and exhibit patterns of somatic mutation to residues like arginine and asparagine that can interact with and improve affinity to DNA (13–15). These results are consistent with an autoantigen driven response in which stimulation by DNA or a DNA-containing complex results in affinity maturation toward DNA antigens. Although the specific molecule(s) that drives this response in vivo is still unknown, free DNA and protein-DNA complexes such as nucleosomal particles are likely candidates (41). This hypothesis, however, is not consistent with the observation that dsDNA is not immunogenic (71) and has led to the proposal that in SLE, tolerance defects exist that permit autoreactive B cells to escape the mechanisms normally in place to anergize or eliminate them (72). In support of this latter hypothesis, differential expression of regulatory genes in mice (e.g., Fas/Apol and BCL2) has been implicated in the etiology of autoimmunity by facilitating the survival of autoreactive T and B cells (73, 74). While identifying the defects that lead to this breakdown in tolerance is necessary to gain a full understanding of SLE, constructing a conceptual framework to explain ssDNA and dsDNA binding in anti-DNA is an important first step for understanding immune self recognition and ultimately pathogenicity.

This invention provides the reagents and methods for elucidating this complex pathology. Also provided by this invention are methods to inhibit the pathological complex formation implicated in this disease state thereby providing a therapy for its eradication.

Antibodies and Cell Lines

This invention provides a monoclonal antibody with high affinity for single-stranded DNA and single-stranded oligo-dT, low or no affinity for double-stranded DNA, and capable of specifically binding to DNA hairpin structure. A panel of antibodies with these specificities has been generated. They are useful in the diagnosis of disorders which are associated with the pathological complexation of DNA, such as inflammatory glomerulonephritis and SLE, as well as for the generation of reagents to screen for pharmaceutical agents and therapies for the treatment and prevention of these diseases.

As used herein, an "antibody" means a monoclonal antibody which is produced in an animal that reacts with DNA with an effective specificity and affinity for its intended purpose. The animal is sacrificed and its spleen cells are removed for fusion with an immortalized cell line such as a heteromyeloma to produce a clonal cell line. All monoclonal antibodies derived from the clone are chemically and structurally identical, and specific for a single antigenic determinant. The hybridoma cell lines producing the monoclonal antibodies also are within the scope of this invention. These monoclonal antibodies can be from any species, e.g., mice, rat, rabbit or a human monoclonal antibody.

As used herein, the term "monoclonal antibody" or "antibody" also are intended to include antibody fragments (variable and framework regions) and recombinant antibodies having a variable and/or framework region of an antibody of this invention combined with the same from another source. Further intended by the use of this term is antibodies which have changes in their primary amino acid sequences.

As used herein, the term "high affinity" shall mean an apparent equilibrium dissociation value of less than 1 micromolar and "low affinity" shall mean an apparent equilibrium dissociation value of more than 1 micromolar. Examples of high affinity antibodies include, but are not limited to the antibodies designated herein 9F11, 15B10, 15D8, and 11F8. Specifically excluded are the prior art antibodies Bv04-01 and Hed10. Examples of low affinity antibodies include, but are not limited to 4B2, 7B3, 8D8, 10F4 and 5F3. Specifically excluded is the prior art antibody 3H9.

The hybridoma cell line 11F8 has been deposited with the American Type Culture Collection (ATCC) 12301 Parklawn Drive, Rockville Md. U.S.A. 20852 on May 18, 1995 under the provisions of the Budapest Treaty for the International Recognition of the Deposit of Microorganisms for the Purposes of Patent Procedure. It was accorded Accession No. HB 11890.

Laboratory methods for producing the antibodies of this invention also are provided below, as well as methods for deducing their corresponding nucleic acid sequences. Additional methodologies for producing monoclonal antibodies and deducing their sequences, are known in the art, see Harlow and Lane, (1988) *Antibodies: A Laboratory Manual*, Cold Spring Harbor Laboratory, New York and Sambrook et al. (1989) *Molecular Cloning: A Laboratory Manual*, Cold Spring Harbor Laboratory. Briefly, the monoclonal antibodies of this invention can be biologically produced by introducing an immunological nucleic acid molecule into an animal, e.g., a mouse or a rabbit. The antibody producing cells in the animal are isolated and fused with myeloma cells from the same or different species (mouse, rabbit or human) or heteromyeloma cells to produce hybrid cells or hybridomas. Accordingly, the hybridoma cells producing the monoclonal antibodies of this invention also are provided. As noted above, these hybridoma cells can be the result of mouse-mouse fusion, mouse-human fusion or human-human fusion methods. The immortalized cell lines (fusion partners) are commercially available from a variety of sources, including the ATCC.

This invention also provides biologically active fragments of the antibodies described above, e.g., a polypeptide consisting essentially of the framework or variable region of a monoclonal antibody of this invention. These "antibody fragments" retain some ability to selectively bind with its DNA antigen or immunogen, in this case ssDNA, dsDNA or both. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', which traditionally has been defined at the fragment of an antibody molecule obtained by treating with pepsin, followed by reduction, to yield an intact light chain and a portion of the heavy chain; two Fab' fragments are obtained per antibody molecule;

(3) F(ab')$_2$, the fragment of the antibody that is obtained by treating with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule. A specific examples of "biologically active antibody fragment" include the CDR regions of the antibodies. Methods of making these fragments are described below and in Harlow and Lane, (1988) supra.

As noted above, the antibodies of this invention also can be modified to create chimeric antibodies and humanized antibodies (Oi, et al. (1986) *BioTechniques* 4(3):214). Chimeric antibodies are those in which the various domains of the antibodies' heavy and light chains are coded for by DNA from more than one species. Accordingly, further provided by this invention are recombinant antibodies containing the variable region from an antibody, wherein the antibody has high affinity for single-stranded DNA, low or no affinity for double-stranded DNA, and capable of specifically binding DNA hairpin structure. In one embodiment of this invention, the antibodies specifically bind an adjacent stem duplex without unwinding the stem duplex. Example of such recombinant are the antibodies designated 4B2 and 9F11HCDR3. In a further embodiment they have high affinity for single-stranded oligo-dT.

The isolation of other hybridomas secreting monoclonal antibodies with the specificity of the monoclonal antibodies of the invention can also be accomplished by one of ordinary skill in the art by producing anti-idiotypic antibodies (Herlyn, et al. (1986) *Science*, 232:100). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with similar idiotypes as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic the DNA binding area of the nucleic acid binding partner of the antibody. These anti-idiotypic antibodies are useful in an immunochemical screen for the presence of the antibodies of this invention. For example, an anti-idiotypic monoclonal antibody made to a first monoclonal antibody will have a binding domain in the hypervariable region which is the mirror image of the epitope bound by the first monoclonal antibody.

Also provided by this invention are compositions having the antibody (recombinant, polyclonal, monoclonal, fragments or anti-idiotypic) described above and a carrier. The antibodies of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare anti-idiotypic antibodies, the carriers also can include an adjuvant which is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

Equivalent antibodies to the antibodies specifically described herein are within the scope of this invention. To determine whether antibodies are "equivalent" one of skill in the art will know to test whether the test antibody binds with the same specificity to the DNA target. If they do, they are equivalent. It also is possible to determine without undue experimentation, whether an antibody has the same specificity as the antibody of this invention by determining whether the antibody being tested prevents an antibody of this invention from binding it DNA target with which the monoclonal antibody is normally reactive. If the antibody being tested competes with the antibody of the invention as shown by a decrease in binding by the antibody of this invention, then it is likely that the two antibodies bind to the same or a closely related epitope. Alternatively, one can pre-incubate the antibody of this invention with the target DNA with which it is normally reactive, and determine if the monoclonal antibody being tested is inhibited in its ability to bind the DNA. If the antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

Also encompassed by this invention are proteins or polypeptides that have been recombinantly produced, biochemically synthesized, chemically synthesized or chemically modified, that retain the ability to bind DNA with the same affinity and specificity defined herein.

The antibodies of this invention can be linked to a detectable agent or a hapten. The complex is useful to detect the DNA in a sample or detect agents which interfere with antibody-DNA binding, using the methods described below. Examples of types of immunoassays which can utilize antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The antibodies of the invention can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the antibody, or will be able to ascertain such, using routine experimentation. Furthermore, the binding of these labels to the antibody of the invention can be done using standard techniques common to those of ordinary skill in the art. The antibodies also can be combined with pharmaceutical carriers and adjuvants for the preparation of anti-idiotypic antibodies. The fusion or hybridoma cell lines which produce the antibodies also can be combined with pharmaceutical carriers for administration to immunohistocompatible mice to generate a chimeric mouse useful to screen and test new therapies for the prevention and treatment of pathologies associated with antissDNA-DNA complexes like glomerulonephritis.

The antibodies and fragments of this invention can biologically produced from hybridoma cell lines alone or in combination with chemical digestion to yield the fragments thereof or they can be obtained by chemical synthesis using a commercially available automated peptide synthesizer such as those manufactured by Applied Biosystems, Inc., Model 430A or 431A, Foster City, Calif. and the amino acid sequence of the antibodies or the fragments as provided in FIGS. 7 through 10. The synthesized protein or polypeptide can be precipitated and further purified, for example by high performance liquid chromatography (HPLC). Accordingly, this invention also provides a process for chemically synthesizing the antibodies and fragments thereof by providing the sequence of the antibody or fragment and reagents, such as amino acids and enzymes and linking together the amino acids in the proper orientation and linear sequence.

Alternatively, the antibodies can be obtained by well-known recombinant methods as described, for example, in Sambrook et al., *Molecular Cloning: A Laboratory Manual* 2d ed. (Cold Spring Harbor Laboratory (1989)) using the host cell and vector systems described below. Thus, this invention further provides a process for recombinantly producing an antibody or fragment thereof, by growing a host cell containing a nucleic acid molecule encoding the antibody or fragment thereof, the nucleic acid molecule being operatively linked to a promoter of RNA transcription. The host cell is grown under suitable conditions such that the nucleic acid is transcribed and translated into protein and purifying the protein so produced.

Also provided by this application are the antibodies and fragments thereof described herein conjugated to a detectable agent for use in diagnostic methods. For example, detectably labeled anti-idiotypic antibodies or a fragment containing a conformationally stabilized fragment having similar specificity and avidity as the native anti-idiotypic antibody, can be bound to a column and used for the detection and purification antibodies of this invention. It is preferable that the serum sample contacted with more that one antibody of this invention to determine its binding pattern. The binding pattern then can be correlated to determine whether the patient from whom the serum sample was obtained is predisposed to or has the a pathology associated with the presence of. antissDNA-DNA complexes.

The antibodies or fragments thereof which contain a conformationally stabilized binding site having similar biding specificity and avidity as native antibody also can be used (as above or in any of the standard immunochemical techniques such as ELISA) to test for agents which interfere with or prevent the binding of DNA, preferably ssDNA, to its antibody.

Nucleic Acids

Further provided by this invention is a nucleic acid molecule coding for a monoclonal antibody of this invention or a polypeptide corresponding to the variable or framework region of a monoclonal antibody, wherein the monoclonal antibody is characterized by having high affinity for single-stranded DNA, low or no affinity for double-stranded DNA, and being capable of specifically binding a hairpin DNA. As used herein, the term "high affinity" shall mean apparent equilibrium dissociation values of less than 1 micromolar and "low affinity" shall mean apparent equilibrium dissociation values of more than 1 micromolar. Also intended to be encompassed by this invention are the complements (DNA and RNA) to these nucleic acid molecules.

Examples of such nucleic acid molecules are the nucleic acids coding for the antibodies designated 9F11, 15B10, 15D8, and 11F8. Specifically excluded are nucleic acid molecules coding for the prior art antibodies Bv04-01 and Hed10. Examples of nucleic acids coding for low affinity antibodies include, but are not limited to the nucleic acids coding for the antibodies designated 4B2, 7B3, 8D8, 10F4 and 5F3. Specifically excluded is the nucleic acid molecule coding for the prior art antibody 3H9.

In a further embodiment the nucleic acid molecules coding for unrelated antibodies having the following GenBank Accession numbers: For 9F11 $V_H$: S59838, X64998, Z29586, X00160, K00706; 9F11 $V_\kappa$: Z22096, X69859, S53109, U00929, X01431; 4B2 $V_H$: U09593, L22535, X80958, X13188, J00507; 4B2 $V_\kappa$: M18239, D14630, L09009, J00575, U01851; 11F8 $V_H$: K00723, S50914, S51594, X15471, M36228, L14742; 11F8 $V_\kappa$: X16955, L18942, M34633, M31270, S64047; are specifically excluded.

With the nucleic acid molecules, one of skill in the art can recombinantly reproduce the nucleic acid molecules or the antibodies, anti-idiotypic antibodies or polypeptides encoded by them using methods known to those of skill in the art and described in Sambrook et al., *Molecular Cloning: A Laboratory Manual* 2d ed. (Cold Spring Harbor Laboratory (1989)) with the host cell and vector systems described below. This invention further provides a process for producing an antibody, anti-idiotypic antibody or fragments thereof by growing a host cell containing a nucleic acid molecule encoding the antibody, anti-idiotypic antibody, protein or fragments thereof, the nucleic acid being operatively linked to a promoter of RNA transcription. The host cell is grown under suitable conditions such that the nucleic acid is transcribed and translated. In one embodiment, the antibody product is purified.

As noted above, nucleic acid molecules and isolated nucleic acid molecules which encode amino acid sequences corresponding to an antibody fragment or an antibody of this invention, as well as complements of these sequences, are further provided by this invention. In addition to these sequences the sequences shown in the FIGS. 7 through 10 corresponding to fragments of the antibodies of this invention also provides the anti-sense polynucleotide stand, e.g. antisense RNA. One can obtain an antisense RNA using the sequence of the antibodies or the sequences of the fragments provided in the FIGS. 7 through 10 and the methodology described in Vander Krol et al. (1988) *BioTechniques* 6:958.

In one aspect of this invention, the nucleic acid molecule encoding a fragment of the antibody is defined to be any of the sequence or parts thereof shown in FIGS. 7 through 10. Expression of functional fragments in bacterial cells (4BscF$_v$) has been accomplished with *E. coli* HB2151 cells (ATCC) by adding plasmid containing the nucleic acid fragment to *E. coli* cells in culture. The sample is incubated on ice for 45 minutes and then heat shocked for 2 minutes at 42° C., and then chilled on ice for 5 minutes. An aliquot of the transformation reaction (100 μL) was added to LBG media (900 μL), incubated for 1 hour at 37° C. and then plated on selective media containing antibiotics. After growth for approximately 12 hours at 30° C., plasmid DNA was isolated and digested with Sfi I and Not I as described above. Restriction enzyme analysis can be used to confirm presence of insert.

Suitable culture for the bacteria is inoculated with bacterial culture. containing the insert and grown at 30° C. for 12 hours. Additional media is added and the culture is grown for an additional 1 hour with vigorous shaking. Culture is removed and pelleted by centrifugation at 1500 g. For isolation of the polypeptide, the cells were resuspended in PBS (o.fmL containing 1 mM EDTA) incubated on ice for 10 minutes and then centrifuged to pellet the cell debris. The whole cell extract was prepared by resuspending the cell pellet in PBS (0.5 mL) boiling for 5 minutes and centrifugation to pellet the cell debris. Aliquots of the supernatant, periplasm and whole cell extract were analyzed by SDS-PAGE. A band migrating at 28 kDa was observed in the periplasmic extract indicating soluble expression of the polypeptide.

Periplasmic extracts are bound to a Sepharose-anti-E Tag antibody column (5 mL bed volume; 1 mg anti-E Tag/mL of Sepharose) at a flow rate of 1 mL/minute. Afer washing with PBS (50 mL0 and 0.1 M glycine (25 mL, Ph 5.0), the $scF_v$'s will be eluted with 0.1 M glycine buffer (pH 2.8) into 0.2 M TRIS-HCl, pH 8.0 (175 μL; 2 mL fractions. The purity of each $scF_v$ is assessed by SDS-PAGE, IEF and ion exchange chromatography using a DEAE matrix. If the samples are (95% homogenous, they are further purified by affinity chromatography over agarose-ssDNA and if needed by ion exchange chromatography. This latter ion exchange step may prove critical for mutant $scF_v$'s that do not bind to the agarose-ss DNA column.

Although each $scF_v$ is expected to be primarily be localized in the periplasm in soluble form, it is possible that some proteins may form inclusion bodies or co-precipitate with the cell pellet. In either of these cases it will be necessary to denature and re-fold the $scF_v$ prior to chromatographic purification. As a starting point for these experiment, the conditions reported by Pantoliano et al. are used. Briefly, cell paste will be isolated by centrifugation (11000 g) and suspended in 10 volumes of buffer (50 mN TRIS-HCl, 1 mM EDTA, 0.1 mM PMSF, pH 8). The mixture will be passed through a French press apparatus (10,000 psi) and the homogenate will be pelleted by centrifugation. After repeating the homogenization, the protein pellet is washed with TRIS buffer and then dissolved in denaturation buffer (6 M guanidinium hydrochlorine, 50 mM TRIS-HCl, 50 mN KCl, pH 8 to a total protein concentration of 10 mg/mL). The dissolved $sdF_v$ will then be diluted rapidly (1:200) into renaturation buffer at 7° C. (50 mM TRIS-HCl, 50 mM KCl, 10 mM $CaCl_2$, 0.1 mM PMSF, pH 8) and allowed to sit for 24 hours without agitation. Following filtration (Millipore MiniTAN apparatus using a 10 $kD_a$ cutoff membrane), concentration (Centriprep concentrators), and dialysis against glycine buffer, the $scF_v$ are chromatographically purified as described above. If significant quantities of the $scF_v$'s leak into the growth medium (as might be caused by over-expression) they are concentrated and purified chromatographically as described herein.

The invention also encompasses nucleic acid molecules which differ from that of the nucleic acid molecules described above, but which produce the same phenotypic effect, such as the allele. These altered, but phenotypically equivalent nucleic acid molecules are referred to "equivalent nucleic acids." This invention also encompasses nucleic acid molecules characterized by changes in non-coding regions that do not alter the phenotype of the polypeptide produced therefrom when compared to the nucleic acid molecules that encode the naturally occurring antibody or anti-idiotypic antibody. This invention further encompasses nucleic acid molecules which hybridize to the nucleic acid molecules of the subject invention under stringent conditions.

The nucleic acid molecules can be conjugated to a detectable marker, e.g., an enzymatic label or a radioisotope for detection of nucleic acid and/or expression of the gene encoding the antibodies in a cell or serum. Briefly, this invention further provides a method for detecting a single-stranded nucleic acid molecule encoding an amino acid sequence which is at least a portion of an antibody of this invention by contacting single-stranded nucleic acid molecules with a labeled, single-stranded nucleic acid molecule (a probe) which is complementary to a single-stranded nucleic acid molecule encoding an amino acid sequence which is at least a portion of an antibody under conditions permitting hybridization (preferably stringent hybridization conditions) of complementary single-stranded nucleic acid molecules. Hybridized nucleic acid molecules are separated from single-stranded nucleic acid molecules. The hybridized molecules are detected using methods well known to those of skill in the art and set forth, for example, in Sambrook (1989) infra.

The nucleic acid molecules of this invention can be replicated and isolated using the recombinant technique described above or replicated using PCR (Perkin-Elmer) as described below. For example, the sequence can be chemically replicated using PCR (Perkin-Elmer) which in combination with the synthesis of oligonucleotides, allows easy reproduction of DNA sequences. The PCR technology is the subject matter of U.S. Pat. Nos. 4,683,195, 4,800,159, 4,754,065, and 4,683,202 and described in *PCR: The Polymerase Chain Reaction* Mullis et al. eds, Birkhauser Press, Boston (1994) and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the nucleic acid into a suitable replication vector and insert the vector into a suitable host cell for replication and amplification. The DNA so amplified can be isolated from the cell by methods well known to those of skill in the art. A process for obtaining nucleic acid molecules by this method is further provided herein as well as the nucleic acid molecules so obtained.

RNA can be obtained by using the isolated DNA and inserting it into a suitable cell. A suitable cell for this purpose includes but is not limited to a bacterial cell, a yeast cell, or a mammalian cell. The DNA can be inserted by any appropriate method, e.g., by the use of an appropriate insertion vector or by electroporation. When the cell replicates and the DNA is transcribed into RNA; the RNA can then be isolated using methods well known to those of skill in the art, for example, as set forth in Sambrook et al. (1989) infra.

The invention further provides the isolated nucleic acid molecule operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted nucleic acid molecule. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see *Gene Expression Technology*, Goeddel ed., Academic Press, Inc. (1991) and references cited therein and *Vectors: Essential Data Series* Gacesa and Ramji, eds., John Wiley & Sons, N.Y. (1994), which contains maps,. functional properties, commercial suppliers and a reference to GenEMBL accession numbers for various suitable vectors. Preferable, these vectors are capable of transcribing RNA in vitro or in vivo.

As noted above, an isolated nucleic acid molecule of this invention can be operatively linked to a promoter, either an inducible or non-inducible promoter, of RNA transcription. Accordingly, this invention also provides a vector (insertion, replication or expression vector) having inserted therein an isolated nucleic acid molecule described above, for example, a viral vector, such as bacteriophage, baculovirus and retrovirus, or cosmids, plasmids, YACS, yeast and other recombinant vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and anti-sense RNA.

An additional example of a vector construct of this invention is a bacterial expression vector including a promoter such as the lac promoter and for transcription initiation, the Shine-Dalgarno sequence and the start codon AUG (Sambrook et al. (1989) supra). Similarly, a eucaryotic expression vector is a heterologous or homologous promoter for RNA polymerase II, a downstream polyadenylation signal, the start codon AUG, and a termination codon for detachment of the ribosome. Such vectors can be obtained commercially or assembled using the sequences described herein.

Expression vectors containing these nucleic acids are useful to obtain host vector systems to produce the antibodies of the invention. It is implied that these expression vectors must be replicable in the host organisms either as episomes or as an integral part of the chromosomal DNA. Suitable expression vectors include viral vectors, including adenoviruses, adeno-associated viruses, retroviruses, cosmids, etc. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook et al. (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, an animal cell (rat or mouse), a human cell, or a bacterial cell, containing a nucleic acid molecule encoding an antibody or a polypeptide of this invention.

A Chimeric Mouse

The antibodies of this invention provide a novel reagent for a screen for pharmaceuticals and methods to treat or prevent pathological DNA-antibody binding, especially ssDNA-antibody binding which leads to severe inflammatory glomerulonephritis, inflammatory glomerulonephritis associated with SLE and nephritis associated with other diseases. The hybridoma cell lines which produce these antibodies can be administered to an immunohistocompatable non-autoimmune mouse. Suitable mice for this purpose include, but are not limited to BALB/c mice, p57 black mice or the mice described below. These animals are commercially available from Jackson Laboratories. Accordingly, also provided by this invention is a chimeric mouse having a hybridoma cell line of this invention. These mice are very suitable for screening for agents which inhibit pathological DNA•DNA-anti interactions.

Compositions

The antibodies, fragments, nucleic acid molecules and hybridoma cell lines of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare anti-idiotypic antibodies, the carriers also can include an adjuvant which is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

Thus, this invention also provides pharmaceutical compositions containing the antibodies, fragments, nucleic acid molecules and hybridoma cell lines and a pharmaceutically acceptable carriers. These are useful for the preparation of medicaments for the diagnosis and treatment of pathologies associated with antibody-DNA complex formation.

Industrial Applicability

The antibodies of this invention are useful not only for the generation of anti-idiotypic antibodies and recombinant antibodies, they also provide reagents for a cell-free screen for agents which may inhibit or prevent the binding of antibody to DNA, and preferably ssDNA. This is significant since it is the presence of complex which is deposited in the kidneys and leads to severe inflammatory glomerulonephritis.

To perform the cell free screen, an effective amount of an DNA, preferably heat denatured calf thymus DNA is first bound to a solid support (for example, glass, polystyrene, polyethylene, dextran, nylon, natural and modified celluloses, polyacrylamides, agaroses or coated onto microtiter plate). Those skilled in the art will know of other suitable carriers for this purpose.) in a suitable concentration, eg., between about 5 μg/ml to about 12 μg/ml, and more preferably between about 6 μg/ml and about 10 μg/ml. Then, approximately 10 μg/ml of agent is contacted with the DNA under suitable conditions which favor the binding of antibody to DNA. Subsequently or simultaneous with the previous contacting step, a diagnostically effective amount of anti-DNA antibody to be is contacted under suitable conditions which favor binding of the DNA to the antibody. Procedures for the detecting of complex are then performed. Simultaneously a control with no agent is performed. The amount of bound antibody is then compared relative to the control. If the agent prevented the formation of an antibody-DNA complex by greater than 50% at a concentration of 10 μM or less as compared to control, it is a candidate pharmaceutical.

The anti-idiotypic antibodies of this invention are similarly useful to screen for the presence of the antibodies of this invention which have been correlated with the presence of severe inflammatory glomerulonephritis and nephritis associated with other diseases. Using standard immunochemical techniques, a serum sample is obtained from the patient and contacted with a detectably labeled anti-idiotypic antibodies under suitable conditions which favor the formation of antibody-anti-idiotypic complex formation and determining whether any complex was formed. The presence of complex being a positive indication that the patient has or is predisposed to developing a disease caused by the presence of these complexes. This method also can be used to screen for drugs which will interfere or prevent the formation of these complexes and therefore are useful to treat or prevent the formation of complex and its associated disease.

Accordingly, this invention also provides a kit to perform the screens described above. The kits comprise the above reagents, control reagents and instruction for use to accomplish the objective of the screen.

This invention further provides administering a hybridoma cell line, preferably the cell line which produces antibody 11F8 to an immunocompatible non-autoimmune mouse and the chimeric mouse having these cells. The mouse is a powerful animal model to screen for agents which are an effective therapy to treat disorders associated with the formation of anti-DNA•DNA complex in an individual. This method comprises the steps of providing a mouse as identified above and administering an effective amount of a cell line which produces an antibody of this invention. The mouse is then maintained for an additional three to six days. The agent is then administered to the mouse and compared to the control, and if lives longer than the control, it is an effective agent.

As used herein, disorders associated with the formation of anti-DNA•DNA complex in an individual include but are not limited to severe inflammatory glomerulonephritis associated with SLE and nephritis associated with other diseases.

The drugs identified by this method also are provided by this invention. One class of drugs having this pharmaceutical efficacy is 1,4-benzodiazepine derivatives having the formula:

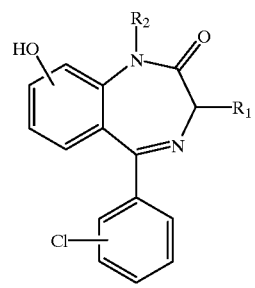

In the above formula, $R^1$ is a moiety comprising from 1 to about 30 hydrogen atoms and from 0 to about 15 carbon atoms. In certain embodiments, $R^1$ may further comprise from 1 to about 3 nitrogen atoms; from 1 to about 3 oxygen atoms; and from 1 to about 3 sulfur atoms. As described below, $R^1$ is derived from the α-amino acid used during synthesis. A group of preferred $R^1$ moieties includes —$CH_2CH_2COOH$ (derived from glutamic acid), —$CH_2COOH$ (derived from aspartic acid), —$CH_2$—$C_6H_5$ (derived from phenylalanine), —$CH_2CH_2$—$C_6H_5$ (derived from homophenylalanine), and —$CH(C_2H_5)CH_2$-(2-naphthyl) (derived from 2-naphthyl-isoleucine).

Also in the above formula, $R^2$ is a moiety comprising from 1 to about 30 hydrogen atoms and from 0 to about 15 carbon atoms. In certain embodiments, $R^2$ may further comprise from 1 to about 3 halogen atoms (such as iodine, bromine, chlorine, or fluorine); from 1 to about 3 nitrogen atoms; from 1 to about 3 oxygen atoms; and from 1 to about 3 sulfur atoms. As described below, $R^2$ is either —H or is derived from the optional alkylating agent used during synthesis. In one group of preferred embodiments, $R^2$ is simply —H. Another group of preferred $R^2$ moieties includes 4-bromo-benzyl and —$CH_2C(=O)O$—$C(CH_3)_3$).

Presently, the most preferred 1,4-benzodiazepines derivatives are the p-chloro-p-hydroxy-1,4-benzodiazepines shown below; the observed per-cent inhibition observed for each of these derivatives is also shown.

| Compound | $R^1$ | $R^2$ | % Inhibition |
|---|---|---|---|
| I | —$CH_2CH_2COOH$ | —$CH_2C(=O)OC(CH_3)_3$ | 50 |
| II | —$CH_2COOH$ | p-bromobenzyl | 40 |
| III | —$CH_2CH_2COOH$ | p-bromobenzyl | 50 |
| IV | —$CH(C_2H_5)CH_2$-(2-naphthyl) | —H | 95 |
| V | —$CH_2$—$C_6H_5$ | —H | 80 |
| VI | —$CH_2CH_2$—$C_6H_5$ | —H | 80 |

Figure 13:
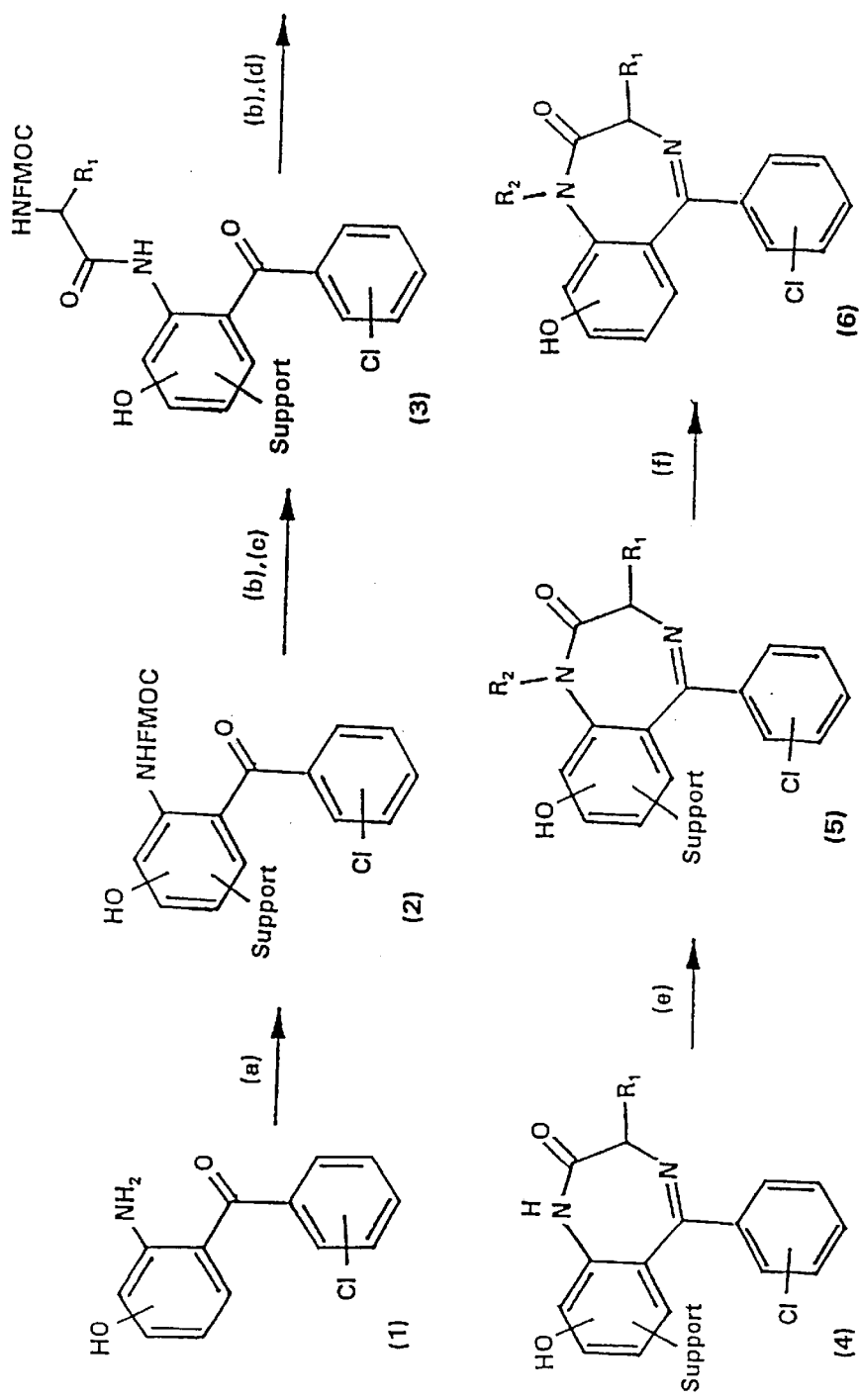
FIG. 13 is a schematic of the synthesis of the 1,4 benzodiazepine derivatives useful to inhibit antibody•DNA complex formation.

Improved solid-phase synthetic methods for the preparation of a variety of 1,4-benzodiazepine derivatives with very high overall yields have been reported in the literature. See, for example, Bunin and Ellman, *J. Am. Chem. Soc.*, 1992, Vol. 114, pp. 10997–10998. Using these improved methods, the 1,4-benzodiazepines derivatives are constructed on a solid support from three separate components: 2-aminobenzophenones, α-amino acids, and (optionally) alkylating agents, as shown in the reaction scheme of FIG. 13.

Preferred 2-aminobenzophenones include the substituted 2-aminobenzophenones, for example, the halo-, hydroxy-, and halo-hydroxy-substituted 2-aminobenzophenones, such as 4-halo4'-hydroxy-2-aminobenzophenones. A preferred substituted 2-aminobenzophenone is 4chloro-4'-hydroxy-2-aminobenzophenone.

Preferred α-amino acids include the 20 common naturally occurring α-amino acids as well as α-amino acid mimicking structures, such as homophenylalanine, homotyrosine, and thyroxine. A preferred group of α-amino acids may be represented by the formula $H_2N-CH(R^1)-COOH$.

Preferred alkylating agents, which may be represented by the formula $R^2-X$, wherein X is —I, —Br, or —Cl, include both activated and inactivated electrophiles, of which a wide variety are well known in the art. Preferred alkylating agents include the activated electrophiles p-bromobenzyl bromide (i.e., where X is —Br and $R^2$ is p-bromo-benzyl) and t-butyl-bromoacetate (i.e., where X is —Br and $R^2$ is $-CH_2C(=O)O-C(CH_3)_3$).

In the first step of such a synthesis, the 2-aminobenzophenone derivative, (1), is attached to a solid support, such as a polystyrene solid support, through either a hydroxy or carboxylic acid functional group using well known methods and employing an acid-cleavable linker, such as the commercially available [4-(hydroxymethyl)phenoxy]acetic acid, to yield the supported 2-aminobenzophenone, (2). See, for example, R. C. Sheppard and B. J. Williams, *Int. J. Pept. Protein Res.*, 1982, Vol. 20, pp. 451–454. The 2-amino group of the 2-aminobenzophenone is preferably protected prior to reaction with the linking reagent, for example, by reaction with FMOC-Cl (9-fluorenylmethyl chloroformate) to yield the protected amino group 2'-NHFMOC.

In the second step, the protected 2-amino group is deprotected (for example, the -NHFMOC group may be deprotected by treatment with piperidine in dimethylformamide (DMF)), and the unprotected 2-aminobenzophenone is then coupled via an amide linkage to an α-amino acid (the amino group of which has itself been protected, for example, as an -NHFMOC group) to yield the intermediate (3). Standard activation methods used for general solid-phase peptide synthesis may be used (such as the use of carbodiimides and hydroxybentzotriazole or pentafluorophenyl active esters) to facilitate coupling. However, a preferred activation method employs treatment of the 2-aminobenzophenone with a methylene chloride solution of the of α-N-FMOC-amino acid fluoride (i.e., $FMOC-NH-CH(R^1)-C(=O)F$) in the presence of the acid scavenger 4-methyl-2,6-di-tert-butylpyridine yields complete coupling via an amide linkage. This preferred coupling method has been found to be effective even for unreactive aminobenzophenone derivatives, yielding essentially complete coupling for derivatives possessing both 4-chloro and 3-carboxy deactivating substituents.

In the third step, the protected amino group (which originated with the amino acid) is first deprotected (for example, -NHFMOC may be converted to $-NH_2$ with piperidine in DMF), and the deprotected compound is reacted with acid, for example, 5% acetic acid in DMF at 60° C., to yield the supported 1,4-benzodiazepine derivative, (4). Complete cyclization has been reported using this method for a variety of 2-aminobenzophenone derivatives with widely differing steric and electronic properties.

In an optional fourth step, the 1,4-benzodiazepine derivative may alkylated, by reaction with a suitable alkylating agent and a base, to yield the supported fully derivatized 1,4-benzodiazepine, (5). Standard alkylation methods, for example, an excess of a strong base such as LDA (lithium diisopropylamide) or NaH, may be used; however, such methods may result in undesired deprotonation of other acidic functionalities and over-alkylation. Preferred bases, which may prevent over-alkylation of the benzodiazepine derivatives (for example, those with ester and carbamate functionalities), are those which are basic enough to completely deprotonate the anilide functional group, but not basic enough to deprotonate amide, carbamate or ester functional groups. An example of such a base is lithiated 5-(phenylmethyl)-2-oxazolidinone, which may be reacted with the 1,4-benzodiazepine in tetrahydrofuran (THF) at –78° C. Following deprotonation, a suitable alkylating agent, as described above, is added.

In the final step, the fully derivatized 1,4-benzodiazepine, (6), is cleaved from the solid support. This may be achieved (along with concomitant removal of acid-labile protecting groups), for example, by exposure to a suitable acid, such as a mixture of trifluoroacetic acid, water, and dimethylsulfide (85:5:10, by volume).

Accordingly, this invention further provides a method of preventing or treating disorders associated with formation of DNA•anti-DNA complexes in an individual by administering to the individual an effective amount of a benzodiazepine from the class identified above to prevent or treat the disorder One of skill in the art can determine when such a pathology is prevented or treated by kidney tissue biopsy or suitable clinical chemical test such as urine protein concentration.

As used herein, the term "administering" means providing the individual with an effective amount of the agent or benzodiazepine derivative effective to inhibit complex formation. Methods of administering pharmaceutical compositions are well known to those of skill in the art and include, but are not limited to, microinjection, intravenous or parenteral administration. The compositions are intended for systemic or local administration as well as intravenously, subcutaneously, or intramuscularly. Administration can be effected continuously or intermittently throughout the course of treatment. Methods of determining the most effective means and dosage of administration are well known to those of skill in the art and will vary the condition of the individual, including age weight and general health. Single or multiple administrations can be carried out with the dose level and pattern being selected by the treating physician. For example, the compositions can be administered prior to a individual already suffering from an inflammatory disease or condition. In this situation, an effective "therapeutic amount" of the composition is administered to prevent or at least inhibit partially kidney damage.

However, the compositions can be administered to subjects or individuals susceptible to or at risk of developing severe glomerulonephritis (which can be predicted by the appearance of complex in the patient's serum) to prevent further complex formation and disease progression. In these embodiments, a "prophylactically effective amount" of the composition is administered.

The compositions of this invention also can be used in immune tolerance therapy. As used herein "immune tolerance" is a permanent form of immune suppression which keeps individuals from reacting with their own tissues. A failure of this mechanism is the cause of SLE. Thus, if one can re-establish this immune suppression, the disease can be effectively reversed. The use of the DNA ligands to the antibodies or the binding site of the anti-idiotypic antibodies of this invention can be used to reestablish immune tolerance. The DNA ligand or binding sites can be administered alone or conjugated to a carrier as describe in U.S. Pat. No. 5,276,013. A method of treating SLE in an affected individual comprises administering a therapeutically effective amount of the antibody or conjugate described above.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

EXPERIMENT NO. I

Generation and Characterization of a Panel of Anti-DNA Antibodies

Monoclonal Antibody Preparation

A single unmanipulated 8-week-old female MRL-Ipr mouse was obtained from Jackson Laboratories (Bar Harbor, Me.) and housed in the University of Michigan Unit for Laboratory Animal Medicine in a pathogen-free environment. Serum samples were screened by ELISA (infra) every four weeks for the presence of anti-DNA, until the titer showed high levels of both anti-ssDNA and anti-dsDNA. The mouse was sacrificed by $CO_2$ asphyxiation at 26-weeks of age and the spleen removed. Spleen cells were fused with nonsecreting myeloma Sp2/O cells in a 5:1 ratio in PBS containing 15% DMSO and 42% PEG 4000 at 37° C. for 30 seconds (23). The solution was slowly diluted with serum free media followed by addition of unstimulated peritoneal cells in HAT media and seeded in 96-well microtiter plates. After 21 days, 620 viable hybridomas were observed (65% of 960 starting wells) of which 137 reacted with heat denatured calf thymus DNA. These hybridomas were subcloned by limiting dilution and reassayed for anti-DNA reactivity. Several hybridomas died and others stopped producing antibody during this time (presumably due to gradual chromosome loss and segregation of the genes required for antibody synthesis; 24) leaving eleven viable cell lines. The isotype of the anti-DNA produced by each hybridoma was determined using an isotyping kit (Boehringer Mannheim, Indianapolis, Ind.) according to the manufacturer's instructions. All of these anti-DNA possess κ light chains.

Large quantities of monoclonal antibodies ("mAb's") for characterization were produced in ascites by interperitoneal injection of $\sim 10^7$ hybridoma cells into pristane-primed retired female BALB/c breeders. Ascites fluid was clarified by centrifugation and then chromatographed over protein A-agarose (Pierce, Rockford, Ill.) at 4° C. using the ImmunoPure buffer system (Pierce) according to manufacturer's specifications. Eluted immunoglobulin was exchanged into DNA binding buffer (50 mM $K_2HPO_4$, pH 8, 150 mM NaCl, 1 mM EDTA) using Centricon 30 microconcentrators (Amicon, Beverly, Mass.). The IgG fraction (1–2 mg) was then chromatographed over ssDNA-agarose (GEBCO-BRL, Gaithersburg, Md.; 2 mL bed volume) equilibrated with DNA binding buffer at 4° C. After washing with 10 column volumes of binding buffer (flow rate ~0.15 mL/min), mAb's 4B2, 7B3, 10F4 were eluted with DNA binding buffer containing 2 M NaCl (elution buffer), whereas 8D8, 9F11, 11F8, 15B10, and 15D8 were eluted with a step gradient of urea (to 4M dissolved in elution buffer). Anti-DNA eluted with urea retained full activity as judged by complete retention of purified protein samples on the ssDNA-agarose column. In addition, the affinity of the mAb's (as judged with the gel shift assay; infra) was not altered after repetitive elution with these low concentrations of urea.

Anti-DNA samples were purified to homogeneity by high-performance ion exchange chromatography on DEAE. Briefly, the mAb's were exchanged into Tris buffer (20 mM Tris-HCl, pH 7.5) and about 1–2 mg of protein loaded onto a Protein Pak DEAE 5PW column (Waters, Marlborough, Mass.) equilibrated with Tris buffer at 4° C. The protein was eluted with a linear gradient of Tris buffer (pH 8) containing 1 M NaCl at a flow rate of 1 mL/min. The desired fractions were pooled, concentrated, and exchanged into binding buffer. Protein concentrations were determined using the BCA protein assay reagent (Pierce, Rockford, Ill.) using normal mouse IgG of known concentration as a standard.

F(ab) Preparation

Crude IgG was isolated from clarified ascites fluid by protein A chromatography as described above. Intact IgG was digested with immobilized papain using the ImmunoPure F(ab) preparation kit (Pierce) according to manufacturer's specifications. Isolated F(ab) was exchanged into DNA binding buffer and chromatographed over ssDNA-agarose. F(ab) purified using this strategy was >95% pure by SDS-PAGE. The pI of the F(ab) was determined by comparing to pI markers (Pharmacia, Piscataway, N.J.) on EEF 3–9 gels using the PhastGel system (Pharmacia).

Nucleic Acids

Calf thymus DNA (10 mg; Calbiochem, San Diego, Calif.) was dissolved in Tris buffer (60 mM Tris, pH 8.0, 100 mM NaCl, 2 mM $CaCl_2$, to 10 mL total volume), deproteinized by chloroform/isoamyl alcohol extraction, and precipitated with ethanol. The DNA was then briefly incubated with micrococcal nuclease (40 U/mg DNA) and purified by gel filtration on BioGel A1.5M (BioRad, Hercules, Calif.) according to Stollar (25).

Single-stranded DNA and RNA homopolymers, poly(dA)•poly(dT) and poly(dG)•poly(dC) were purchased from Pharmacia and used without further purification. Oligodeoxyribonucleotides were chemically synthesized and 5' end-labeled with $[\gamma\text{-}^{32}P]$-ATP as previously described (18, 26).

For screening assays employing a small DNA ligand, the oligonucleotide was first conjugated to BSA to facilitate binding to the microtiter plate (27). Briefly, a 21-base-long oligonucleotide that folds into a stem-loop structure was synthesized with a 5'-hexylaminolinker and purified as previously described (18, 26). The hairpin was dissolved in water (0.5 mL) containing 1-ethyl-3-(3-dimethylaminopropyl)carbodiimide (~50 equiv) and the pH was adjusted to 5.0. BSA was then added (0.25 equiv, Boehringer-Mannheim) and the conjugation was allowed to proceed at 23° C. maintaining the pH at 5.0. After 24 hours the reaction was quenched with sodium acetate (3 M, pH 4.5) and the conjugate was exhaustively dialyzed against PBS and used without further purification. The ratio of the $OD_{260/280}$ indicated that about three hairpins are conjugated to each BSA molecule.

ELISA

Immulon II microtiter plates (Dynatec, Chantilly, Va.) were coated with heat denatured calf thymus DNA (100° C. for 12 minutes, then 0° C. for 20 min, 10 μg/mL), hairpin-BSA conjugate (5 μg/mL), or polynucleotides (10 μg/mL) in TBS (10 mM Tris, pH 7.4, 150 mM NaCl) for 18 hours at room temperature (28). To prepare wells containing only dsDNA, wells coated with calf thymus DNA were treated with S1 nuclease (0.2 U/mL) in nuclease buffer (100 mM sodium acetate, pH 4.6, 100 mM NaCl, 0.1 mM mM $ZnCl_2$, 0.043% glycerol) at 37° C. for 2 hours (29). After blocking with PBS containing 3% BSA for 18 hours at room temperature, the wells were washed with PBS containing 0.1% Tween-20 (PBS-Tween). Anti-DNA samples for assay were diluted in PBS containing 1% BSA and 0.05% Tween-20 (PBT), added to the appropriate wells, and incubated for 2 hours at room temperature. After washing with PBS-Tween, goat anti-mouse Ig-alkaline phosphatase conjugate (Boehringer-Mannheim) diluted 1:1000 in PBT was added and incubated for 2 hours. After washing, bound anti-DNA was visualized by the addition of pnitrophenylphosphate (Sigma-104, 1 mg/mL) in $Na_2CO_3$ (100 mM, pH 9.6). The absorption at 405 nm was measured using a microtiter plate reader (Biotek Instruments, Winooski, Vt.).

Reactivity to Sm, Sm/nRNP, SS-A, SS-B, histone, and Scl-70 autoantigens was determined by direct ELISA using a commercially available kit (INCSTAR, Stillwater, Minn.), Briefly, anti-DNA samples (50 μL of 5 μg/mL solutions) were added to wells that were precoated with antigen (as provided by the manufacturer) and incubated for 30 minutes at 25° C. After washing, bound anti-DNA was detected using a goat anti-mouse Ig-alkaline phosphatase conjugate and visualized by addition of p-nitrophenylphosphate as described above. Positive controls provided by the manufacturer were run in parallel.

Binding to cardiolipin (CL; Fluka, Ronkonkoma, N.Y.), fibronectin (FN; Fluka), laminin (Lam; ICN, Costa Mesa, Calif.), heparin sulfate (HS; Fluka), phosphatidyl serine (PS; Fluka), and collagen type IV (ColIV; Fluka) was assessed by direct ELISA. Briefly, solutions of CL, PS in ethanol (100 μL of 50 μg/mL solutions) were added to Immulon II microtiter plates and evaporated over 18 hours at 25° C. (30). Lam, ColIV, HS (50 μL of solutions that are 2 μg/mL, 5 μg/mL, and 50 μg/mL, respectively, in PBS) and FN (50 μL of a 10 μg/mL solution in 0.1 M sodium carbonate, pH 9.6) were coated 18 hours at 25° C. (31–34). After blocking with PBS containing 3% BSA, anti-DNA (50 μL of 5 μg/mL solutions) were incubated with the antigens for 2 h at 25° C. Bound antibody was detected as described above.

Gel Shift Assay and DNA Footprinting

Anti-DNA affinity for oligonucleotide ligands was measured by gel shift assay as described by Stevens et al. (35) except that the sodium ion concentration was adjusted with NaCl (to 150 mM). The number of cations released upon DNA binding was assessed by performing a series of binding titrations as a function of sodium ion concentration. Footprinting with $KMnO_4$, diethyl-pyrocarbonate (DEPC), dimethyl sulfate (DMS) was performed as previously described by Swanson etal. (18).

Fluorescence Quenching Studies

Fluorescence measurements were performed on a Perkin-Elmer LS-50 luminescence spectrometer equipped with a thermostated cell block maintained at 23° C. All measurements were carried out in phosphate buffer (50 mM $K_2HPO_4$, pH 8.0, 150 mM NaCl, 1 mM EdTA) following the procedures described by Kelly et al. (36) and Kim et al. (37). Briefly, solutions of monoclonal antibody (~1 μM) were excited at 278 or 295 nm and the emission spectra was monitored for changes in fluorescence as a function of varying DNA ligand concentration. To minimize inner filter effects, the optical density at 295 nm was kept under 0.1 AU. The binding site size was approximated by measuring the number of molar equivalents of nucleotide necessary to achieve complete saturation of the binding sites as indicated by fluorescence quenching (36).

EXPERIMENTAL RESULTS

Isolation and Purification of Monoclonal Anti-DNA

A panel of anti-DNA hybridomas was generated from an unmanipulated MPL-Ipr mouse for the presence of antibodies that bind to the ssDNA regions on heat denatured calf thymus DNA and to the dsDNA epitopes present on native calf thymus DNA. Positive clones also was screened against a DNA hairpin stem-loop construct to determine (a) the frequency with which small DNA ligands are bound by anti-DNA and (b) the extent to which the single stranded and double stranded regions on hairpins can model the ssDNA and dsDNA epitopes recognized by anti-DNA (18, 35). Indeed, greater than 85% of anti-DNA reactive with either ssDNA or dsDNA recognized the hairpin construct by ELISA, suggesting that small oligonucleotide constructs can model epitopes on ssDNA and dsDNA ligands. Those that do not bind the hairpin construct either prefer a different sequence or may bind weakly, requiring longer antigens for multivalent recognition (avidity). Application of this hairpin ligand in other binding experiments is described later.

Purification of large quantities of mAb's from endogenous Ig present in ascites fluid was achieved by affinity chromatography on protein A-agarose followed by affinity chromatography using an ssDNA-agarose column. Additional purification of each mAb by preparative ionexchange chromatography on a DEAE matrix afforded samples >98% pure as judged by analytical ion exchange chromatography and SDS-PAGE (FIG. 1). Each mAb is more acidic than the corresponding F(ab) fragments and the pI values of the IgG2a F(ab)'s are generally higher than those generated from the IgG3 or IgG2b mAb's. Moreover, F(ab)'s generated from these anti-DNA hybridomas that bind dsDNA (IOF4 and 4B2, IgG2a) possess higher pI values than all of the other anti-DNA. These observations suggest the IgG2a mAb's may possess a greater number of cationic residues than the other anti-ssDNA in this panel and is consistent with binding data suggesting that DNA recognition by the IgG2a mAb's involves more electrostatic interactions than the other anti-ssDNA (infra).

Specificity of Monoclonal Anti-DNA

While monoclonal antibodies generally do not crossreact with many different antigens, the reactivity of anti-DNA mAb's can be wider, including recognition of both cellular and nuclear antigens (39, 40). Precisely defining anti-DNA specificity is important because recognition of antigens other than DNA may be involved in both the evolution of anti-DNA and their pathogenicity in vivo (40–45). Although there have been several studies addressing this issue, there is conflicting evidence on the nature and extent of anti-DNA crossreactivity (6, 30, 42, 43, 45, 46–48). To help determine the extent to which crossreactivity is a feature of anti-DNA recognition, the ability of this panel of mAb's to bind antigens identified previously as having crossreactive epitopes (30–34) was assessed. These molecules include nuclear proteins, ribonucleoproteins, phospholipids, proteoglycans, and extracellular matrix components normally present within normal glomerular basement membrane. As shown in Table I, only 7B3 shows crossreactivity to any of these antigens. These data support recent studies (30, 45, 46) suggesting the specificity of anti-DNA may be narrower than has been described (31, 33, 42, 43, 47).

To gain a better understanding of the specificity that these anti-DNA display toward nucleic acid ligands, their reactivity toward several different polynucleotides was assessed. The data indicate that each mAb strongly reacts with poly (dT) which is consistent with previous observations that poly(dT) contains immunodominant epitopes (Table 2) (1, 19, 20, 49). Several mAb's, including 9F11, 15B10, 15D8 and 11F8 only recognize poly(dT) whereas the others bind one or more of the other polydeoxyribonucleotides. In contrast, none of the mAb's bind significantly to polyribonucleotides, a result also consistent with previous studies (1, 20, 49). These findings may either suggest that anti-DNA can discriminate between the two different sugar moieties, or that more complicated secondary or tertiary structures exist in these polymers that limit access to the nucleotide bases in RNA relative to DNA (50). Given that these anti-DNA bind oligo(dU), the latter alternative seems more likely (infra).

Relative Affinity of Anti-DNA for Oligonucleotide Ligands

Although the initial direct ELISA experiments reveal some information about the specificity of these anti-DNA, they do not provide a reliable assessment of the relative differences in affinity between different anti-DNA (51, 52). To address this point, binding to small DNA oligomers was assessed using a gel shift assay which directly measures binding in solution at equilibrium (53). Twenty-one (21)-base-long oligomers were selected for the test antigens because they are long enough to retain the features of polymeric DNA (i.e., they should contain at least one epitope for binding), but too short to be bridged by both antibody combining sites simultaneously thereby avoiding the possibility of artifacts caused by avidity. The reactivity patterns determined by ELISA generally reflect the gel shift data (Table 3). Specifically, all mAb's have the highest relative affinity for $dT_{21}$, regardless of isotype. However, the relative affinity for $dT_{21}$ varies with the isotype, with IgG2b mAb's having the highest affinity. $dA_{21}$ is not recognized by any of mAb's on this panel, and the affinity toward either $dG_{15}$ or $dC_{21}$ varies among the different antibodies, especially in the IgG2a subclass. Although the IgG2b and IgG3 anti-DNA do not bind to poly(dI) by ELISA, the gel shift data clearly show that the order of base specificity for the IgG2b and IgG3 mAb's is $dT >> dG >> dC \geq dA$.

Other groups have observed similar trends in the specificity of monoclonal anti-DNA. For example, Tetin et al. using fluorescence quenching experiments find that BV04-01 (IgG2b, κ) binds $dT_6$ with about 5 times greater affinity than $dG_6$ ($K_d$=0.13 vs 0.71 μM, respectively) and does not exhibit appreciable affinity for either $dC_6$ or $dA_6$ (54). Similarly, Lee reported that an F(ab) fragment of HEd10 (IgG2a, κ) displays much higher affinity toward oligo(dT) than either oligo(dC) or oligo(dA) ($K_d$=80 nM vs >2 μM, respectively) (20). Both BV04-01 and HEd10 are derived from (NZBxNZW)$F_1$ mice. The data presented here suggest these trends are also representative of anti-DNA derived from MRL-lpr mice and is consistent with variable region sequence analysis demonstrating a high degree of homology between anti-DNA generated from different mouse strains (14, 15).

Figure 2:
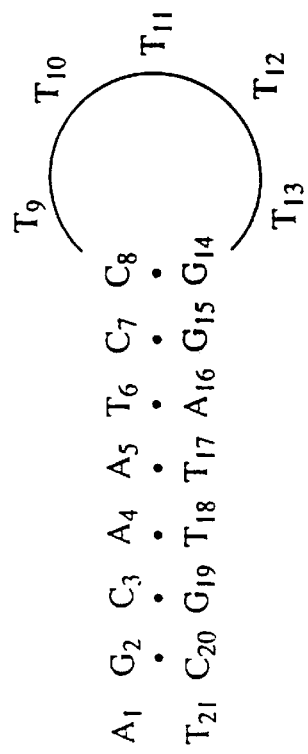
FIG. 2 shows the sequence of model DNA ligands (SEQ ID NOS: 1–4). The synthesis of these sequences has been described previously (18, 26, 35). Incorporation of disulfide crosslinks into these ligands increases their thermodynamic stability without disrupting the native geometry of the structure (26, 55).

In addition to single-stranded homopolymers, anti-DNA affinity for dsDNA was assessed with a disulfide cross-linked dodecamer (1, FIG. 2). This ligand was chosen because (a) high resolution structural information is available for this sequence (56), (b) the short length of the sequence precludes binding by both antigen binding sites simultaneously, and (c) the disulfide cross-links prevents terminal fraying and keeps the duplex from adopting alternate conformations without compromising the native helical geometry (26). These latter two points are particularly important since alternate conformations may present a variety of it "complex" epitopes, including regions of ssDNA. Although these anti-DNA may possess sequence selectivity and hence may not bind duplex optimally, this sequence nevertheless provides the basic geometric requirements of B-DNA and is therefore a good starting point with which to examine the binding properties of anti-dsDNA. The data in Table 3 indicate that only two of the IgG2a anti-DNA, 4B2 and 10F4, have an appreciable affinity for dsDNA. Interestingly, these anti-DNA also bind $dT_{21}$, although the relative affinity for ssDNA is much weaker than seen with the IgG2b anti-DNA.

Figure 3:
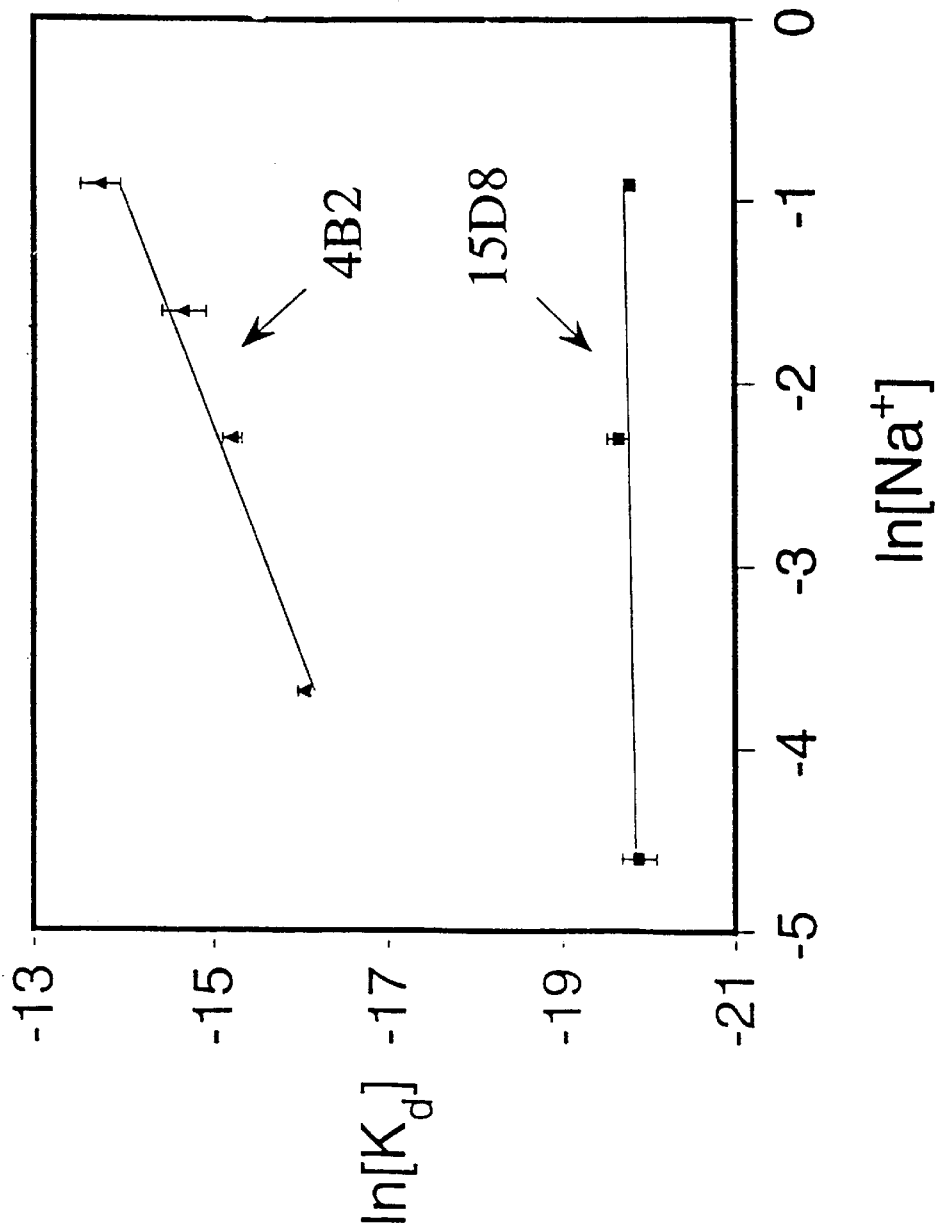
FIG. 3 shows cation release in anti-DNA complexes with $dT_{21}$. The apparent dissociation constant ($K_d$) was measured as a function of sodium ion concentration as described in the experimental section below. The number of released cations was calculated by solving the equation $\ln[K_d]=Z\psi\ln[Na+]+\ln[K°]$ for Z using a value of 0.71 for $\psi$ and the slope derived from a plot of $\ln[K_d]$ vs $\ln[Na+]$ (58). Plots of $\ln[K_d]$ vs $\ln[Na+]$ are shown for 15D8 ($Z\psi=0.04$, r=0.54) and 4B2 ($Z\psi=0.79$, r=0.98) and are representative of anti-DNA that release zero (IgG2b mAb's and 11F8) or one cation (IgG2a mAb's), respectively, in complexes with $dT_{21}$. Similar results were obtained using $dT_5$ with 9F11 and 11F8, however, binding by the IgG2a mAb's was too weak to measure so this analysis could not be performed.

To address the contribution of ion pair formation in stabilizing anti-DNA-DNA complexes, a gel shift assay was employed to measure $K_d$ values for each mAb as a function of [Na+]. Plotting the ln[$K_d$] against ln[Na+] should afford a line whose slope represents the number of sodium cations released upon binding (57, 58). Assuming that the released cations were originally bound to the phosphates on DNA, and neglecting anion effects, the number of released cations represent the number of phosphates that have exchanged a sodium ion for a positively charged residue on the antibody (59). Binding of $dT_{21}$ by the IgG2b mAb's (e.g. 15D8) and by 11F8 is not accompanied by release of bound cations, whereas the other IgG2a mAb's (e.g., 4B2) appear to release one cation upon complex formation (FIG. 3). These data suggest that recognition of $dT_{21}$ does not involve ion pair formation for the IgG2b and IgG3 mAb's, whereas the IgG2a anti-DNA may form one salt bridge upon binding. This observation is in general agreement with studies of other anti-ssDNA. For example, Lee and coworkers have found that two phosphates may form ion pairs in the complex between an F(ab) fragment of HEd10 and poly (dT), whereas only one ion pair is observed in BV04-01-ssDNA complexes (17–20). Thus, it seems that electrostatic interactions play a relatively minor role in recognition of ssDNA.

The affinity of 4B2 for the cross-linked duplex as a function of sodium ion concentration also was measured. The data suggest one cation is released upon formation of the 4B2-dsDNA complex, which is also the same number observed in the binding of 4B2 to $dT_{21}$. Similar analysis could not be performed for mAb 10F4 because at high [Na+], binding was too weak to measure. The cation release observed for 4B2 suggests that the molecular interactions which mediate binding of both ssDNA and dsDNA by this mAb may not be just electrostatic. Although the presence of cationic residues like lysine and arginine in antiDNA (HCDR3 in particular) may be associated with the greater affinity for dsDNA (60), they are not necessarily indicative of ion pair formation. Indeed, cationic residues are also involved in hydrogen bonding, van der Waals contacts, and stabilizing CDR architectures through inter- and intra-chain hydrogen bonds and salt bridges (17, 61, 62).

Fluorescence Measurements, Binding Site Size, and Intrinsic Affinity

Figure 4A:
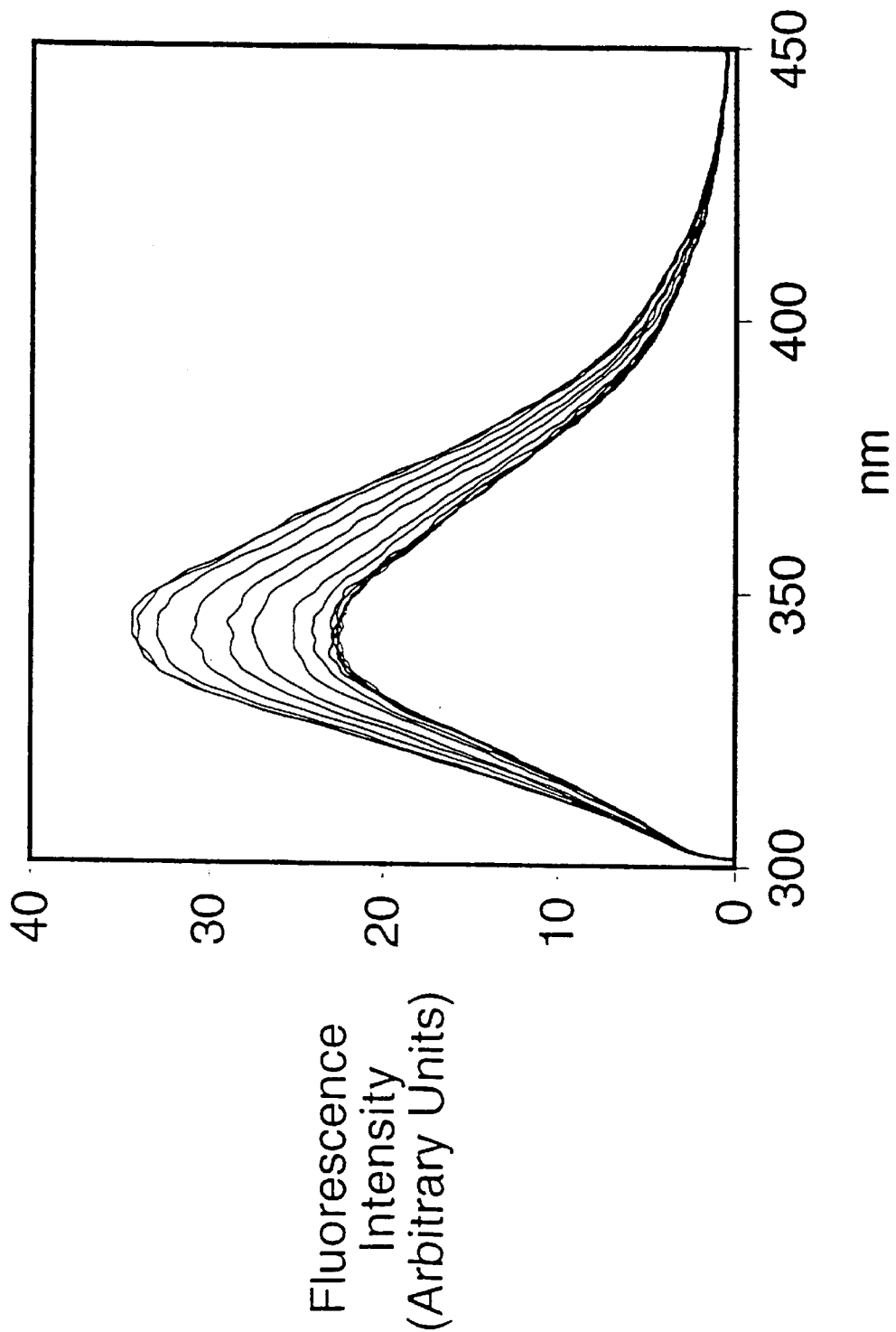
FIGS. 4A and 4B are representative fluorescence quenching titration of anti-DNA with poly(dT).
Figure 4B:
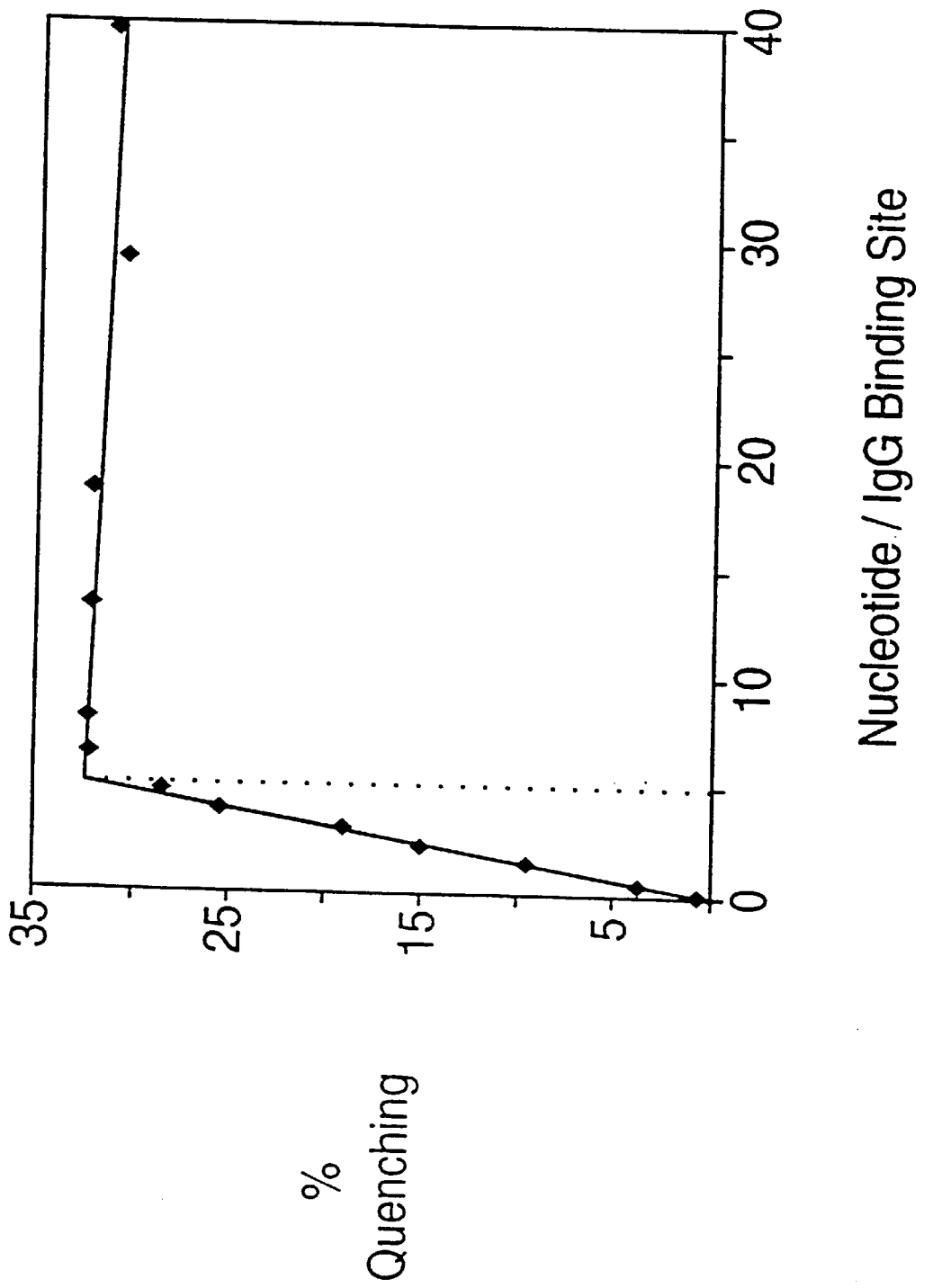

DNA recognition can result in the quenching of the intrinsic fluorescence of tryptophan and/or tyrosine in DNA binding proteins (36, 37). In anti-DNA, these phenomena have been attributed to changes in microenvironment upon ligand binding and reflects a static mechanism of quenching (54). Studies by both Tetin et al. (54) and Lee et al. (20) show anti-ssDNA undergo fluorescence quenching in the presence of ssDNA ligands. Each of the mAb's of this panel display fluorescence quenching when titrated with poly(dT) (FIG. 4). This effect is observed at excitation wavelengths of either 278 nm or 295 nm, implicating tryptophans, and perhaps tyrosines in DNA binding (37). In control experiments using poly(dA), fluorescence quenching of these anti-DNA is not observed, indicating that complex formation is required for this effect. Also, when normal mouse IgG is titrated with poly(dT), no quenching is found which indicates that nonspecific binding is not responsible for changes in the fluorescence intensity. Lastly, the other DNA homopolymers do not induce fluorescence quenching when titrated with these mAb's. These results suggest that the other DNA polymers may not be bound in the same manner as poly(dT) and that the difference in affinity may be reflected in these different modes of recognition.

The number of consecutive nucleotides occluded upon binding (i.e., epitope size) has been determined for several single-stranded DNA binding proteins using fluorescence quenching methods (36, 37). This analysis is possible if the affinity for a polynucleotide is sufficiently high to approximate a linear reduction in fluorescence intensity as a function of nucleotide concentration. After a stoichiometric amount of ligand is added, all of the available binding protein binding sites are saturated and titrating with additional ligand has no effect on the protein fluorescence. Performing this experiment with this panel of mAb's using poly(dT) as the ligand reveals that about five nucleotides are occluded upon binding (FIG. 4). These data are in general agreement with the site size determined for both BV04-01 and HEd10 (17, 20).

Figure 5:
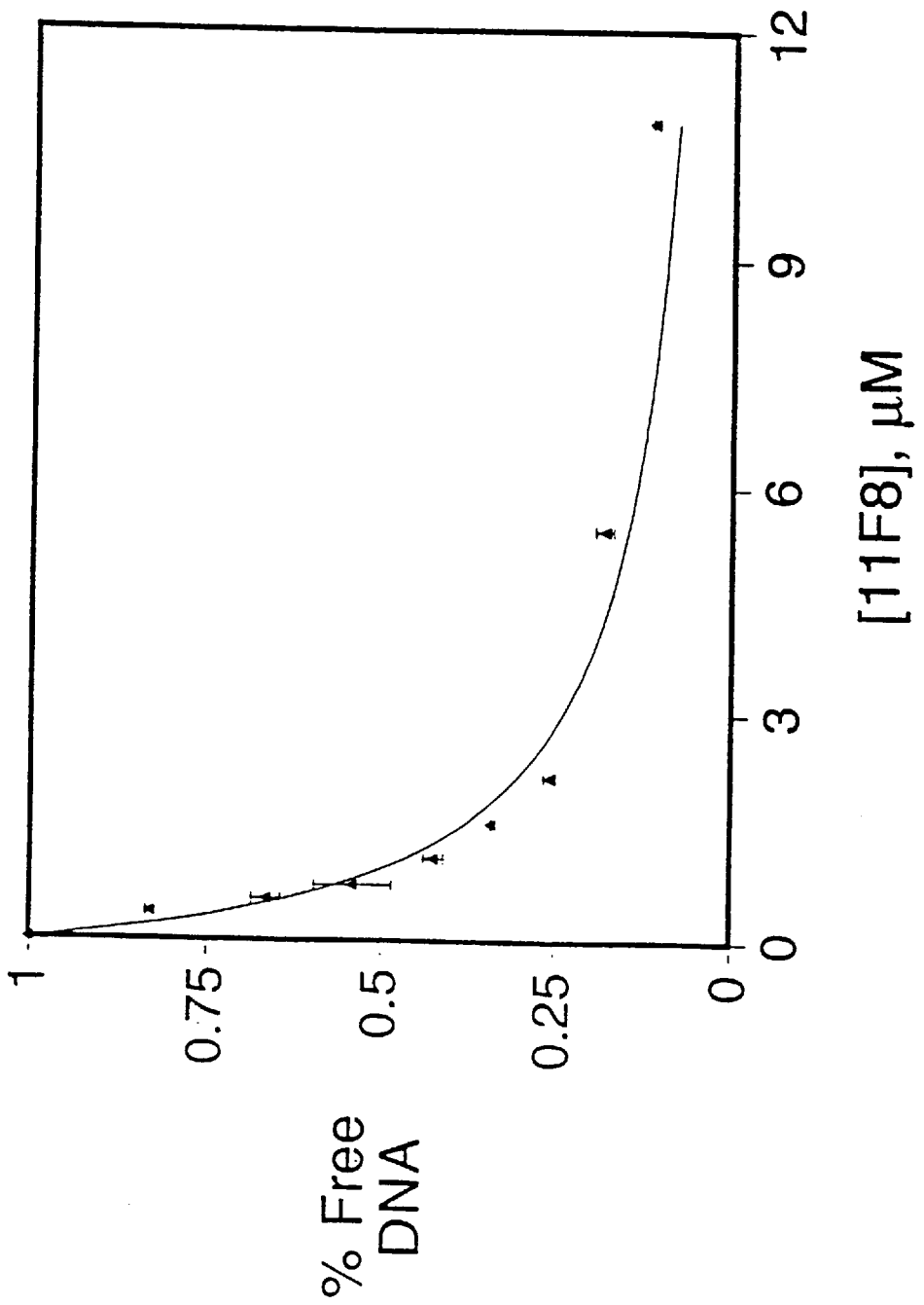
FIG. 5 is a representative gel shift binding isotherm. Each data point represents the average from three different binding titrations. These data were fit by non-linear least squares regression to a single-site binding isotherm and afford a $K_d$ of 939±81 nM ($X^2=0.02$).
Figure 6A:
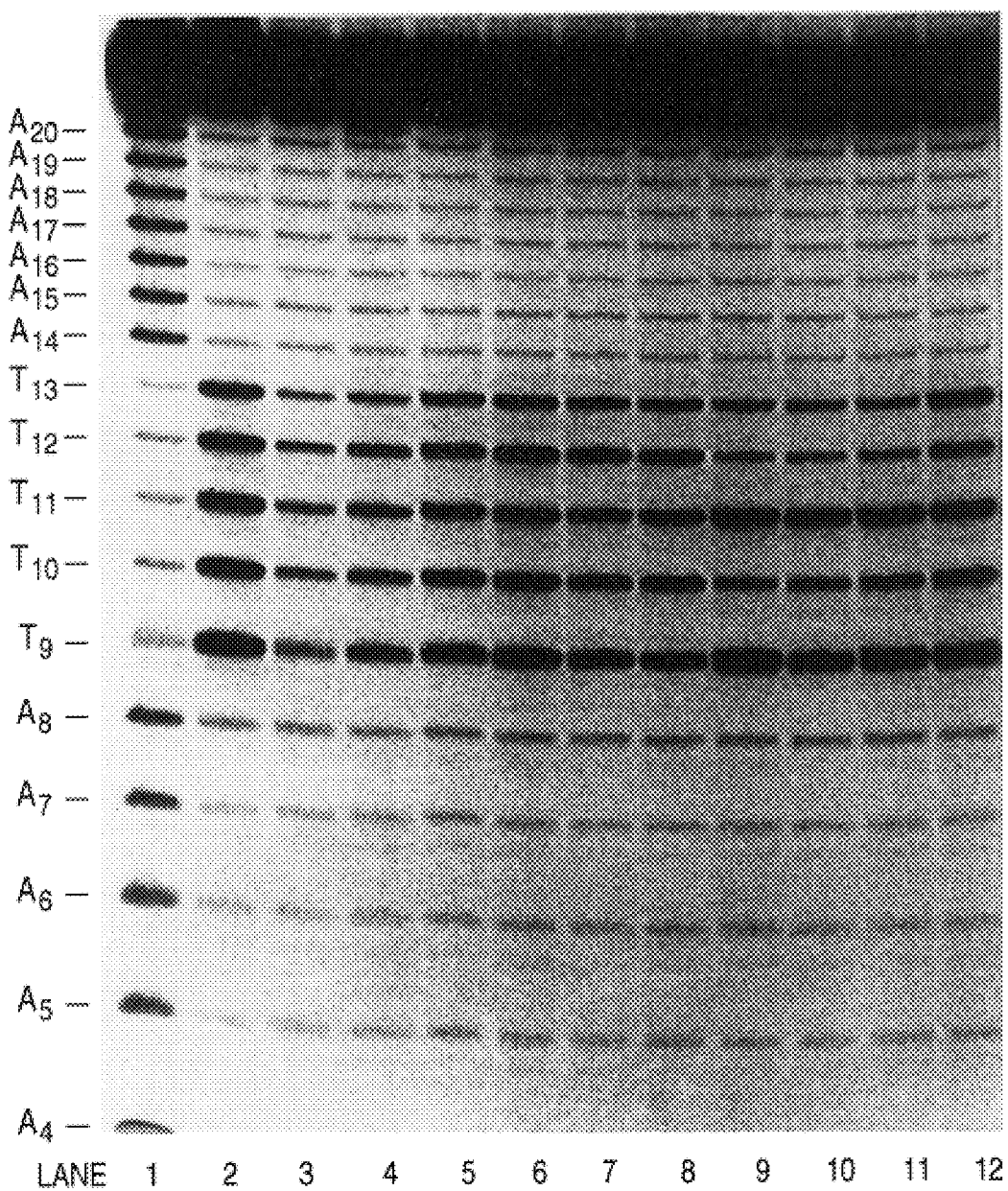
FIGS. 6A to 6C are potassium permanganate footprinting of the anti-DNA panel. Anti-DNA or normal mouse IgG (nIgG) (10–20 µM) was complexed to ligand 2 (0.5 nM), reacted with KMnO$_4$ for 30 s, and treated as previously described (18). Equivalent amounts of DNA (as judged by liquid scintillation counting of samples) were applied to the sequencing gel.
Figure 6B:
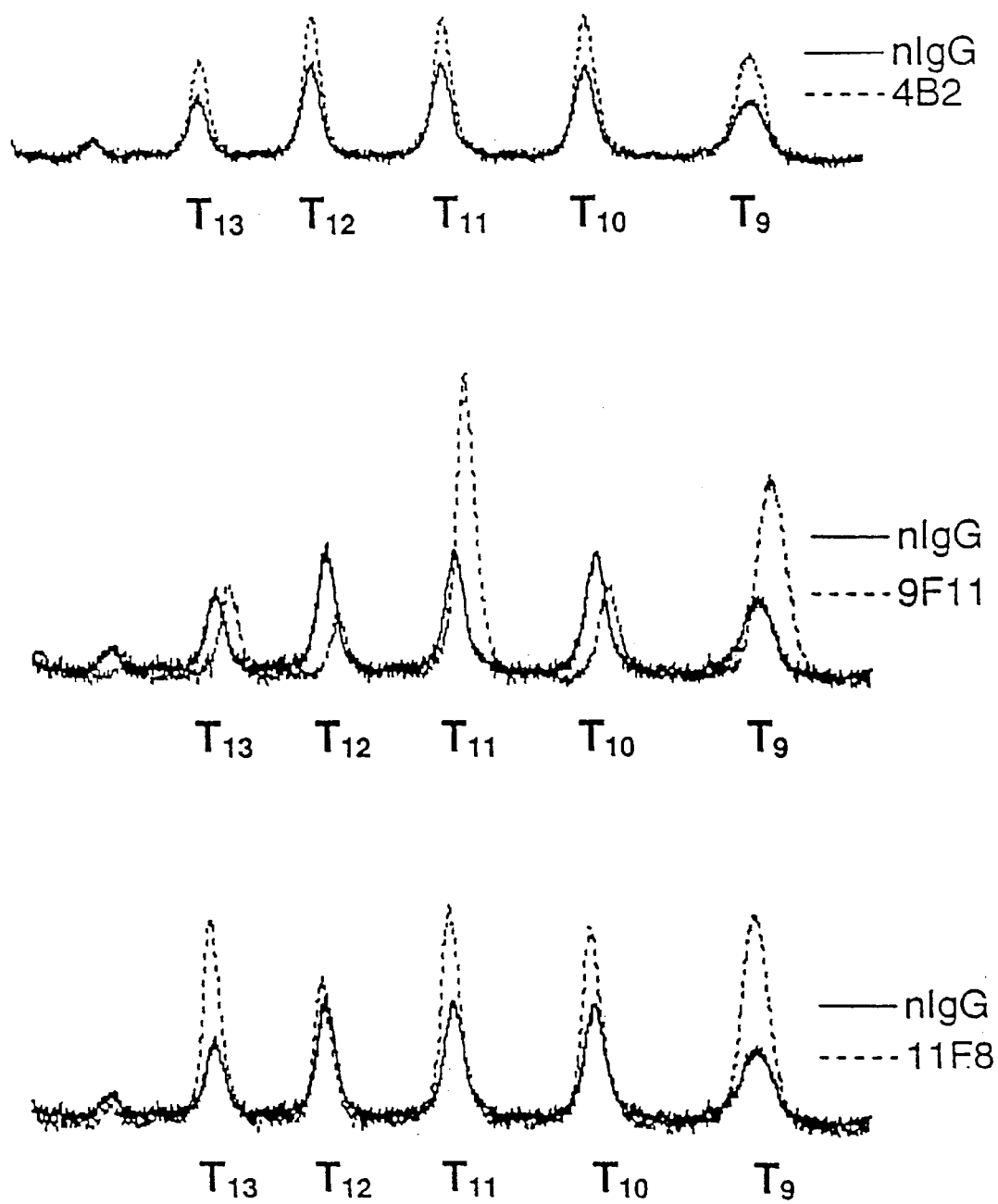
Figure 6C:
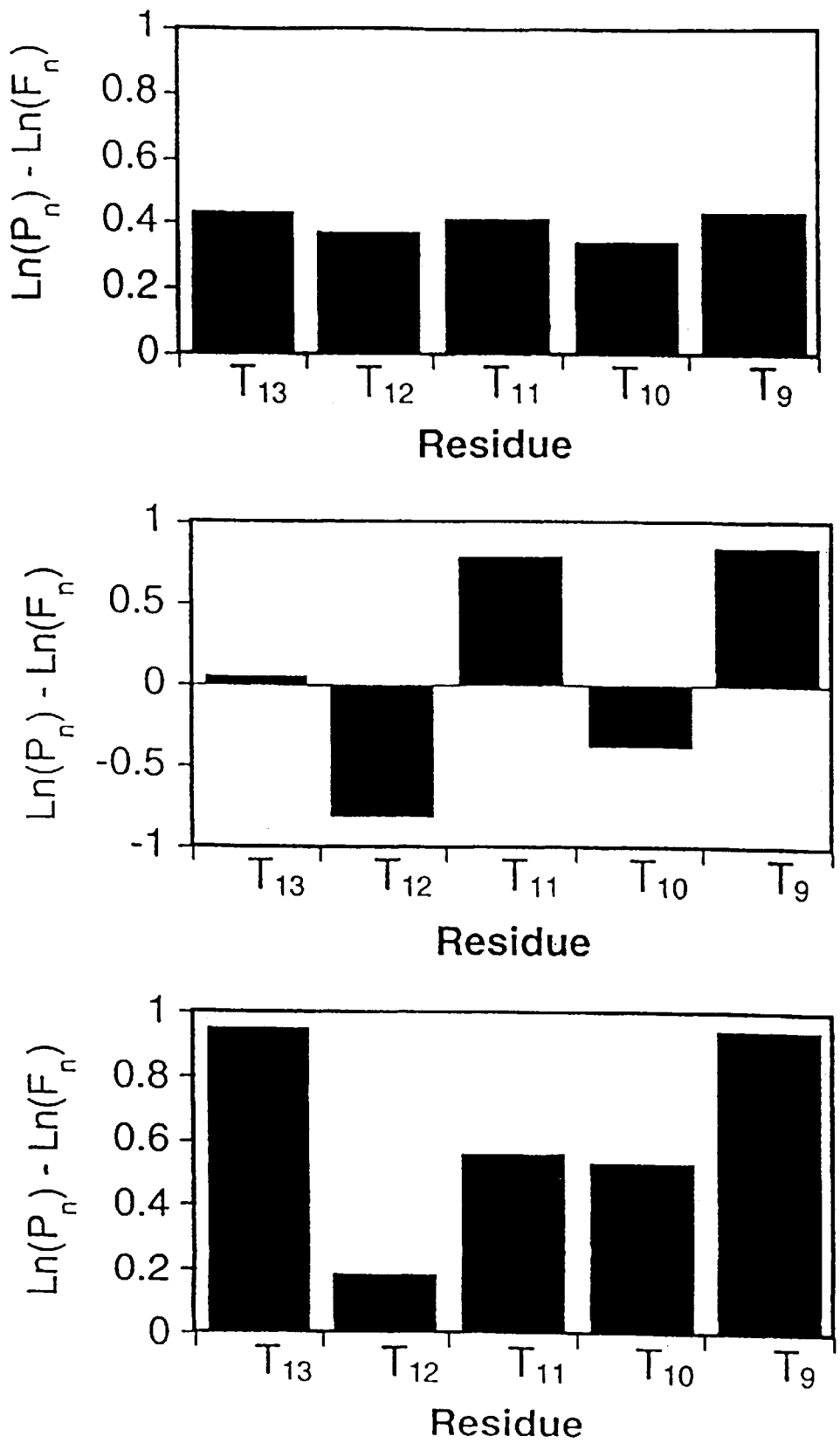
Figure 10A:
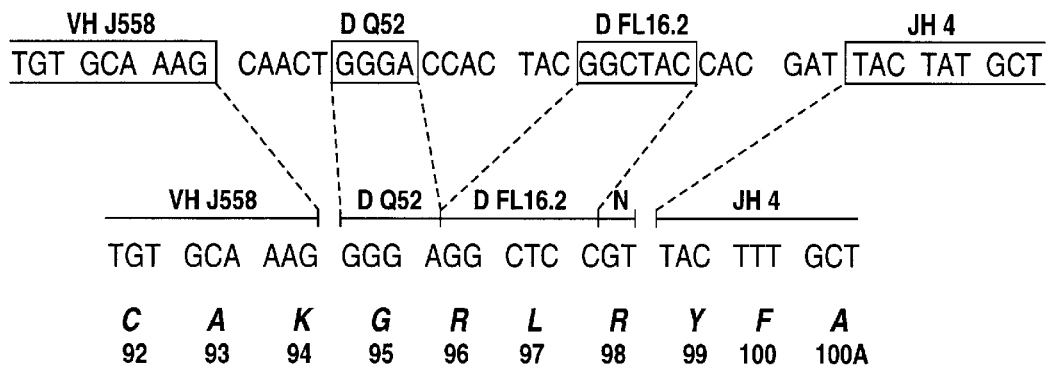
FIGS. 10A (SEQ ID NOS: 77–93) and 10B (SEQ ID NOS: 94–105) show V(D)J construction in CDR3. HCDR3 (FIG. 10A) and LCDR3 (FIG. 10B) are displayed according to Radic and Weigert (15). The parent gene fragment from which the functional CDR3 is derived is provided above the sequence. The boxed sequence represents the portion of the germline gene incorporated into the CDR3 construct. Positions that have mutated away from the putative germline gene are highlighted in boldface. Nontemplate-derived sequences are indicated by N.
Figure 10A:
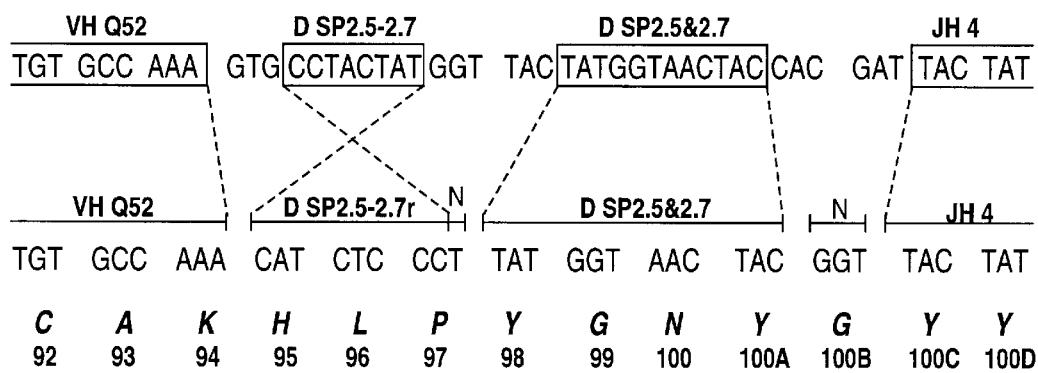
Figure 10A:
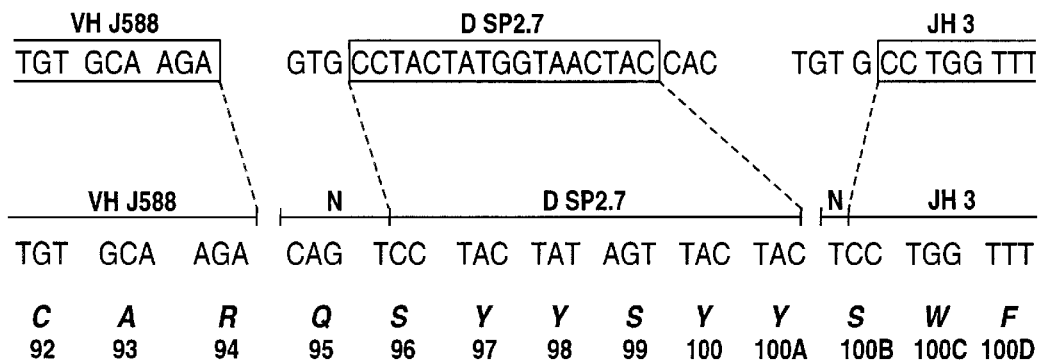
Figure 10B:
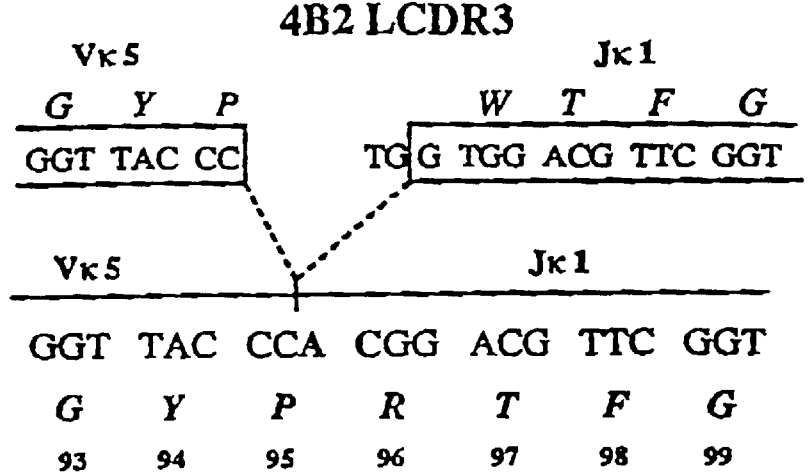
Figure 10B:
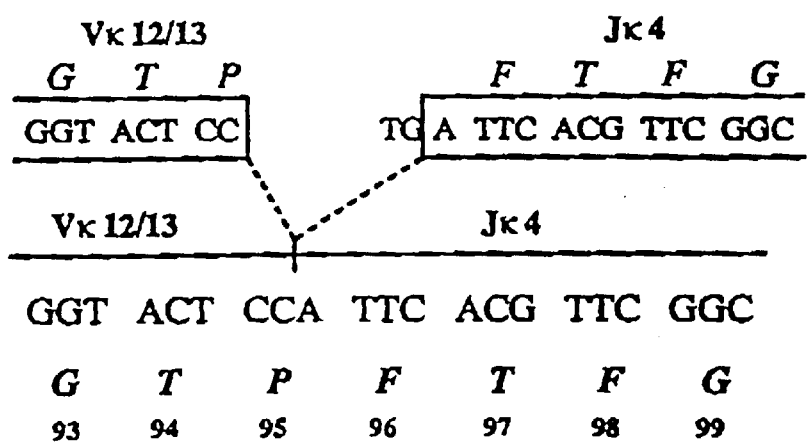
Figure 10B:
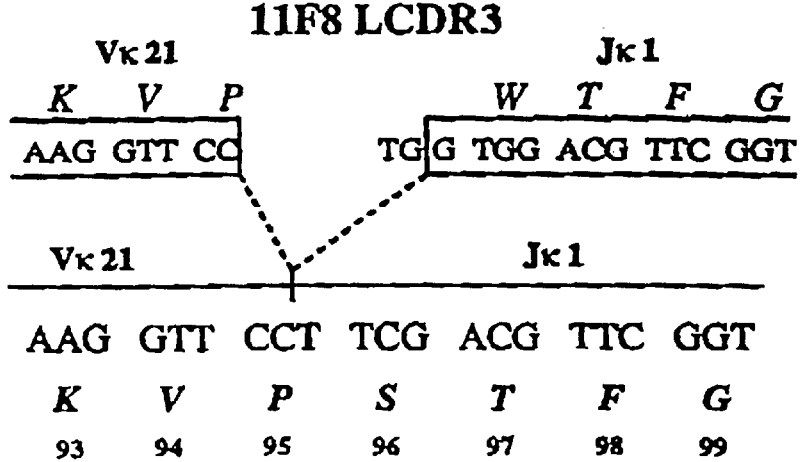

Because the fluorescence quenching experiments suggest that the epitope size of this panel mAb's is about five nucleotides long, determining the "intrinsic" affinity for a DNA ligand that just fills the binding site was next determined. The intrinsic affinity of the mAb's of this panel for $dT_5$, $dG_5$ and $dC_5$ was measured using the gel shift assay. A representative equilibrium binding isotherm is shown in FIG. 5. Significant binding is only observed with $dT_5$ and only for about half of the mAb's (Table 4). One important finding is that the intrinsic affinity for $dT_5$ is lower than the apparent affinity observed for $dT_{21}$ which suggests that the apparent affinity for dT21 (and all the polymer ligands) is largely derived from additivity effects resulting from the presence of multiple overlapping binding sites (36). While this observation is not surprising, one implication of these results is that the binding data obtained using high molecular weight nucleic acid polymers does not reflect the intrinsic affinity for a single binding site on the ligand and may complicate affinity/specificity analysis.

To examine the contribution of the C5-methyl group of thymine in stabilizing anti-DNA-oligo(dT) complexes, the deoxyuridine analogs of the thymidylate ligands was synthesized and binding titrations were performed using the gel shift assay and fluorescence spectroscopy (Table 4). The fluorescence spectra of anti-DNA of this panel are quenched by the addition of oligo(dU), suggesting that the mode of recognition of oligo(dU) is similar to oligo(dT). However, the affinity for dU5 is about 5-fold lower for $dT_5$ for both 9F11 and 11F8. This increased affinity for oligo(dT) relative to oligo(dU) may be explained if the C5 methyl group of thymine is oriented into the antigen binding site where it can participate in favorable van der Waals contacts. Indeed, this hypothesis is consistent with the results of $KMnO_4$ footprinting experiments (infra).

The mode of dsDNA recognition with fluorescence binding titrations was assayed and found that neither poly(dG)-poly(dC), poly(dA)-poly(dT), nor the model dodecamer duplex afford changes in the fluorescence spectra of 4B2. One possibility is that binding occurs at a site other than the antigen binding cleft. However, $dT_{21}$ competes with the duplex in complexes with anti-DNA and vise versa, indicating that both ligands are bound in the same site. Thus, although fluorescence quenching is observed upon titration with poly(dT), binding of dsDNA has no effect on the fluorescing chromophore. This observation, though indirect, indicates that for this mAb, the mode of binding dsDNA is different from the manner of ssDNA recognition. Quenching of the chromophore in ssDNA binding may involve direct contact with ligand or conformational changes in the antigen binding site associated with complexation that alters the microenvironment of chromophore (54). Binding dsDNA may utilize a different set of residues (14, 15) or require less movement to accommodate the ligand.

By measuring the helix-coil transition of poly(dA)-poly(dT) in the presence of different concentrations of anti-dsDNA Jel241, Braun and Lee estimated that this mAb recognizes about six base pairs, which is consistent both with the dimensions of the known antibody combining site size and the binding site size obtained here for ssDNA ligands (22).

Defining the Autoreactive Epitopes on ssDNA and dsDNA Antigens

Potassium permanganate selectively modifies the C5–C6 double bond of thymine bases that are not Watson-crick hydrogen bonded and can be used to probe the accessibility of this base in protein-DNA complexes, including those with anti-DNA (18). Since each of the mAb's of this panel has a preference for binding poly(dT) and a binding site size of about five nucleotides in length, their interaction with a 21-base-long oligomer containing a central $dT_5$ segment flanked by a nonbinding (dA) sequence was examined to aid in sequencing (oligomer 2, FIG. 2). When compared to normal mouse IgG as a control, the pattern of permanganate reactivity of 2 is marginally increased when complexed to any of the IgG2a mAb's (FIG. 5). However, the reactivity of the thymine bases is quite different when bound by the IgG2b and the IgG3 mAb's. Quantitative measurements of the difference in probability of modification clearly show that in the presence of 9F11 and 11F8 the thymine bases in 2 exhibit both hyperreactivity and reduced reactivity relative to nIgG (18; FIG. 4). Furthermore, the asymmetry of the $KMnO_4$ reactivity pattern suggests that ssDNA is bound with a specific polarity, however, the orientation of the DNA (5' to 3' or 3' to 5') in the antibody binding site cannot be ascertained from these data alone. Those positions that are hypermodified (e.g., $T_{11}$ and $T_9$ for 9F11) may result from a DNA conformation in which the C5–C6 double bond of the base projects away from the binding site where it is exposed to $KMnO_4$ modification. In contrast, if the base is oriented in a pocket so that the C5 methyl groups faces the antigen binding site or the DNA adopts a conformation in the complex that shields the base relative to the free DNA, the C5–C6 double bonds may be rendered less accessible to $KMnO_4$ modification (e.g. $T_{10}$ and $T_{12}$ for 9F11). The minimal increases in permanganate sensitivity seen in DNA ligands bound the IgG2a mAb's coupled with their relatively low affinity suggests that DNA binding may be nonspecific.

Another mechanism used by antibodies for antigen recognition is induced fit (18, 35, 65, 66). For example, it was previously demonstrated by the inventors that concomitant with binding the single-stranded loop in DNA hairpins, anti-ssDNA BV04-01 partially unwinds the adjacent stem duplex (18). To determine if the anti-DNA described here induce conformational changes in DNA ligands, mAb complexes of hairpin 3 were footprinted (FIG. 2) with $KMnO_4$ and sensitivity was examined at sites adjacent to the single-stranded pentathymidine loop. None of the mAb's reported here induce significant structural changes in the duplex region of this hairpin construct. This observation suggests that either the energetic penalty for partially denaturing the duplex is greater than the available binding free energy or that these mAb's do not require conformational changes in the duplex to achieve optimal binding (67). Since the affinity of the 21 IgG2b anti-DNA and BV04-01 for 3 is similar (~0.5 μM) the latter alternative is favored.

Footprinting duplex 1 (FIG. 2) complexed to mAb's 4B2 and 10F4 with $KMnO_4$, DMS, and hydroxyl radical does not result in any detectable pattern of protection or provide evidence of conformational changes in the ligand; similar results were also obtained with longer duplexes, both crosslinked and unmodified (68). The lack of a distinct footprint suggests that either the target of the chemical probes are equally accessible in both the bound and free DNA or that the binding is not specific enough to yield discernible footprints. Because duplex 1 may not be the optimal sequence for binding, the latter alternative may be more likely (it may also be possible that anti-DNA are not sequence selective DNA binding proteins). In support of this hypothesis, La Baer and Yamamoto reported that while the relative affinity of the glucocorticoid receptor for its consensus binding sequence containing a single base-pair substitution is reduced only five-fold relative to the wild-type sequence, the footprint generated by copper phenanthroline is abolished (69).

DISCUSSION

Antibodies that bind ssDNA constitute the largest population of anti-DNA (1) and their reactivity and mode of ligand recognition is better understood than anti-dsDNA (16). Most of what is known about the mechanism of anti-ssDNA binding is based on the crystal structure of anti-ssDNA BV04-01 complexed to d(pT3), along with models of BV04-01-DNA complexes based on binding/footprinting studies (17, 18). The results from these experiments have shown that (a) base stacking of thymine between aromatic residues stabilizes binding of ssDNA, (b) ion pair formation is limited, and (c) hydrogen bonding to the phosphate backbone as well as to substituents on the DNA bases are important for binding. Studies of the anti-ssDNA HEd10 by Lee and coworkers support and extend these findings (20). These studies show that tryptophans are involved in binding poly(dT), four consecutive residues are recognized, and two ion pairs may be formed in the complex. Contact to the pyrmdine ring, specifically the 5-methyl, 4-carbonyl, and 3-imino groups, was inferred through affinity measurements to poly(dU), poly[d(brU)] and poly[d(brC)].

The four highest affinity mAb's in this study, 9F11, 15B10, 15D8 and 11F8, comprise one group of anti-ssDNA and share many similarities with both BV04-01 and HEd10. These similarities include specificity for thymidine, limited ion effects, involvement of tryptophans and tyrosines in binding, and a binding site size that is about five nucleotides long. Importantly, $KMnO_4$ footprinting offers clues to common features of recognition in this group of anti-DNA. For example, these experiments show that two thymine bases are protected from $KMnO_4$ modification and two bases are hypermodified by $KMnO_4$ in the presence of 9F11, 15B10 and 15D8, whereas in the presence of 11F8, only one base is protected while the other four are hypermodified. These observations are consistent with a mechanism in which the thymine base is specifically bound in a subsite on the protein surface, possibly sandwiched between two aromatic residues as revealed in X-ray and modeling studies of BV04-01 and predicted for HEd10 (17, 18, 85). The driving force for this mode of recognition is not clear, but since binding is not accompanied by cation release, it may involve hydrophobic effects including van der Waals contacts and the entropic benefit of releasing bound water molecules from the protein surface (86, 87).

Since the pattern of reactivity in 9F11, 15B10 and 15D8 is similar, it is possible that these mAb's are clonally related. The small differences in affinity in these three mAb's may reflect somatic mutations that subtly alter the complementarity of the binding site to the ligand without changing the basic mode of recognition. That 11F8 protects one less base from modification than the other three mAb's may account for the lower affinity to oligo(dT), but the overall mechanism of binding appears conserved among this group of anti-ssDNA. Taken together, these data suggest that "high affinity" anti-ssDNA possess a limited repertoire of motifs to bind ssDNA. The hallmark of this group of anti-ssDNA may be the ability to bind nucleotide bases in subsites in the antibody binding cleft. Differences in affinity may be due to the number of subsites available to accommodate base stacking or variations in the CDRs that affect the overall molecular complementarity of the binding site to DNA.

A second group of anti-ssDNA, including 4B2, 7B3, 8D8 and 10F4, have lower affinity for oligo(dT) relative to the first group, and 4B2 and 10F4 also bind dsDNA. Anti-DNA in this group may form an ion pair in complexes with oligo(dT), as evidenced by the release of one cation upon complex formation, and show no pattern of $KMnO_4$ protection. The lack of $KMnO_4$ protection suggests the low affinity of these anti-ssDNA may be due to a different geometry of the antigen binding site in which pockets that accommodate a thymine base are not present and may be similar to the shallow binding site topology observed in crystallographic studies of anti-dsDNA Jel72, which was obtained by immunization with poly(dG)-poly(dC) (88).

Anti-ssDNA share a number of features with other ssDNA binding proteins, like T4 bacteriophage gene 32 protein and the *E. coli* single strand binding (SSB) protein (37, 89). These include specificity for and high affinity binding of. poly(dT) (e.g., apparent $K_d$ to $dT_{16}$ of 0.1 $\mu$M by SSB-1 protomer, and 14 nM by gene 32, both in 50 mM [Na+]), and involvement of tryptophan and tyrosine residues in binding, particularly through base stacking. However, the SSB and T4 bacteriophage gene 32 proteins also have several important differences, including cooperativity, several modes of DNA binding, and large ion effects consistent with extensive electrostatic interactions (89, 90). In this regard, anti-ssDNA may represent a relatively simple model of ssDNA binding proteins. In principle, understanding the mode of anti-ssDNA recognition may help illuminate the molecular basis for the intrinsic affinity of other ssDNA binding proteins to poly(dT). Indeed, structural studies of the bacteriophage f1 gene V ssDNA binding protein suggest that flexible loops within a framework of β-sheets may be a common motif used to bind ssDNA (91).

One anti-DNA in this group, 4B2, has affinity for a duplex DNA comparable to the anti-dsDNA H241 (21) and stronger than jel241 (22). In competition experiments, it was shown that dsDNA is bound in the same binding site as is ssDNA. Binding of dsDNA may be stabilized by the formation of one ion pair and ligand-induced fluorescence quenching was not observed. The number of cations released upon binding dsDNA is the same between mAb 4B2 and anti-dsDNA BV17-45 (1), but less than the four reported for anti-dsDNA Jel241 (22). Thus, the number of putative ion pairs formed may not strictly correlate with affinity, even though residues like arginine that potentially can form ion pairs are selected by anti-dsDNA and appear to contribute to dsDNA binding. Taken together, these data suggest formation of hydrogen bond networks to the backbone may play an important role in stabilizing complexes with dsDNA.

Sequence specificity of dsDNA binding proteins often results from protein secondary structures that can insert into the major groove of dsDNA to form a network of hydrogen bonds to the DNA bases (91). Whether CDR loops positioned on a framework of β-sheets can impart sequence-specific recognition of dsDNA is not known. Although several sequence-specific dsDNA binding proteins constructed from β-sheet architecture exist (92), dsDNA binding proteins which model the β-sheet-CDR loop interface in their binding site have not been reported. Stollar has proposed that the antibody binding site could straddle the phosphate backbone allowing the CDR loops to project into the major and minor grooves of dsDNA (16). Whether this arrangement can provide the basis to discriminate among related sequences is unclear. Studies in this laboratory using in vitro selection techniques are currently underway to address this point. With an appropriate consensus DNA sequence, footprinting may provide insight into the autoreactive epitopes on dsDNA recognized by anti-dsDNA.

To summarize, these studies provide detailed mechanistic insight into the recognition of ssDNA and dsDNA by anti-DNA autoantibodies. These data indicate that the range of anti-DNA reactivity is quite narrow and that anti-DNA may be grouped according to shared modes of ligand recognition. If the mechanism of binding is conserved in these groups, it may be possible to exploit this fact in the design of molecules that inhibit binding to classes of anti-DNA (8). Antagonists derived from knowledge of the molecular basis of anti-DNA-DNA interactions would, in principle, be more selective for anti-DNA than non-specific immunosuppressive agents. Although recent studies have provided cogent evidence that recognition of DNA by anti-DNA is required for renal tissue damage (7), this relationship is still poorly understood. While serum levels of anti-dsDNA are correlated with disease progression (3), antibodies to both ssDNA and dsDNA can induce nephritis in nonautoimmune mice (5, 6). Characterizing the features of DNA binding that distinguish pathogenic from nonpathogenic anti-DNA will hopefully aid in revealing the molecular basis for pathogenic self-recognition. To address these issues, the V-region genes of these mAb's were sequenced and examined their in vivo properties to provide a framework for future studies of anti-DNA structure, binding, and pathogenicity

EXPERIMENT NO. II

Cloning and Characterization of the Variable Regions of the Antibodies

Elucidating the structural features of anti-DNA that are related to their activity both in vitro and in vivo remains a key goal of SLE research. Although the genes that encode anti-DNA have been extensively studied, the molecular basis of DNA recognition by anti-DNA and the relationships between anti-DNA-DNA complex formation in vitro, and disease pathogenesis in vivo are poorly understood. One problem is that relatively few monoclonal anti-DNA have been studied for their capacity to induce nephritis, so that features which distinguish pathogenic from nonpathogenic anti-DNA are not defined. Furthermore, little is known about the ligand binding properties of nephritogenic anti-DNA compared to anti-DNA that do not induce kidney damage. To address these issues, a panel of anti-DNA from an MRL-Ipr mouse and characterized their affinity, specificity, mode of DNA binding, genetic origins, and ability to induce nephritis in vivo.

Nucleic Acid

Primers were synthesized on an Expedite Nucleic Acid Synthesizer (Milligen, Framingham, Mass.) using β-cyanoethyl phosphoramidite chemistry. Oligomers were deprotected and purified using OPC columns (ABI, Foster City, Calif.) according to the manufacturer's specifications. The preparation of ssDNA and dsDNA has been described previously.

Cloning and Sequencing of $V_H$ and $V_L$ Chain Genes

Poly(A+) RNA was isolated from $10^7$ hybridoma cells by adsorption to poly(dT) cellulose using the FastTrack mRNA isolation system (Invitrogen, San Diego, Calif.). Full length first-strand cDNA was obtained by reverse transcription of poly(A+) RNA using an oligo(dT) primer and avian myeloma reverse transcriptase using the cDNA Cycle kit (Invitrogen). Anti-DNA $V_H$ and $V_L$ genes were amplified by PCR from first strand cDNA using AmpliTaq polymerase (Perkin Elmer Cetus, Norwalk, Conn.). A degenerate set of primers was used to amplify the $V_H$ genes whereas a single primer set was used to amplify the $V_L$ sequences. The sequence of the primers is as follows (SEQ ID NOS: 106–110):

| | |
|---|---|
| VL(K) | GTGCCAGATGTGAGCTCGTGATGACCCAGTCTCCA(3') |
| $C_L$(K) | TCCTTCTAGATTACTAACACTCTCCCCTGTTGAA |
| $C_H$1 [y2a2b] | GATATCACTAGTGGGCCCGCTGGGCTC |
| $C_H$1 [y3] | TGGGCAACTAGTACCTGGGGGGGTACTGGGCTTGG |
| $V_H$ | AGGTCCAGCT(T/G)CTCGAGTC(T/A)GG |

Briefly, 10–100 ng of cDNA was added to PCR buffer (10 mM Tris-HCl pH 8.3, 50 mM KCl, 1.5 mM MgCl$_2$, 0.01% gelatin) containing dNTPs (each 250 μM), primers (each 1 μM) and AmpliTaq polymerase (5 U) to a final volume of 100 μL. The samples were overlaid with liquid wax (80 μL, MJ Research, Watertown, Mass.), denatured (94° C., 5 min) and annealed (54° C., 5 min) before being subjected to 40 cycles of extension (72° C., 3 min), denaturation (93° C., 1.5 min) and annealing (54° C., 2.5 min) using a thermal cycler (MJ Research). The length of the PCR products was verified on a 1% agarose gel.

PCR products were ligated into the precut sequencing vector pCRII (Invitrogen) using T4 DNA ligase (4 U, 15° C., 18 hours) and the construct was used to transform competent *Escherichia coli* INVαF' cells (Invitrogen) according to the manufacturer's protocol. Transformants were spread on LB agar plates containing both ampicillin (50 μg/mL) and X-Gal (10 mg/plate), and were grown overnight at 37° C. Colonies containing an insert (identified by blue-white color selection) were then grown to log phase at 37° C. in liquid LB media (5 mL) containing 50 μg/mL ampicillin. Plasmid DNA was isolated using the Wizard Miniprep kit (Promega, Madison, Wis.) and analyzed by restriction analysis with EcoRI for an insert of the correct length. Plasmid DNA (3–5 μg) was sequenced directly with a Sequenase 2.0 kit (USB, Cleveland, Ohio) following the manufacturer's alkaline denaturation protocol. Each nucleotide sequence was determined from at least two independent bacterial colonies.

Adoptive Transfer Experiments

Ten days after pristane priming, hybridoma cells (~$10^7$) from 4B2 (IgG2a), 9F11 (IgG2b), 11F8 (IgG3), and 1F/12, an IgG2a secreting control (obtained from the American Type Culture Collection, Rockville, Md.), were injected into the peritoneal cavity of 6-week old (AKR×DBA/2)F$_1$ mice (three mice per cell line). Levels of proteinuria, hematuria and antiDNA activity were measured prior to adoptive transfer and before sacrifice. Proteinuria was measured using a Chemstrip 6 (Boehringer Mannheim, Indianapolis, Ind.) and hematuria was quantified. At the onset visible ascites (between 7–21 days), mice were tail bled and serum and ascites samples were assayed for anti-DNA activity by ELISA as previously described. Mice testing positive for anti-DNA in both serum and ascites were sacrificed by anesthesia. Kidney sections were stained with either trichrome or hematoxylin/eosin and analyzed by light microscopy. Immune complex deposition was examined by direct immunofluorescence and electron microscopy as previously described. The IgG concentration in serum and ascites was determined by ELISA using a commercially available kit (Boehringer Mannheim).

In vitro Binding Assays

Binding of mAb's to protein and DNA antigens was assessed in two sets of experiments as described by Ohnishi et al. First, Immulon II microtiter plates were coated with either histone (Boehringer Mannheim), collagen type IV (Fluka, Ronkonkoma, N.Y.), fibronectin (Fluka) or laminin (ICN, Costa Mesa, Calif.) (100 μL of 5 μg/mL solutions in PBS) and then blocked with PBS containing 3% BSA. MAb's 9F11 and 11F8 (50 ng) were preincubated with either poly(dT) (50 ng) or native ctDNA, or heat denatured ctDNA (50 ng) in PBS for 1 h at 25° C. and then for 18 hours at 4° C. These complexes were then added to wells coated with the proteins described above and incubated for 2 h at 25° C. After washing wells with PBS containing 0.1% Tween-20, bound mAb was detected with alkaline phosphatase conjugated goat anti-mouse Ig followed by addition of p-nitrophenyl phosphate substrate as described by Swanson and Glick. In the second set of experiments, preformed protein-DNA complexes were coated onto microtiter plates before addition of anti-DNA mAb's. Briefly, DNA [50 ng of either poly(dT), native ctDNA, or heat denatured ctDNA] was preincubated with either histone, laminin or collagen (50 ng) for 18 hours at 4° C. and then coated onto microtiter plates. MAb's 9F11 and 11F8 (50 μg/mL of 1 μg/mL solutions in PBS containing 1% BSA and 0.05% Tween-20, PBT) were added to the appropriate wells and incubated for 2 hours at 25° C. Bound anti-DNA was detected as described above.

Binding of mAb-DNA/histone complexes to collagen IV, laminin, fibronectin and heparin sulfate (Fluka) was performed as described by Ohnishi et al. Briefly, 9F11 or 11F8 (50 ng) were preincubated with histone (100 ng) and DNA [100 ng of either poly(dT), native ctDNA, or heat denatured ctDNA] in PBS for 1 h at 25° C. and then 18 hours at 4° C. These complexes were then transferred to appropriate wells precoated with either collagen IV, laminin, fibronectin (100 μL of 10 μg/mL solutions of each in PBS) or heparin sulfate (100 μL of a 25 μg/mL solution in PBS). After incubating for 2 h at 25° C., wells were washed and bound anti-DNA was detected as described above.

MAb's 9F11 and 11F8 were examined for their ability to bind glomerular antigens present in isolated kidney. Briefly, 2-μm thick cryostat sections of naive AKR mouse kidney were mounted on glass slides as previously described. Kidney sections were then treated with deoxyribonuclease I (Sigma; immersed in 50 mL of buffer containing 20 mM Tris-Cl, pH 8, 10 mM $MgCl_2$, 100 μg/mL DNase I) for 1 h at 37° C. After washing with PBS, either normal mouse IgG, 9F11, or 11F8 (100 μL of 10 μg/mL solutions in PBS) were added to kidney slices and incubated for 1 h at 25° C. Bound antibody was detected as described previously. In a second group of experiments, the antibody of interest was preincubated with $dT_{21}$ (0.8 μM, 1 hour 25° C.) prior to incubating with the kidney section.

The binding of mAb's 4B2, 9F11 and 11F8 to mouse complement C3 was assessed following the protocol of Oshnishi et al. Briefly, heat denatured calf thymus DNA (100 μL of a 10 μg/mL solution in TBS) was coated onto Immulon II microtiter plates for 18 hours at 25° C. After blocking with PBS containing 3% BSA, purified mAb's (50 μL of a 1 μg/mL solution in PBT) were added to appropriate wells and incubated for 1 hour at 25° C. After washing, freshly pooled BALB/c serum diluted 1:25 in veronal buffered saline (either with or without preheating at 60° C. for 30 minutes) was added and incubated at 37° C. for 1 hour. Bound complement was visualized by addition of anti-mouse C3 peroxidase conjugate (Cappel, Durham, N.C.) followed by ABTS substrate (Boehringer Mannheim). A second group of experiments were performed as described above except that the diluted serum was incubated with mAb's that were precoated onto microtiter plates (50 μL of 1 μg/mL solutions in PBS) for 18 hours at 25° C. and blocked with PBS containing 3% BSA.

Serum and ascites were tested for the presence of anti-idiotype antibodies prior to, and following adoptive transfer of 11F8 hybridomas by ELISA. Briefly, the F(ab) of 11F8 was prepared and purified according to the procedure of Swanson et al. (18). Microtiter plates were coated with 11F8F(ab) (50 μL of a 1 μg/mL solution in PBS) for 18 hours at 25° C. and blocked with PBS containing 3% BSA. Serum and ascites diluted 1:100 in PBT was added and incubated for 2 h at 25° C. At this dilution, high reactivity to ssDNA is observed. Bound IgG was detected using anti-mouse Fc alkaline phosphatase conjugate (Cappel) followed by addition of p-nitrophenyl phosphate substrate (Sigma, St. Louis, Mo.).

RESULTS

Analysis of Anti-DNA V Genes

Figure 7A:
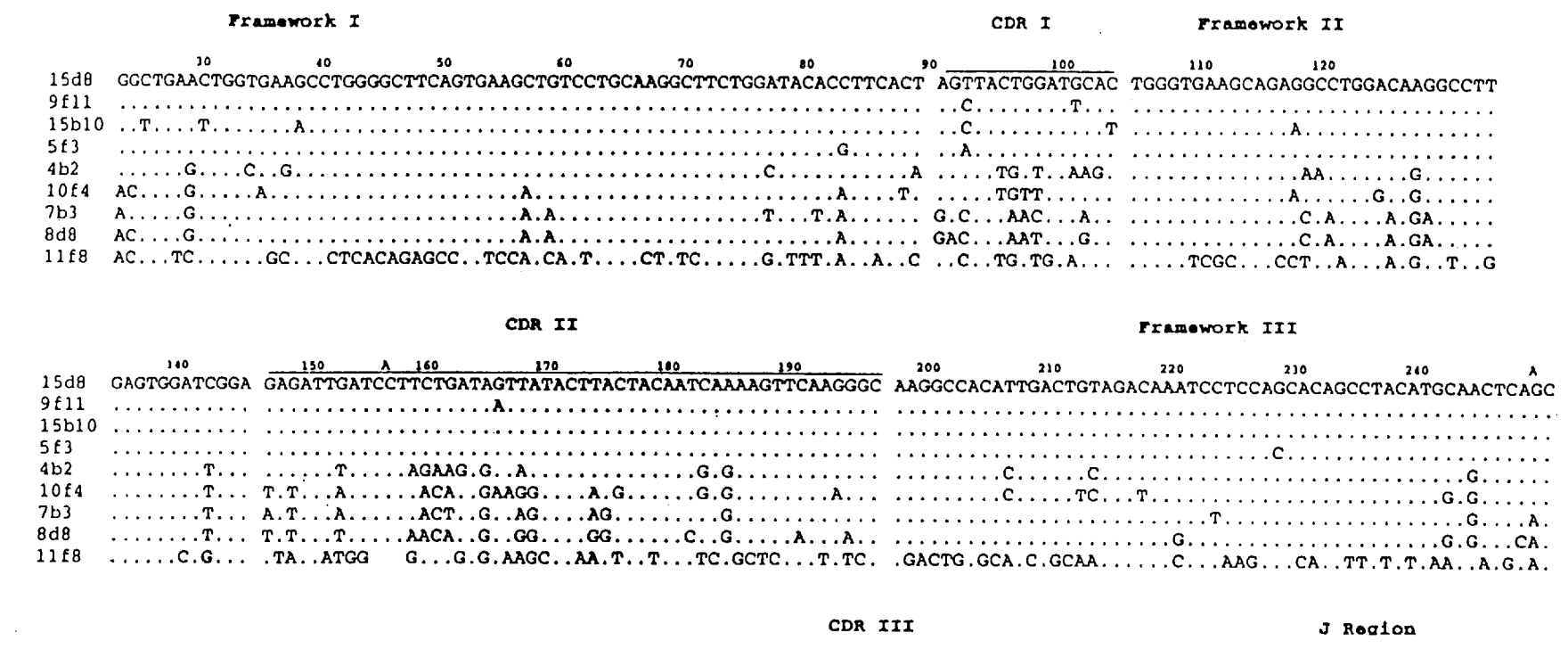
Figure 7B:
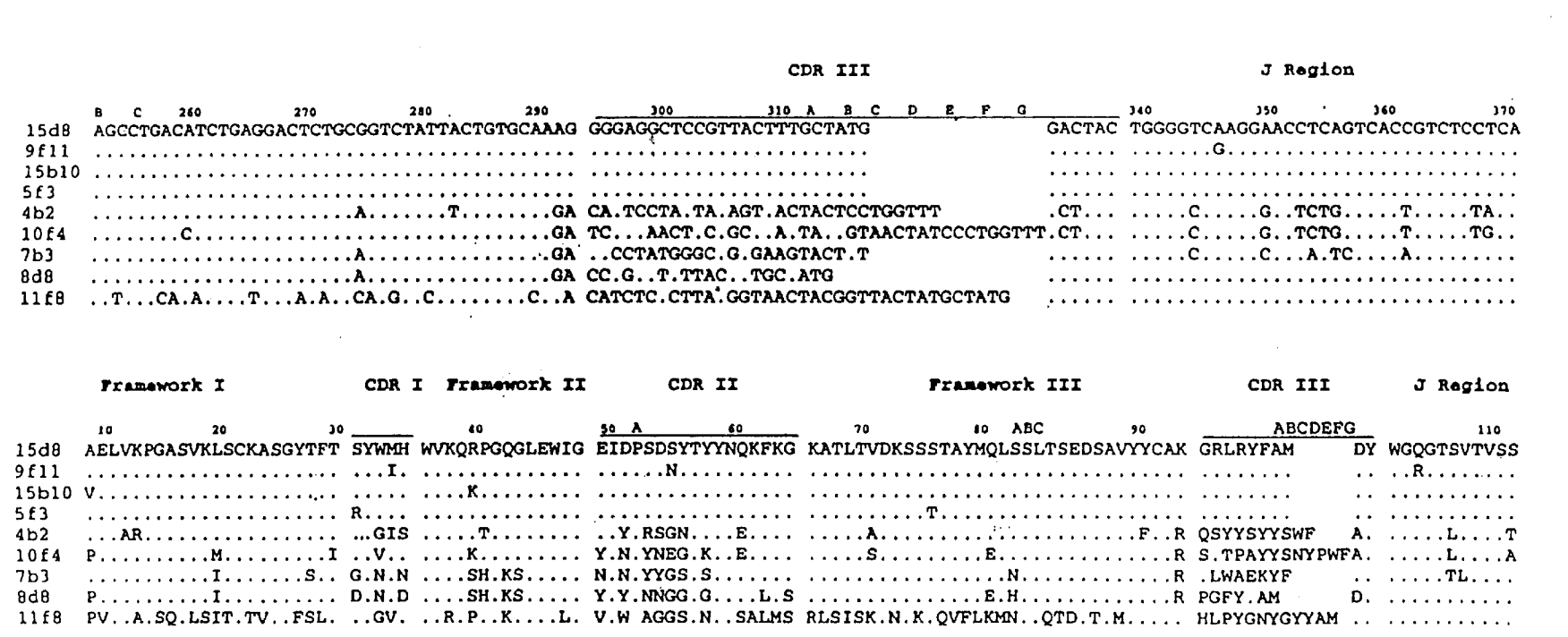
Figure 8A:
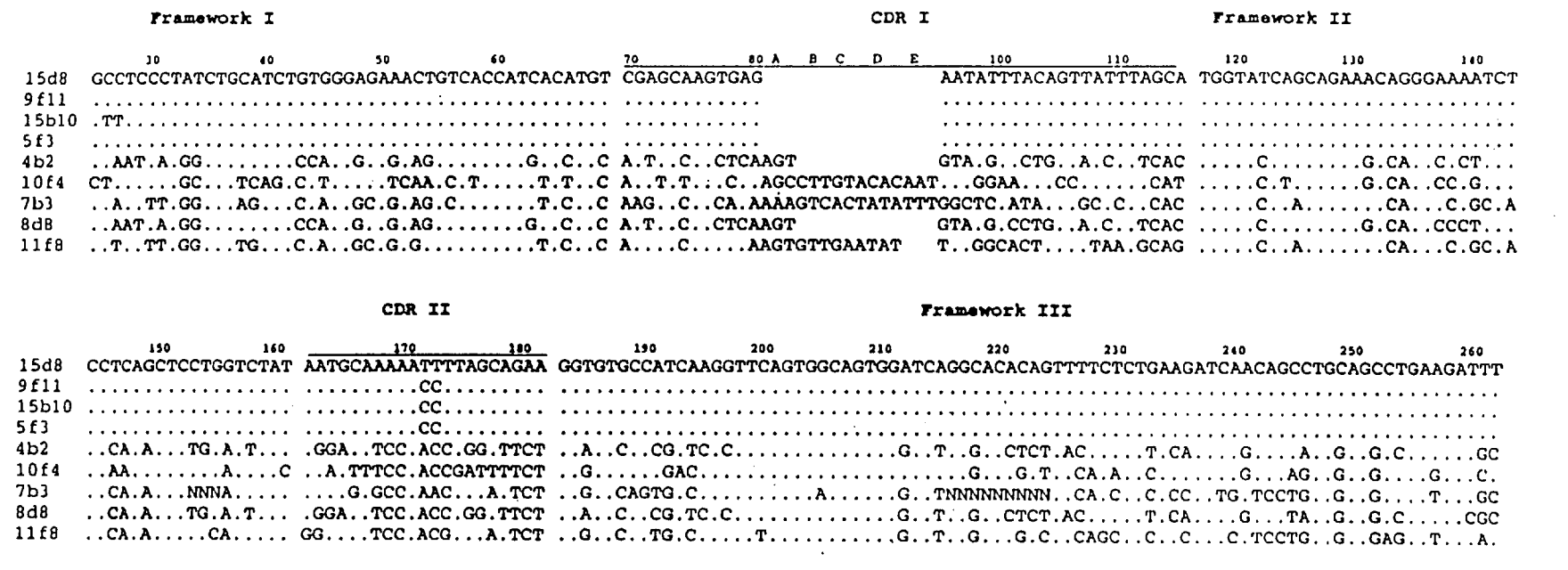

The complete $V_H$ and $V_L$ sequences and their corresponding gene families were determined for nine anti-DNA (FIGS. 7 and 8). Clones 9F11, 15B10, 15D8, and a low avidity anti-DNA 5F3, share identical $V_H DJ_H$ and VκJκ junctional regions, providing strong evidence for their clonal relatedness. The remaining anti-DNA are all single isolates. Eight of the $V_H$ genes are derived from the J558 family while one clone uses $V_H Q52$. This finding is consistent with previous genetic analysis showing that the J558 family accounts for the majority of anti-DNA $V_H$ genes. Radic and Weigert (15) have described ten homology subgroups that account for most of the $V_H J558$ derived anti-DNA. It was determined that 7B3, 8D8, and 10F4, belong to subgroups 4, 7, and 8, respectively, while the other six clones are sufficiently different to make assignment ambiguous.

In contrast to the recurrent usage of $V_H J558$ genes, five different Vκ genes are represented among these anti-DNA. Of the anti-DNA whose $V_H J558$ subgroup could be assigned, $V_H J558\text{-}V_\kappa$ pairings shown previously to be recurrent are not observed. Comparison of the gene structures of our anti-DNA to published anti-DNA $V_H$ and $V_\kappa$ genes reveal that the most closely related sequences are between 86–100% homologous. The high degree of sequence similarity to published anti-DNA sequences and the recurrent usage of the $V_H J558$ gene family suggests that this panel of mAb's are representative of antiDNA commonly expressed in lupus-prone mice.

Previous analysis of anti-DNA V genes provides evidence for recurrent structural motifs that may be associated with DNA binding. These include, among others, the presence of asparagine at position 35 in HCDR1, tyrosine at position 100 in HCDR3, arginines in HCDR3 and at position 96 of LCDR3 (particularly in association with $J_\kappa 1$), and the sequence tyr-tyr-gly-ser-ser in HCDR3. Inspection of the V-region gene structures of these anti-DNA show that several mAb's possess motifs that may confer specificity to DNA. Specifically, the HCDR1 of 7B3 encodes an asparagine at position 35 and two anti-DNA, 10F4 and 4B2, have tyrosines at position 100 of HCDR3. The group of clonally related mAb's contain two arginines at positions 96 and 98 of HCDR3 and mAb's 4B2 and 8D8 encode an arginine at position 96 of LCDR3.

The structural basis for the reactivity of three representative anti-DNA from this panel, 4B2 (IgG2a, κ), 9F11

Figure 9A:
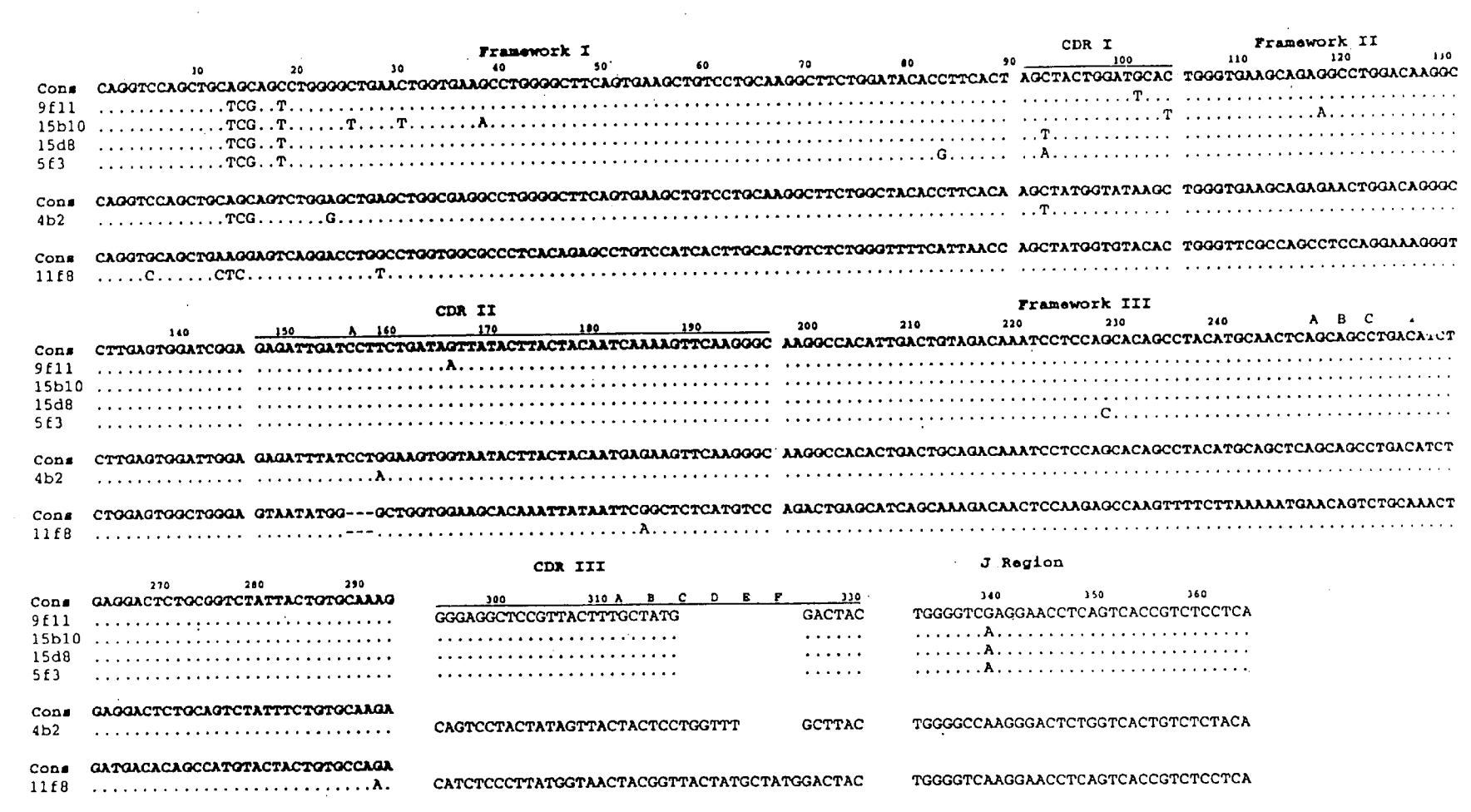
Figure 9B:
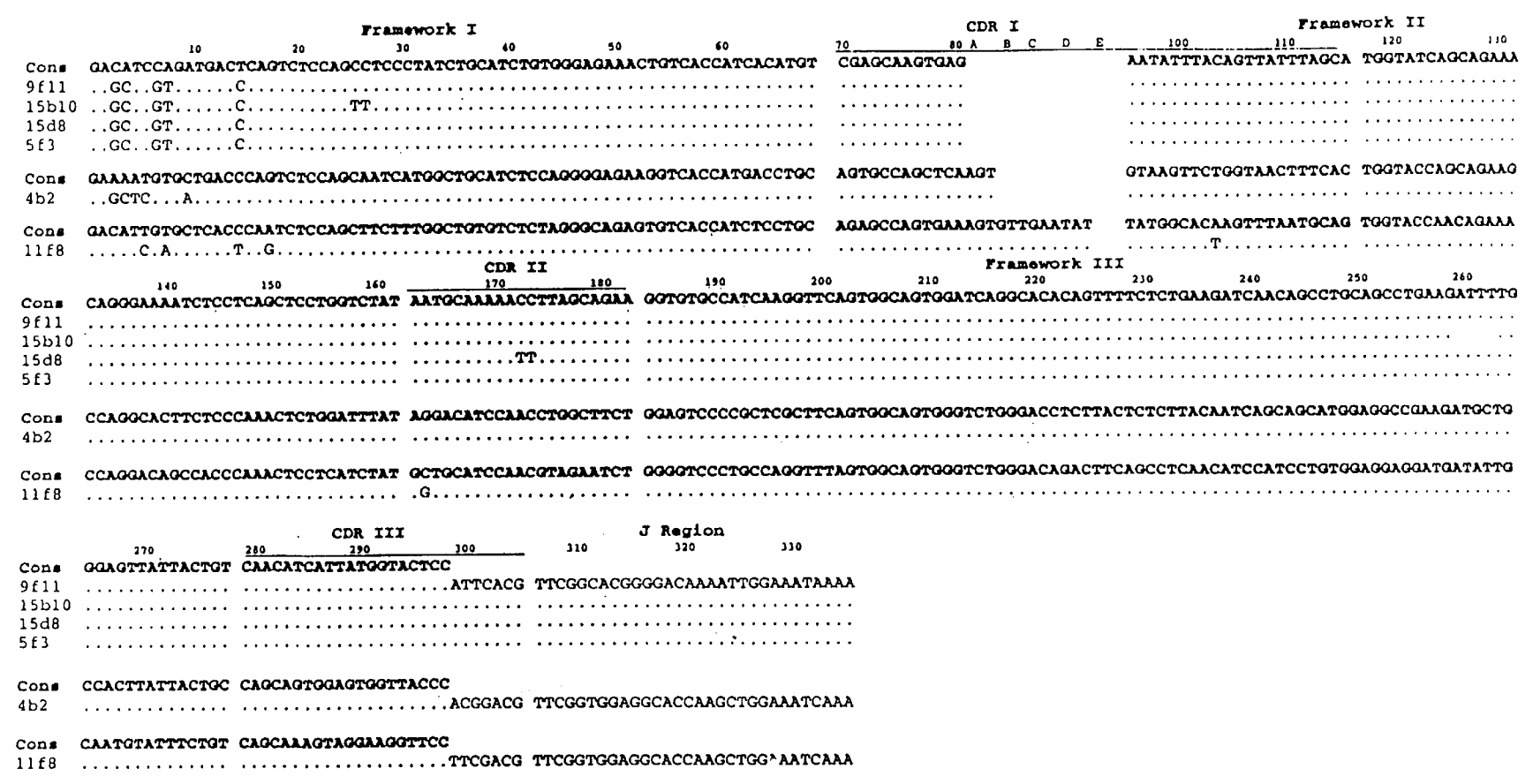
Figure 9C:
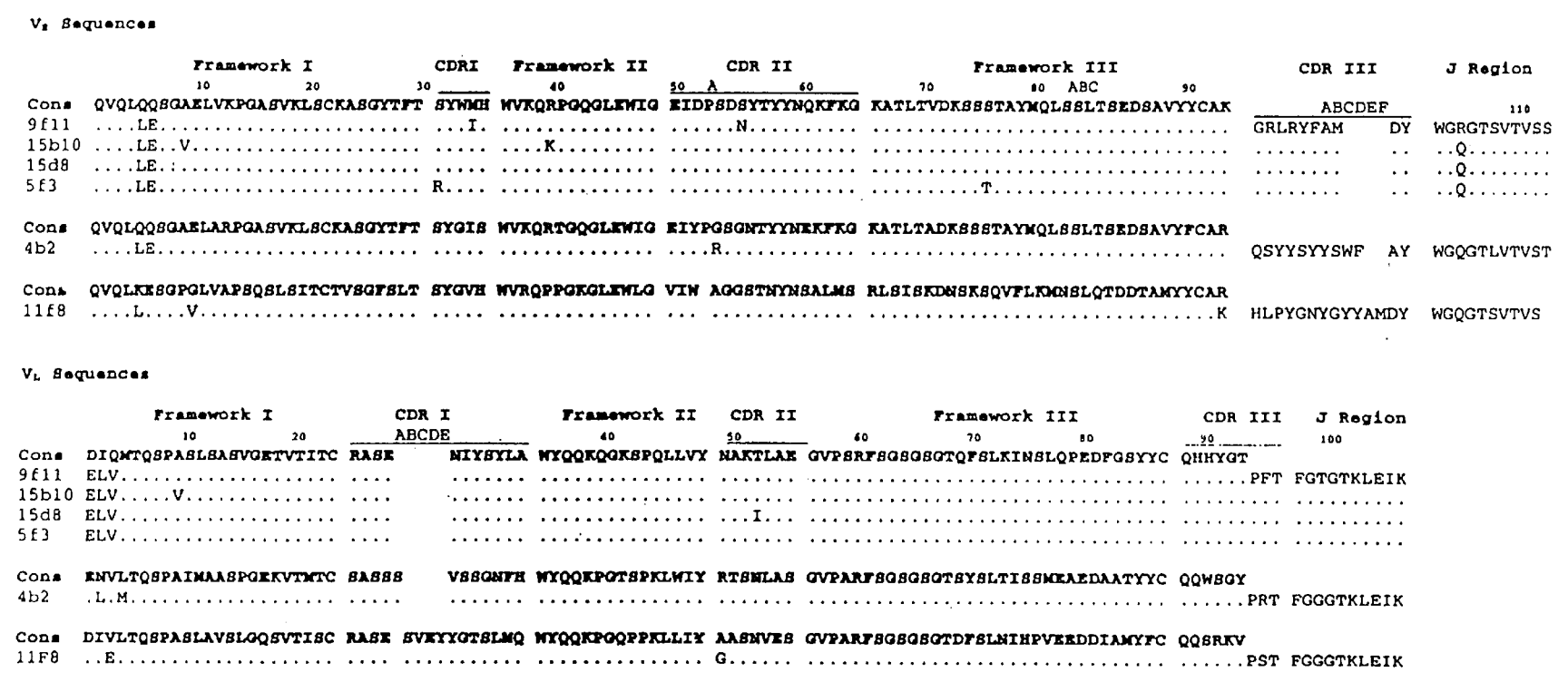

(IgG2b, κ) and 11F8 (IgG3, κ), was investigated further. These mAb's were chosen based on their DNA binding activity, gene usage, and physical properties that may be associated with pathogenicity. Clone 4B2 shares several features common to pathogenic anti-DNA like isotype and reactivity to dsDNA. Moreover, this mAb is homologous to anti-dsDNA 3H9, a mildly pathogenic anti-DNA characterized by Weigert and coworkers. MAb 9F11 represents a relatively high affinity anti-ssDNA that is part of a group of clonally related antibodies. The last mAb, 11F8, was chosen because IgG3 production has been implicated in the development of glomerular nephritis in MRL-Ipr mice. In addition, its mode of ligand recognition is similar to 9F11, thereby providing an opportunity to test the relationship between the mode of ligand binding, gene structure, and pathogenicity. Because the germline gene sequences in MRL-Ipr mice that encode anti-DNA are not characterized, we constructed putative consensus sequences for these mAb's using nucleotide sequences from both other anti-DNA, and antibodies with different binding specificities (FIG. 9).

There are few differences between the V-region of 4B2 and its consensus nucleotide sequence. Specifically, a GGA to AGA conversion at codon 53 in HCDR2 results in a gly to arg replacement. This mutation occurs in other anti-DNA like 3H9 and is thought to impart specificity for dsDNA, an observation that is consistent with the binding data obtained for 4B2. HCDR3 is apparently constructed from a $D_{SP2.7}$ gene element with short N sequences at the 5' and 3' ends (FIG. 10). The light chain is identical to the derived consensus sequence for this mAb and suggests that the 4B2 Vκ gene may be near germline in origin. A TGG to CGG conversion occurs in the Jκ1 gene that gives rise to arg at position 96 in LCDR3. Whether this mutation originates from junctional diversity or somatic mutation is unknown. Interestingly, it was previously reported that this mutation is correlated with dsDNA specificity. Although 4B2 reacts with dsDNA, the absence of dsDNA reactivity in clone 8D8, which also possesses the same Jκ mutation, suggests this correlation is not strict.

Clones 9F11, 15B10, 15D8, and 5F3 have >99% sequence identity with each other, and show little divergence from the derived consensus sequence. 9F11 differs from the $V_H$ consensus sequence at codons 34 and 55, substituting ile for met in HCDR1 and asn for ser in HCDR2. Construction of HCDR3 appears to involve fusion of $D_{Q52}$ and $D_{SP16.2}D_H$ genes (FIG. 10). The codons formed from the $D_H$—$D_H$ junction and the N addition 3' of the $D_{SP16.2}$ segment encode arginines at positions 96 and 98 of HCDR3. Both of these mechanisms have been described previously to explain the origin of arg in HCDR3 of anti-DNA. The presence of arg in HCDR3 is one characteristic feature of anti-DNA, and their selection in these mAb's may imply an important role of arg in defining their specificity. The Vκ sequence of this group is homologous to the derived consensus sequence. Clones 9F11 and 5F3 are identical, whereas mAb's 15B10 and 15D8 differ in only one codon. Specifically, 15B10 has a conservative val for ala mutation in FR1, and 15D8 loses a hydrogen bond donor/acceptor in an thr to the mutation in LCDR2. The observation that 5F3 possesses only low avidity to ssDNA whereas 9F11, 15B10 and 15D8 bind ssDNA with relatively high affinity suggests that a mutation in 5F3 strongly interferes with ligand recognition. The only mutation unique to 5F3 is a ser to arg mutation in HCDR1. Although arg mutations are generally thought to improve affinity to DNA, this mutation may disrupt the geometry of the antigen combining site by altering the conformation of the HCDR1. The structural basis for this observation is not resolved, but preliminary molecular modeling studies suggest that the ser is involved in a hydrogen bond with the carbonyl oxygen of thr 27 which may be sterically precluded by replacement with arg. Furthermore, mutagenesis experiments by Weigert offer precedence for loss of DNA reactivity by the incorporation of arg by showing that a single lys to arg mutation in HCDR2 of 3H9 completely abrogates DNA binding activity.

Two relatively conservative replacement mutations occur in the framework regions of the heavy chain of clone 11F8. One substitutes val for gly in FR1 and the other is a substitution of lys for arg at the end of FR3. HCDR3 is constructed from the fusion of an inverted $D_{SP2.5,2.7}$ and a $D_{SP2.5,2.7}$ gene (FIG. 10). In the light chain, a gly replaces ala at position 50 in LCDR2 and this is the only residue altered from the consensus sequence. Both the $J_H$ and the $J_κ$ genes are unmutated. That 11F8 may be encoded by a near germline sequence is particularly significant given previous studies showing that this mAb recognizes ssDNA with relatively high affinity and results showing this mAb is unusually pathogenic in vivo (infra).

Pathogenicity of Anti-DNA

Hybridomas of mAb's 4B2, 9F11, and 11F8, as well as an irrelevant IgG2a secreting mAb (HOPC 1F/12) were administered i.p. to 6-week old non-autoimmune (AKR×DBA/2) $F_1$ mice to determine whether these mAb's induce nephritis in vivo. This method of adoptive transfer was pursued over i.v. injection of purified mAb's because it may provide levels of circulating Ig, cytokines and inflammatory factors that more closely resemble conditions associated with active disease. All animals developed ascites within about 10 days and showed evidence of proteinurea and hematuria (Table 6). Levels of anti-DNA in serum and ascites are very similar. However, the total level of IgG produced varies among groups of mice.

Figure 11:
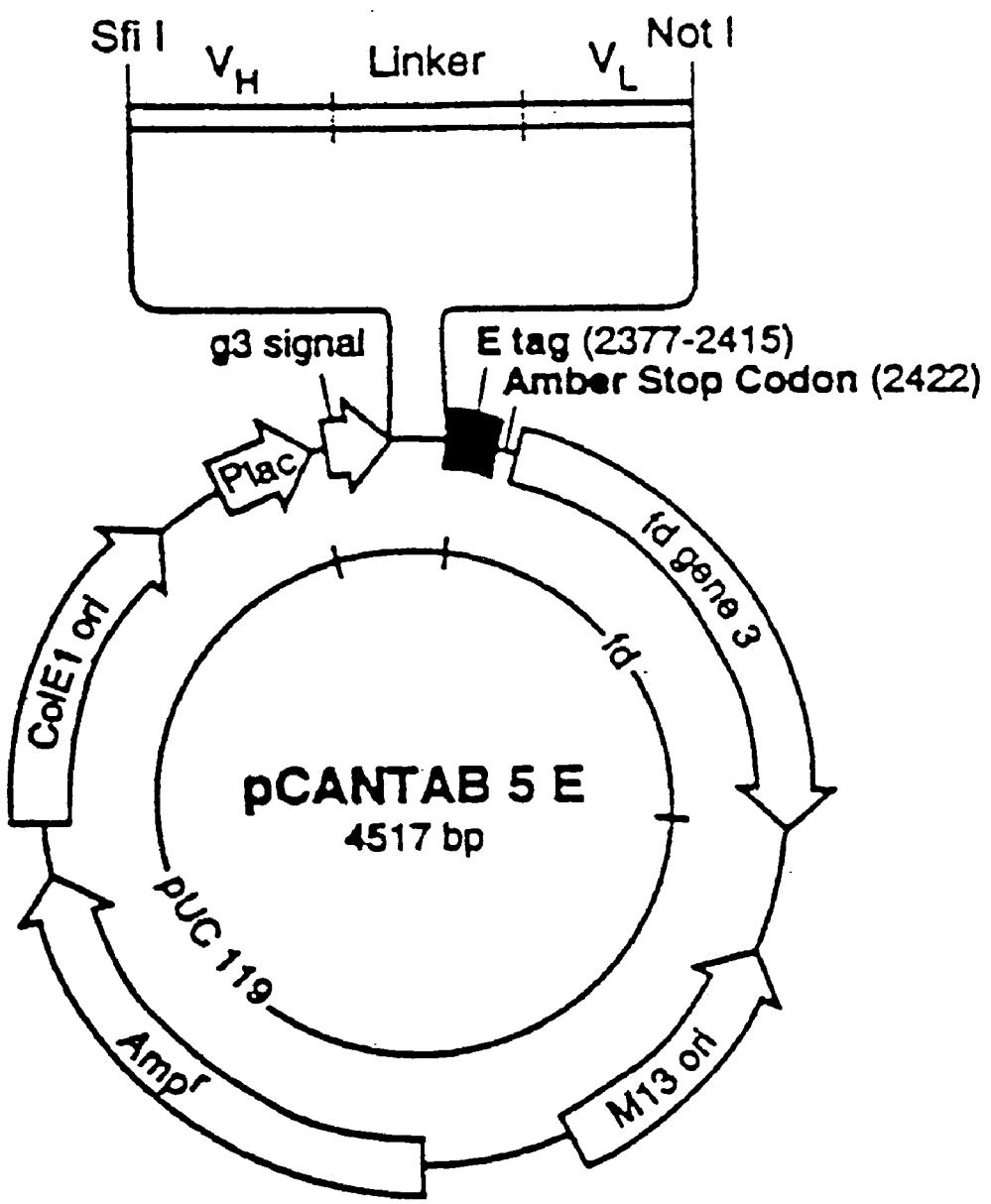
FIG. 11 is map of phagemid pCANTAB 5E. The scF$_v$ is constructed VH-region (C-terminus) to the first frawework region of $V_L$ (N-terminus) using (Gly$_4$Ser)$_3$ (SEQ ID NO: 111). The E-tag peptide (GAPVPYPDPLEPR) (SEQ ID NO: 112) for affinity purification is located at the C-terminus (3'-end) of the scF$_v$. The g3p signal sequence (SEQ ID NO: 113) (MKKLLFAIPLVVPFYAAQPA) directs transport into the periplasm. In suppressor strains of *E. coli* transformed with a recombinant vector, translation continues through the amber stop codon to produce scF'$_v$-fusion protein that is packaged and displayed on the phage tip. In nonsuppressor strains the amber stop codon is recognized and only the scF$_v$ is produced and accumulates in the periplasmic space.

The amount of circulating IgG is not correlated to the induction of nephritis in nonautoimmune mice, since mice administered with HOPC 1F/12 have larger quantities of circulating antibody than those inoculated with 11F8 but do not develop nephritis. Light microscopy of kidney sections of animals treated with 11F8 show enlarged glomerulus with cellular proliferation and infiltration of polymorphonuclear leukocytes (FIG. 11). Immunofluorescence and electron microscopy studies provide evidence of diffuse mesangial and subendothelial immune deposits with the presence "wire loop" formation. Taken together, these observations are indicative of diffuse proliferative glomerular nephritis. In contrast, the staining patterns of kidney sections from animals treated with anti-DNA 4B2 and 9F11 were not remarkably different from the negative control HOPC 1F/12 which appeared normal. The difference between the pathogenicity of 11F8 and 9F11 is striking, given the high degree of similarity in their specificity and mode of DNA binding.

Potential Mechanisms of Anti-DNA Pathogenicity

To explore the possibility that anti-DNA bound to histone-DNA complexes may localize to the glomeruli via interactions between histone and the GBM, the question of whether ternary complexes consisting of histone, mAb, and DNA [either poly(dT), ssDNA, or dsDNA] bind to heparan sulfate, collagen IV, laminin, and fibronectin was examined. Both 9F11 and 11F8 form complexes with poly(dT) and histone that bind to laminin and fibronectin, but not to heparan sulfate or collagen IV. Importantly, the levels of antibody binding to laminin and fibronectin were higher in the presence of both histone and DNA than just DNA alone. Complexes containing ssDNA or dsDNA did not bind to the ECM components tested. These results show that binding of ternary immune complexes to the GBM is a plausible mechanism for the localization of anti-DNA to the glomeruli.

To determine whether complex or uncharacterized antigens exist in vivo that were not tested in the ELISA experiments, the binding of nIgG, 9F11, and 11F8 to isolated naive kidney sections by immunofluorescence was examined. As expected, nIgG does not bind either unmanipulated or DNase I treated kidney sections. In contrast, both 9F11 and 11F8 bind to unmanipulated kidney sections and are localized to the glomeruli, and 11F8 exhibits a more intense staining pattern than 9F11. Importantly, the binding of both mAb's is abrogated by pretreatment of the kidney sections with DNase I as well as by preincubation of the mAb's with $dT_{21}$, which binds both mAb's with an apparent dissociation constant in the low nanomolar range. Collectively, these data provide strong evidence that anti-DNA specifically recognizes DNA epitopes localized to the glomeruli of the kidneys. This hypothesis is consistent with earlier studies demonstrating that binding of MRL-Ipr serum to GBM antigens is inhibited by DNAse I pretreatment and reports that anti-DNA affinity helps determine the pattern and degree of glomerular immune-complex deposition. Although 11F8 displays stronger IF than 9F11 to sections of normal kidney, the difference is not as dramatic as in kidney sections obtained in adoptive transfer studies. The small difference in in vitro anti-DNA binding may be amplified in vivo by repetitive cycles of binding, tissue damage, and release and localization of nuclear antigens in the GBM.

Several other factors that may potentially influence disease severity independent of antigen recognition were also investigated. To examine whether disease severity is correlated to the ability of the antibody to fix complement, the binding of C3 by these anti-DNA was measured and found to be similar for all three mAb's. This observation is consistent with data obtained in other laboratories and suggests that pathogenic and nonpathogenic anti-DNA cannot be distinguished by their ability to fix complement. The possibility that adoptive transfer of 11F8 initiates an anti-idiotype antibody cascade that itself mediates the pathogenicity associated with 11F8 also was explored. Although there are elevated levels of anti-DNA in the serum of mice inoculated with 11F8 hybridoma cells, there is no evidence of anti-idiotype antibodies. Lastly, the hypothesis of Izui and coworkers which proposes that IgG3 anti-DNA from MRL-Ipr mice may possess cryoglobulin activity resulting in immune complex formation through Fc—Fc interactions was explored. However, purified 11F8 does not precipitate from solution, even after extended periods at 4° C., which suggests this mAb is not a cryoglobulin.

EXPERIMENT NO. III

Cloning and Expression of Recombinant Antibodies

Recombinant antibodies were produced using the generalized procedure described below. Antibody 4B2 is used an an example. The technology is essentially that developed by Winter as implemented in the Pharmacia Recombinant Antibody serum.

mRNA Isolation, cDNA Synthesis and Primary PCR Amplification polyA$^+$ mRNA was isolated from approximately $10^7$ hybridoma cells using the FastTrack mRNA isolation kit (Invitrogen) following the manufacturer's protocols. First strand cDNA synthesis was conducted using the reagents supplied with Pharmacia Antibody System. Briefly, two identical reactions were performed, one for the $V_H$ and one for the $V_L$. The reaction mixtures (3 µL polyA$^+$ mRNA, 180 U moloney leukemia virus reverse transcriptase, primer) were incubated in the supplied buffer for 1 h at 37° C. The mixtures were then used for primary PCR amplifiction of the $V_H$ and $V_L$ sequences. For the light chain, $V_L$ Primer Mix (2 µL) was added to the cDNA, while $V_H$ primer 1 (2 µL) and $V_H$ primer 2 (2 µL) were added to the $V_H$ cDNA (sequences of the V-region primers are proprietary). AmpliTaq DNA polymerase (1 µL, 5 U) was added to both reactions and subjected to 40 cycles of PCR amplification (94° C., 1 min; 55° C., 2 min; 72° C., 2 min). The PCR products were electrophoresed on a 1% agarose gel and stained with ethidium bromide. Product bands (~350 base-pairs long) were visualized by long wave UV irradiation, excised from the gel, and purified using a Sephaglas band prep kit.

PCR Joining and Secondary Amplification

The scF$_v$ construct was built from the $V_H$ and $V_L$ genes as follows. Equimolar aliquots of the $V_H$ and $V_L$ PCR products (1 µL) along with the linker primer (0.5 µL) were dissolved in buffer containing dNTP's and AmpliTaq polymerase (2.5 U). Assembly of the three DNA fragments was conducted by 10 cycles of PCR (94° C., 1 min; 63° C., 4 min). Restriction sites for cloning (Sfi I and Not I) were then introduced in another PCR reaction; after addition of the appropriate primers, dNTP's and AmpliTaq polymerage (2.5 U), the mixture was amplified over 40 cycles (94° C., 1 min; 55° C., 2 min, and 72° C., 2 min). The product was electrophoresed on a 1% agarose TAE gel and stained with ethidium bromide. The scF$_v$ band (~750 base-pairs long) was visualized by UV irradiation, excised from the gel, and purifed using a Sephacryl microspin column.

Restriction Digest of scF$_v$ Ligation into pCANTAB 5 E, and Transformation

The termini of the scF$_v$ gene were then cleaved with the appropriate restriction enzymes for ligation into pCANTAB 5 E (FIG. 11). Briefly, Sfi (20 U) was added to the scF$_v$ gene (350 ng) and incubated for 4 h at 50° C. Once the Sfi I digest was completed, the mixture was cooled to 37° C. and Not I (40 U) was added. After incubation for 4 hours at 37° C., the DNA was purified using a microspin column. The scF$_v$ was then ligated into the predigested phagemid using T4 DNA ligase (5 U) for 1 hour at 16° C. The ligase was heat denatured for 10 min at 70° C. and the mixture was chilled on ice. For the transformation reaction, 1 mL of competent E. coli TG1 cells (K12Δ(lac-pro), supE, thi, hsdD5/F', traD36, proAB, lacIq, lacZΔM15) were pipetted into a centrifuge tube and the ligation reaction mixture from above was added. Following incubation on ice for 45 min, the mixture was heat shocked at 42° C. for 2 min, and placed on ice for 5 min. As a control, an aliquot of this mixture (100 µL) was incubated in LBG media (1 mL) for 1 h at 37° C. and was then plated on SOBAG plates (SOB media containing 100 µg/mL ampicillin and 111 mM glucose). Approximately 100 colonies were observed after 18 h incubation at 30° C. which indicated that the scF$_v$ gene was properly ligated into the phagemid.

Phage Rescue, Panning, and Reinfection

An aliquot of the 4B2 scFv transformation reaction mixture from above (800 µL) was pipetted into a sterile tube containing 2xYT-G media (15 mL of 2xYT containing 2% glucose). The sample was incubated at 37° C. with shaking until growth of OD$_{600}$~0.5 was reached (1 hour). At that point, ampicillin (75 µL of a 20 mg/mL solution) and M13KO7 helper phage ($10^{10}$ pfu) were added to the cells resuspended on 2xYT-AK (10 mL of 2xYT containing 100 µg/mL ampicillin and 50 µg/mL kanamycin). After growth at 37° C. for 18 h, the sample was centrifuged and the supernatant containing the recombinant phage was removed and transferred to a sterile tube for storage. The supernatant was filtered through a 0.45 μm filter and stored at 4° C.

One round of panning was conducted to enrich for recombinant phage expressing the 4B2 scF$_v$ gene. A sterile 25 cm² tissue culture was coated with heat denatured calf thymus DNA (5 mL of a 10 μg/mL solution) overnight. After washing with TBS, the flask was blocked with 2% dry milk in PBS, pH 7.4 for 18 hours. After the appropriate washes, the supernatant from the phage rescue (8 mL) and blocking solution (8 mL) were added to the flask. The recombinant phage were allowed to bind to the antigen-coated surface for 3 hours at 37° C. After washing, competent TG1 cells (10 mL of a culture grown to OD$_{600}$~0.3) was added to the flask and incubated for 1 hour at 37° C. An aliquot of the newly infected TG1 cells was withdrawn and diluted 1:1, 1:10, 1:100, and 1:1000. The diluted cells (100 μL) were grown on SOBAG plates at 30° C. for 18 hours. Approximately 100 colonies grew on the 1:1 plate, 10 colonies on the 1:10 plate, and no colonies were observed on the other plates. Five colonies from the 1:1 plate were used to inoculate LBG overnight cultures (25 mL). Plasmid DNA was isolated from the cultures using the Promega Wizard Kit and restriction digest showed that four of the five colonies contained the 4B2 insert (which was then verified by DNA sequencing).

Transformation of Non-SupE Bacteria for Expression

Approximately 2 ng pCANTAB 5 E-4B2 (recovered from TG1 cells) was added to 1 mL of competent *E. coli* HB2151 cells [K12Δ(lac-pro), ara, nal$^r$, thi/F' proAB, laqIq lacZΔM15] and incubated on ice for 45 min. The sample was heat shocked for 2 minutes at 42° C., then chilled on ice for 5 min. An aliquot of the transformation reaction (100 μL) was added to LBG media (900 μL), incubated for 1 h at 37° C., then plated (100 μL) on SOBAG-N media (SOB containing 100 μg/mL ampicillin, 100 μg/mL nalidixic acid, and 111 mM glucose). Roughly 50 colonies were observed after incubation for 18 h at 30° C. To confirm that the HB2151 cells contained pCANTAB 5 E-4B2, four colonies from the SOBAG-N plates were used to inoculate SB-AG media (25 mL of SB media containing 100 μg/mL ampicillin and 2% glucose). After growth at 30° C. for 12 h, plasmid DNA was isolated and digested with Sfi I and Not I as described above. Analysis of the restriction digest on a 1% agarose gel showed as insert 750 base-pairs long along with the digested pCANTAB 5 E-4B2 running 4300 base-pairs in length. Glycerol stocks of these cultures were prepared for further use.

Re-growth and Induction

Figure 12:
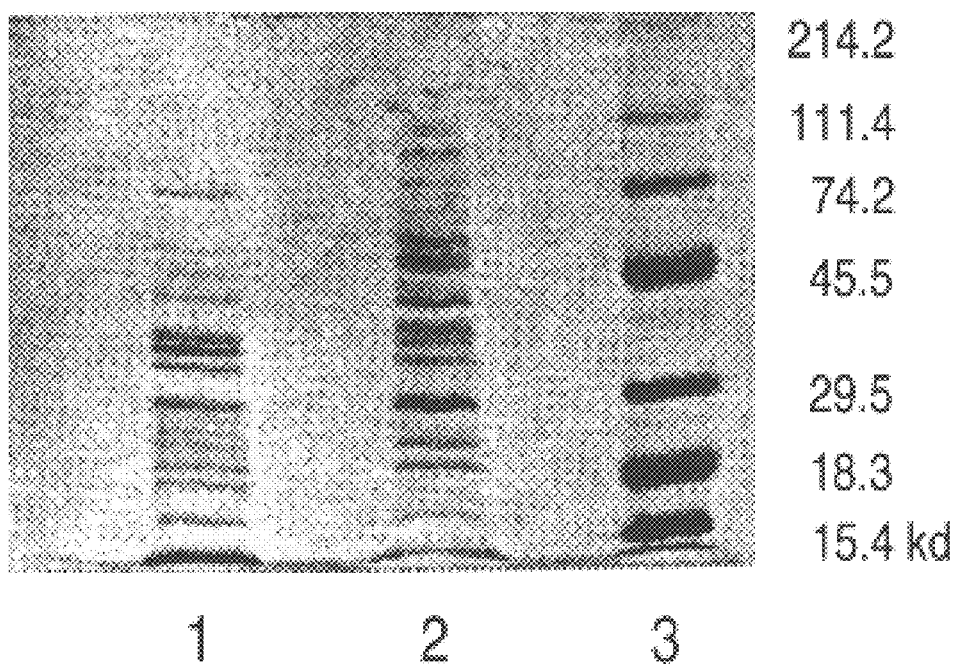
FIG. 12 shows SDS-PAGE analysis after induction of *E. coli* HB2151 cells transformed with pCANTAB 5 E-4-B2. Lane 1 shows whole cell extract. Lane 2 shows periplasmic extract TCA concentrated 20:1. Lane 3 are the molecular weight markers. The band in Lane 2 migrates as expected for the 4B2 scF$_v$ (28 kDa) and is detected with an anti-E-Tag antibody in Western blots. 4B2 scF$_v$ was not detected in pelleted cell debris or in the growth medium.

An SB-AG culture (5 mL) was inoculated with a sample from one of the glycerol stocks described above and grown at 30° C. After 12 hours, the culture was added to additional SB-AG media (50 mL) and the sample was incubated for 1 hour at 30° C. with vigorous shaking. The sample was then pelleted at 1500 g (15 min), and the pellet was resuspended in SB-Al media (50 mL of SB containing 100 μg/mL ampicillin and 1 mM IPTG). The culture was grown for 3 hours at 30° C. with vigorous shaking, divided into two portions, and centrifuged at 1500 g. The supernatant was removed and filtered through a 0.8 μm filter. One cell pellet was used to prepare a periplasmic extract while the other was used for the whole cell extract. For the periplasmic prep, the cells were resuspended in PBS (0.5 mL containing 1 mM EDTA), incubated on ice for 10 min, and then centrifuged to pellet the cell debris. The whole cell extract was prepared by resuspending the cell pellet in PBS (0.5 mL), boiling for 5 min, and centrifugation to pellet the sell debris. Aliquots of the supernatant, periplasm, and whole cell extract were analyzed by SDS-PAGE. A band migrating at 28 kDa was observed in the periplasmic extract indicating soluble expression of 4B2 scF$_v$ (FIG. 12).

DISCUSSION

As reported previously, mAb's in this panel are specific for DNA; they do not bind RNA, ribonucleoproteins, phospholipids, proteoglycans and ECM components present in normal glomerular basement membrane. These mAb's possess a high base selectivity for thymine, but the affinity and mode of DNA recognition differ among the mAb's. Specifically, anti-DNA with the highest affinity for oligo(dT) (e.g. 9F11 and 11F8) may bind ssDNA by recognizing the base moiety (in subsites) on the surface of the antigen combining site. Based on epitope mapping studies, however, 9F11 and 11F8 appear to subtly differ in the number and position of these putative subsites. Anti-DNA 4B2 binds both ssDNA and dsDNA, but recognizes ssDNA more weakly than. 9F11 and 11F8. In addition, 4B2 appears to use distinct and different mechanisms to bind ssDNA and dsDNA.

Structural Basis of Anti-DNA Specificity

To explore the relationship between gene structure and DNA specificity, the V genes of these anti-DNA were cloned and sequenced. MAb's 9F11, 15B10, and 15D8 appear clonally related which is consistent with biophysical data showing these anti-DNA share very similar DNA binding properties. Although 11F8 has similar affinity and specificity for ssDNA as does 9F11, this mAb is encoded by an entirely different set of V genes. Two other well characterized thymine specific anti-ssDNA, BV04-01 and HEd10, possess ligand binding characteristics comparable to 9F11 and 11F8. Since BV04-01 and HEd10 are encoded by V$_H$10 and V$_H$J606, respectively, an interesting question is how DNA specificity and recognition can be so similar between the four anti-DNA despite the usage of distinct V region genes. One possibility is that V$_H$ genes encode a limited repertoire of structurally conserved three dimensional motifs that form the basis of ssDNA specificity. This hypothesis is supported by recent crystallographic and modeling studies of anti-DNA which suggest that the shape of the antigen combining site may be correlated to the specificity for DNA.

There are several examples of anti-DNA that are homologous with the mAb's in this panel (Table 6). The V genes utilized by these mAb's occur in anti-DNA obtained from both autoimmune and nonautoimmune strains of mice. Importantly, both the 9F11 group of mAbs and 11F8 are encoded by V$_H$ genes similar to those found in anti-DNA obtained from normal mice immunized with bacterial DNA or protein-DNA complexes, respectively. The structural similarity between autoimmune and immunization-induced anti-DNA has been noted previously and suggests that the development of anti-DNA in normal and lupus-prone mice may occur by a common mechanism in which DNA or a protein-DNA complex stimulates appropriate B cells to differentiate in a receptor mediated response. The observation that mice immunized with Fus1-DNA complexes, from which bfd89 was derived, also develop mild nephritis supports this hypothesis and suggests that anti-DNA generated by immunization may have qualitatively similar features as autoantibodies with respect to renal pathology. However, mechanisms exist in normal individuals that may moderate the severity of the disease. Another interesting similarity is found between mAb 4B2 and 3H9, a related anti-DNA obtained from an MRL-lpr mouse. Both mAb's share the same V$_H$ and V$_κ$ genes and also recognize both ssDNA and dsDNA. These data suggest the clonal precursor that independently gave rise to these two anti-DNA may be abundant in MRL-lpr mice, or is preferentially selected during the course of the anti-DNA response. The fact that they share a common somatic mutation from gly to arg in HCDR2 indicates that their selection may be driven by the same antigen, and lends support to the latter possibility.

Although the V gene usage and structure of anti-DNA have been extensively analyzed, knowledge of the primary amino acid sequence alone yields little information about the involvement of specific residues in ligand recognition. When combined with affinity measurements and epitope mapping studies, however, these data together may help illuminate the relationship between anti-DNA structure and reactivity. For example, previous ligand binding studies of 9F11 suggest that aromatic residues, particularly trp, may by involved in ssDNA recognition through base stacking interactions, similar to that seen in studies of BV04-01 by Voss et al. (1). Genetic analysis of 9F11 verifies the presence of a single (germline encoded) trp residue at position 33 of HCDR1. Although the trp residue in 9F11 is located in a different position than BV04-01, the similarity in the mode of DNA recognition between 9F11 and BV04-01 suggests that trp 33 in HCDR1 of 9F11 may be involved in a similar interaction. Indeed, this hypothesis is supported by preliminary modeling studies. The importance of aromatic residues, particularly trp and tyr, in mediating DNA recognition may be implied by the prevalence of these residues in the CDRs of anti-DNA. Specifically, 40% of the $V_H$J558 subgroups defined by Radic and Weigert encode a trp at position 33. In many cases, this is the only solvent accessible trp residues encoded in the $V_H$CDRS, opening the possibility that these anti-DNA may share a similar mode of DNA recognition as 9F11.

The recurrence of arg in anti-DNA through somatic mutation and V(D)J joining implies that it may contribute to antigen binding and has stimulated interest in defining the mechanism by which this residue mediates DNA recognition. Sequence analysis can identify the location of arg residues, but not the mechanism by which they participate in antigen recognition. In contrast, binding studies can describe the number of ion pairs formed upon complex formation and the specific phosphates on DNA that interact with anti-DNA, but cannot distinguish between the cationic residues arg and lys. Together, these studies provide the opportunity to define both the location and the putative role of arg residues in mediating DNA binding. For example, the cumulative evidence suggests that arg 53 in HCDR2 of 4B2 may contact DNA electrostatically. In contrast to 4B2, DNA binding by 9F11 apparently does not involve ion pair formation even though genetic analysis reveals the presence of arg at positions 96 and 98 in HCDR3. Other possibilities consistent with the binding data are that the arg form a hydrogen bonding network (either directly or water-mediated) to the DNA ligand or that they serve to enforce a specific conformation in the antigen combining site through intra- or interchain CDR contacts. Preliminary modeling studies support the latter alternative and suggest that arg may contribute directly or indirectly to antigen recognition and this role may depend on its location in the antigen combining site.

| MAb | Isotype | pI | Sm | Sm/nRNP | SS-A | SS-B | Histone | Scl-70 |
|-----|---------|-----|----|---------|------|------|---------|--------|
| 7B3 | IgG2a | 7.1 | – | – | – | – | – | – |
| 8D8 | IgG2a | 6.9 | – | – | – | – | – | – |

-continued

| MAb | Isotype | pI | Sm | Sm/nRNP | SS-A | SS-B | Histone | Scl-70 |
|-----|---------|-----|----|---------|------|------|---------|--------|
| 4B2 | IgG2a | 6.9 | – | – | – | – | – | – |
| 10F4 | IgG2a | 6.7 | – | – | – | – | – | – |
| 9F11 | IgG2b | 7.0 | – | – | – | – | – | – |
| 15B10 | IgG2b | 6.8 | – | – | – | – | – | – |
| 15D8 | IgG2b | 6.8 | – | – | – | – | – | – |
| 11F8 | IgG3 | 7.0 | – | – | – | – | – | – |

| MAb | Fibronectin | Collagen IV | Laminin | Heparan Sulfate | Phosphatidyl serine | Cardiolipin |
|-----|-------------|-------------|---------|-----------------|---------------------|-------------|
| 7B3 | – | – | + | + | ++ | +++ |
| 8D8 | – | – | – | – | – | – |
| 4B2 | – | – | – | – | – | – |
| 10F4 | – | – | – | – | – | – |
| 9F11 | – | – | – | – | – | – |
| 15B10 | – | – | – | – | – | – |
| 15D8 | – | – | – | – | – | – |
| 11F8 | – | – | – | – | – | – |

| MAb | ssDNA | poly (dT) | poly (dG) | poly (dA) | poly(dI) | poly (U) | poly(C) | poly (G) |
|-----|-------|-----------|-----------|-----------|----------|----------|---------|----------|
| 7B3 | ++ | +++ | +++ | – | +++ | – | – | + |
| 8D8 | +++ | +++ | – | – | +++ | – | – | – |
| 10F4 | +++ | +++ | ++ | – | + | – | – | – |
| 4B2 | +++ | +++ | +++ | – | +++ | – | – | – |
| 9F11 | +++ | +++ | + | – | – | – | – | – |
| 15B10 | +++ | +++ | + | – | – | – | – | – |
| 15D8 | +++ | +++ | + | – | – | – | – | – |
| 11F8 | +++ | +++ | – | – | – | – | – | – |

| MAb | $dC_{21}$ | $dG_{15}$[a] | $dT_{21}$ | Duplex[b] |
|-----|-----------|--------------|-----------|-----------|
| 7B3 | 11000 | – | 4300 | – |
| 8D8 | – | 16600 | 96 | – |
| 4B2 | 4270 | 26400 | 817 | 7170 |
| 10F4 | 45500 | 7130 | 1470 | ~77000 |
| 9F11 | – | 480 | 1 | – |
| 15B10 | – | 750 | 2.9 | – |
| 15D8 | – | 1860 | 5.5 | – |
| 11F8 | – | 3230 | 44 | – |

[a]$dG_{21}$ is not synthetically accessible.
[b]Duplex = Ligand I.

| MAb | $dT_5$ | $dU_5$ | $dC_5$ | $dG_5$ |
|-----|--------|--------|--------|--------|
| 7B3 | – | NM | – | – |
| 8D8 | 5700 ± 910 | NM | – | – |
| 4B2 | – | NM | – | – |
| 10F4 | – | NM | – | – |
| 9F11 | 83 ± 16 | 300 ± 23 | – | – |
| 15B10 | 233 ± 31 | NM | – | – |
| 15D8 | 587 ± 72 | NM | – | – |
| 11F8 | 939 ± 81 | 6620 ± 800 | – | – |

TABLE 5

| Clone | Isotype | $V_H$[a] family | J558[b] Subgroup | $D_H$[c] | $J_H$[d] | $V_\kappa$[e] | $V_\kappa$[f] Subgroup | $J_\kappa$[g] |
|---|---|---|---|---|---|---|---|---|
| 9F11 | IgG2b | J558 | NA | Q52, FL16.2 | 4 | 12, 13 | NA | 4 |
| 15B10 | IgG2b | J558 | NA | Q52, FL16.2 | 4 | 12, 13 | NA | 4 |
| 15D8 | IgG2b | J558 | NA | Q52, FL16.2 | 4 | 12, 13 | NA | 4 |
| 5F3 | IgG2a | J558 | NA | Q52, FL16.2 | 4 | 12, 13 | NA | 4 |
| 4B2 | IgG2a | J558 | NA | SP 2.7 | 3 | 5 | 5 | 1 |
| 7B3 | IgG2a | J558 | 4 | SP 2, Q52 | 2 | 21 | * | 4 |
| 8D8 | IgG2a | J558 | 7 | Q52r | 4 | 5 | 5 | 1 |
| 10F4 | IgG2a | J558 | 8 | SP 2.7 | 3 | 1 | 1 | 1 |
| 11F8 | IgG3 | Q52 | — | SP 2.5, 2.7 | 4 | 21 | * | 1 |

[a]Designation based on >80% homology to members within $V_H$ gene family described by Brodeur and Riblet.
[b]Assignment according to Radic and Weigert. NA; not assignable.
[c]D gene assignments are based on homology to sequences determined by Kurosawa and Tonegawa. D genes followed by (r) are inverted.
[d]Classification according to Sakano et al.
[e]Designation according to Potter et al.
[f]Subgroups defined by Radic and Weigert. NA, not assignable; (*), assignment ambiguous.
[g]Classification according to Sakano et al.

TABLE 6

| Clone | | % Nucleotide Homology[a] | Strain[b] | Isotype | Reactivity[c] | Binding[d] | Ref |
|---|---|---|---|---|---|---|---|
| | Related Anti-DNA $V_H$ | | | | | | |
| 9F11 | SEC F2/3 | 93% | BALB/c | IgG2a,κ | ss/ECdsDNA* | ++ | |
| | 163-100 | 91% | NZB/R | IgM,κ | ssDNA | +++ | |
| 4B2 | bxw14 | 99% | NZB/W | IgM,κ | ssDNA | +++ | |
| | 3H9 | 86% | MRL-lpr | IgG2b,κ | ss/dsDNA | +++ | |
| 10F4 | 202-61 | 98% | NZB/W | IgM,κ | ssDNA | +++ | |
| 7B3 | H161 | 100% | MRL-lpr | IgG3,κ | ssDNA | ++[‡] | |
| 8D8 | 25-12m | 98% | NZB/W | IgM,κ | ssDNA | +++ | |
| 11F8 | bfd89 | 99% | BALB/c | IgM,κ | ssDNA* | +++ | |
| | Related Anti-DNA $V_\kappa$ | | | | | | |
| 9F11 | 17-s166 | 97% | NZB/W | IgM,κ | ssDNA | +++ | |
| 4B2 | 3H9 | 99% | MRL-lpr | IgG2b,κ | ss/dsDNA | +++ | |
| 10F4 | MRL-10 | 99% | MRL-lpr | IgM,κ | ssDNA | +++ | |
| 7B3 | | | | | | | |
| 8D8 | 3H9 | 98% | MRL-lpr | IgM,κ | ssDNA | +++ | |
| 11F8 | SECF5/1 | 97% | BALB/c | IgG1,κ | ECDNA* | + | |

[a]Nucleotide homologies are determined for codon 9 through codon 94.
[b]NZB/R, (NZW × SWR)F$_1$; NZB/W, (NZW × NZW)F$_1$; MRL-lpr, MRL MpJ lpr/lpr
[c]ssDNA, single-stranded DNA; dsDNA, double-stranded DNA; ECdsDNA, *E. coli* dsDNA;
[d]Assessed by competition or quantity of mAb needed to achieve given OD.
+++, <1 μg/mL; ++, 1–10 μg/mL; +, >10 μg/mL.
*, obtained by immunization; [‡], nephritogenic in non-autoimmune mice.

TABLE 7

| Hybridoma | Isotype | Serum anti-DNA[a] Pre-injection (Mean OD$_{405}$) | Serum anti-DNA Post-transfer (Mean OD$_{405}$) | Serum IgG conc[b] (mg/mL) | Ascites IgG conc (mg/mL) | C fixation[c] | Proteinuria[d] mg/dL | Hematuria erythrocytes per μL | Kidney Deposition[e] | Severity[f] |
|---|---|---|---|---|---|---|---|---|---|---|
| HOPC 1F/12 | IgG2a | 0.108 | 0.151 | 20.9 | ~50 | NM | 100 | 10–50 | none | 0 |
| 4B2 | IgG2a | 0.113 | 1.65 | 5 | 7.5 | 2.25 (0.117) | 100 | 50–250 | mes (weak) | 1 |

TABLE 7-continued

| Hybridoma | Isotype | Serum anti-DNA[a] Pre-injection (Mean OD$_{405}$) | Serum anti-DNA Post-transfer (Mean OD$_{405}$) | Serum IgG conc[b] (mg/mL) | Ascites IgG conc (mg/mL) | C fixation[c] | Proteinuria[d] mg/dL | Hematuria erythrocytes per μL | Kidney Deposition[e] | Severity[f] |
|---|---|---|---|---|---|---|---|---|---|---|
| 9F11 | IgG2b | 0.165 | 2.31 | 10.4 | 9.1 | 2.36 (0.106) | 100–500 | 50–250 | mes (weak) | 1 |
| 11F8 | IgG3 | 0.141 | 1.34 | 7.4 | 5.6 | 1.4 (0.116) | 100–500 | 50–250 | mes/subendo (strong) | 4+ |

[a]Serum or ascites was diluted 1:100 and measured for binding to heat denatured CT DNA by ELISA (see Materials and Methods). The value presented is the mean of triplicate measurements from the mice tested. The background using BALB/c sera diluted 1:100 did not exceed 0.2 AU.
[b]The concentration of IgG was determined using a commercially available ELISA kit (Boehringer Mannheim).
[c]Complement fixation as assayed by binding of murine C3 in ELISA. Presented are means of triplicate measurements taken at 405 nm after 15 min. The values obtained using heat denatured samples are shown in parentheses. NM, not measured.
[d]Proteinuria was estimated using Chemistrip 6.
[e]Mes, mesangial; subendo, subendothelial.
[f]As assessed by direct immunofluorescence with FITC conjugated goat anti-mouse IgG and electron microscopy

REFERENCES

1. Voss, E. W. Jr. 1990. *Anti-DNA antibodies in SLE*. E. W. Voss, Jr., ed. CRC Press, Boca Raton, Fla.
2. Tan, E. M. 1989. Antinuclear antibodies: diagnostic markers for autoimmune diseases and probes for cell biology. *Adv. Immunol.* 44:93.
3. Koffler, D., P. H. Schur, and H. G. Kunkel. 1967. Immunological studies concerning the nephritis of systemic lupus erythematosus. *J. Exp. Med.* 126:607.
4. Foster, M. H., B. Cizman, and M. P. Madaio. 1993. Nephritogenic autoantibodies in systemic lupus erythematosus: inununochemical properties, mechanisms of immune deposition, and genetic origins. *Lab. Invest.* 69:494.
5. Vlakos, D. V., M. H. Foster, S. Adams, M. Katz, A. A. Ucci, K. J. Barrett, S. K. Datta, and M. P. Madaio. 1992. Anti-DNA antibodies form immune deposits at distinct ~glomerular and vascular sites. *Kidney ~Int.* 41:1690.
6. Tsao, B. P., F. M. Ebling, C. Roman, N. Panosian-Sahakian, K. Calame, and B. Hahn. 1990. Structural characteristics of the variable regions of immunoglobplin genes encoding a pathogenic autoantibody in murine lupus. *J. Clin. Invest.* 85:530.
7. Katz, J. B., W. Limpanasithikul, and B. Diamond. 1994. Mutational analysis of an autoantibody: differential binding and pathogenicity. *J. Exp. Med.* 180:925.
8. Ben-Chetrit, E., D. Eliat, and S. A. Ben-Sasson. 1988. Specific inhibition of the DNA anti-DNA immune reaction by low molecular weight anionic compounds. *Immunology* 65:479~.
9. Jones, D. S., J. P. Hachmann, S. A. Osgood, M. S. Hayag, P. A. Barstad, G. M. Iverson, and S. M. Coutts. 1994. Conjugates of double-stranded oligonucleotides with polyethylene glycol) and keyhole limpet hemocyanin: a model for treating systemic lupus erythematosus. *Bioconjugate Chem.* 5:390.
10. Stollar, D., L. Levine, H. I. Lehrer, H. Van Vunakis. 1962. The antigenic determinants of denatured DNA reactive with lupus erythematosus serum. *Proc. Natl. Acad. Sci. USA* 48:874.
11. Koffler, D., R. Carr, V. Agnello, R. Thobum, and H. G. Kunkel. 1971. Antibodies to polynucleotides in human sera: antigenic specificity and relation to disease. *J. Exp. Med.* 134:294.
12. Eilat, D. 1982. Monoclonal antibodies: an approach to studying autoimmune disease. *Mol. Immunol.* 19:943.
13. Taki, S., S. Hirose, K. Kinoshita, H. Nishimura, T. Shimamura, J. Hamuro, and T. Shirai. 1992. Somatically mutated IgG anti-DNA antibody clonary related to germline encoded IgM anti-DNA antibody. *Eur. J. Immunol.* 22:987.
14. Marion, T. N., D. M. Tillman, N-T. Jou, and R. J. Hill. 1992. Selection of immunoglobulin variable regions in autoimmunity to DNA. *Immunol. Reviews* 128:123.
15. Radic, M. Z., and M. Weigert, M. 1994. Genetic and structural evidence for antigen selection of anti-DNA antibodies. *Ann. Rev. Immunol.* 12:487 and references therein.
16. Eilat, D., and W. F. Anderson. 1994. Structure-function correlates of autoantibodies to nucleic acids. Lessons from immunochemical, genetic and structural studies., *Mol. Immunol.* 184:1377.
17. Herron, J. N., X. M. He, D. W. Ballard, P. R. Blier, P. E. Pace, A. L. M. Blothwell, E. W. Voss, Jr., and A. B. Edmundson. 1991. An autoantibody to single-stranded DNA: comparison of the three-dimensional structures of the unliganded Fab and a deoxynucleotide-Fab complex. *Proteins* 11:159.
18. Swanson, P. C., B. C. Cooper, and G. D. Glick. 1994. High resolution epitope mapping of an anti-DNA autoantibody using model DNA ligands. *J. Immunol.* 152:2601.
19. Smith, R. G., D. W. Ballard, P. R. Blier, P. E. Pace, A. L. M. Blothwell, J. N. Herron, A. B. Edmunson, and E. W. Voss, Jr., 1989. Structural features of a murine monoclonal anti-ssDNA autoantibody. *J. Indian Inst. Sci.* 69:25.
20. Lee, J. S., D. F. Dombroski, and T. R. Mosmann. 1982. Specificity of autoimmune monoclonal Fab fragments binding to single-stranded deoxyribonucleic acid. *Biochemistry* 21:4940.
21. Stollar, B. D., G. Zon, and R. W. Pastor. 1986. A recognition site on synthetic helical oligonucleotides for monoclonal anti-native DNA autoantibody. *Proc. Natl. Acad Sci. USA*. 83:4469.
22. Braun R. P., and J. S. Lee. 1–987. Equilibrium binding parameters of an autoimmune monoclonal antibody specific for double-stranded DNA. *J. Immunol.* 139:175.
23. Oi, V. T., L. A. Herzenberg. 1980. In *Selected methods in cellular immunology*. B. B. Mishell and S. M. Shiigi, eds. W. H. Freeman, New York, N.Y. p. 291.
24. Margulies, D. H., W. M. Kuehl, and M. D. Scharff. 1976 Somatic cell hybridization of mouse myeloma cells. *Cell* 8:405.
25. Papalian, M., E. Lafer, R. Wong, and B. D. Stollar. 1980 Reaction of systemic lupus erythematosus antinative DNA antibodies with native DNA fragments from 20 to 1200 base pairs. *J. Clin. Invest.* 65:469.
26. Glick, G. D., S. E. Osbome, D. S. Knitt, and J. P. Marino, Jr. 1992. Trapping and isolation of an alternate DNA conformation. *J. Am. Chem. Soc.* 114:5447.
27. Harlow, E. and D. Lane. 1988. In *Antibodies: A laboratory manual* Cold Spring Harbor Laboratory, Cold Spring Harbor, N.Y. p. 84.

28. Zouali, M., and B. D. Stollar. 1986. A rapid ELISA for measurement of antibodies to nucleic acid antigens using UV-treated polystyrene microplates. *J. Immunol. Methods* 90:105.
29. Eaton, R. B., G. Schnneider, and P. H. Schur. 1983. Enzyme immunoassay for antibodies to native DNA. *Arthritis Rheum.* 26:52.
30. Smeenk, R. J., K. Brinkman, H. G. van den Brink, and A. A. Westgeest. 1988. Reaction patterns of monoclonal antibodies to DNA. *J. Immunol.* 140–3786.
31. Sabbaga, J., S. R. Line, P. Potocnjak, M. P. Madaio. 1989. A murine nephritogenic monoclonal anti-DNA autoantibody binding directly to mouse laminin, the major noncollagenous component of the glomerular basement membrane. *Eur. J. Immunol.* 19:137.
32. Gay, S., M. J. Losman, W. J. Koopman, and E J. Miller. 1985. Interaction of DNA with connective tissue matrix proteins reveals preferential binding to type V collagen. *J. Immunol.* 129:1097.
33. Faaber, P., T. P. Rijke, L. B. van de Putte, P. J. Capel, and J. H. Berden. 1986. Crossreactivity of human and murine anti-DNA antibodies with heparan sulfate, the major glycosaminoglycan in glomerular basement membranes. *J. Clin. Invest.* 77:1824.
34. Lake, R. A., A. Morgan, B. Henderson, and N. A. Staines. 1985. A key role for fibronectin in the sequential binding of native dsDNA and monoclonal anti-DNA antibodies to components of the extracellular matrix: its possible significance in glomerulonephritis. *Immunology* 54:389.
35. Stevens, S. Y., P. C. Swanson, E. W. Voss, Jr., and G. D. Glick. 1993. Evidence for induced fit in antibody-DNA complexes. *J. Am. Chem. Soc.* 115:1585.
36. Kelly, R. C., D. E. Jensen, and P. H. von Hippel. 1976. DNA melting proteins. IV. Fluorescence measurements of binding parameters for bacteriophage T4 gene 32-protein to mono-, oligo-, and polynucleotides. *J. Biol. Chem.* 251:7240.
37. Kim, Y. T., S. Tabor, C. Bortner, J. D. Griffith, and C. C. Richardson. 1992. Purification and characterization of the bacteriophage T7 gene 2.5 protein. *J. Biol. Chem.* 267:15022.
38. Andrew, S. M. and J. A. Titus. 1991. Antibody detection and preparation. In *Current Protocols in Immunology*, Vol. 1. J. E. Coligan, A. M. Kruisbeek, D. H. Marguilies, E. M. Shevach, and W. Strober, eds. John Wiley and Sons, New York, N.Y.
39. Eilat, D. 1985. Cross-reactions of anti-DNA and the central dogma of lupus nephritis. *Immunology Today* 6:123.
40. Schwartz, R. S., and B. D. Stollar. 1985. Origins of anti-DNA autoantibodies. *J. Clin. Invest.* 75:321.
41. Mohan, C., S. Adams, V. Stanik, S. K. Datta. 1993. Nucleosome: a major inimunogen for pathogenic autoantibody-inducing T cells of lupus. *J. Exp. Med.* 177.1367.
42. Madaio, M. P., J. Carlson, J. Cataldo, A. Ucci, P. Mgliorini, and O. Pankewycz. 1987. Murine monoclonal anti-DNA antibodies bind directly to glomerular antigens and form immune deposits. *J. Immunol.* 138:2883.
43. Pankewycz, O. G., P. Mgliorini, and M. P. Madaio. 1987. Polyreactive autoantibodies are nephritogenic in murine lupus nephritis. *J. Immunol.* 139:3287.
44. Termaat, J-H., K. J. Assman, H. B. Dukman, F. von Gompel, R. J. Smeenk, and Berden, J. H. 1992. Anti-DNA antibodies can bind to the glomerulus via two distinct mechanisms. *Kidney Intl.* 42:1363.
45. Ohnishi, K., F. M. Ebling, B. Mitchell, R. R. Singh, B. H. Hahn, and B. P. Tsao. 1994. Comparison of pathogenic and non-pathogenic murine antibodies to DNA: antigen binding and structural characteristics. *Int. Immunol.* 6:817.
46. Edberg, J. C., and R. P. Taylor. 1986. Quantitative aspects of lupus anti-DNA autoantibody specificity. *J. Immunol.* 136:4581.
47. Costello, P. B., and F. A. Green. 1988. Binding affinity of serum immunoglobulin G to cardiolipin and other phospholipids in patients with systemic lupus erythematosus and syphilis. *Infection and Immunity* 56:1738.
48. Brinkman, K., R. Termaat, J. H. Berden. R. J. Smeenk. 1990. Anti-DNA antibodies and lupus nephritis: the complexity of crossreactivity. *Immunology Today* 11:232.
49. Andrejewski, A., Jr., J. Rauch, E. Lafer, B. D. Stollar, and R. S. Schwartz. 1981. Antigen-binding diversity and idiotypic cross-reactions among hybridoma autoantibodies to DNA. *J. Immunol.* 126.226.
50. Arnott, S. 1970. The geometry of nucleic acids. *Prog. Biophys. Molec. Biol.* 21:265.
51. Pesce, A. J., and J. G. Michael. 1992. Artifacts and limitations of enzyme immunoassay. *J. Immunol. Methods* 150:111.
52. Sanford, D. G. and B. D. Stollar. 1992. Assay of anti-DNA antibodies. *Methods Enzymol.* 212:355.
53. Fried, M. G. and D. M. Crothers. 1981. Equilibria and kinetics of lac repressor-operator interactions by polyacrylamide gel electrophoresis. *Nucleic Acids Res.* 9:6505.
54. Tetin, S. Y., C. A. Rumbley, T. L. Hazlett, and E. W. Voss, Jr. 1993. Elucidation of anti ssDNA autoantibody BV04-01 binding interactions with homooligonucleotides. *Biochemistry* 32:9011.
55. Wang, H., S. E. Osbome, E. R. Zuiderweg, and G. D. Glick. 1994. Solution structure of a disulfide crosslinked DNA hairpin. *J. Am. Chem. Soc.* 116:5022.
56. Wing, R., H. Drew, T. Takano, C. Broka, S. Tanaka, K. Itakura, and R. E. Dickerson. 1980. Crystal structure analysis of a complete turn of B-DNA. *Nature* 287:755.
57. Weeks, K. M., and D. M. Crothers. 1992. RNA binding assays for Tat-derived peptides: implications for specificity. *Biochemistry* 31:10281.
58. Record, M. T. Jr., T. M. Lohman, and P. de Haseth. 1976. Ion effects on ligand-nucleic acid interactions. *J. Mol. Biol.* 107:145.
59. Lohman, T. M., P. L. de Haseth, and M. T. Record. 1980. Pentalysine-deoxyribonucleic acid interactions: a model for the general effects of ion concentrations on the interactions of proteins with nucleic acids. *Biochemistry* 19:3522.
60. Radic, M. Z., J. Mackle, J. Erickson, C. Mol, W. F. Anderson, and M. Weigert. 30 1993. Residues that mediate DNA binding of autoimmune antibodies. *J. Immunol.* 150:4966.
61. Chothia, C. and A. M. Lesk. 1987. Canonical structures for the hypervariable regions of immunoglobulins. *J. Mol. Biol.* 196:901.
62. Stanfield, R. L., T. M. Fieser, R. A. Lemer, and I. A. Wilson. 1990. Crystal structure of an antibody to a peptide and its complex with peptide antigen at 2.8 A. *Science* 248:712.
63. Kowalczykowski, S. C., L. S. Paul., N. Lonberg, J. W. Newport, J. A. McSwiggen, and P. H. von Hippel. 1986. Cooperative and noncooperative binding of protein ligands to nucleic acid lattices: experimental approaches to the determination of thermodynamic parameters. *Biochemistry* 25:1226.

64. Rhodes, D. 1989. Analysis of sequence-specific DNA binding proteins. In *Protein Function: A Practical Approach*. T. E. Creighton, ed. IRL Press, Oxford, p. 177.
65. Rini, J. M., U. Schulze-Gahmen, and I. A. Wilson. 1992. Structural evidence for induced fit as a mechanism for antibody-antigen recognition. *Science* 255:959.
66. Getzoff, E. D., J. A. Tainer, R. A. Lerner, and H. M. Geysen. 1988. The chemistry and mechanism of antibody binding to protein antigens. *Adv. Immunol.* 43:1.
67. Draper, D. E. 1993. Protein-DNA complexes: the cost of recognition. *Proc. Natl. Acad. Sci. USA* 90:7429.
68. Lesser, D. R., M. R. Kurpiewski, and L. Jen-Jacobson. 1990. The energetic basis of specificity in the Eco RI endonuclease-DNA interaction. *Science* 250.776.
69. La Baer, J. and K. R. Yamamoto. 1994. Analysis of the DNA-binding affinity, sequence specificity and context dependence of the glucocorticoid receptor zinc finger region. *J. Mol. Biol.* 239:664.
70. Isenberg D. A., M. R. Ehrenstein, C. Longhurst, and J. K. Kalsi. 1994. The origin, sequence, structure and consequences of developing anti-DNA antibodies. A human perspective. *Arthritis Rheum.* 37:169.
71. Madaio, M. P., S. Hodder, R. S. Schwartz, and B. D. Stollar. 1984. Responsiveness of autoimmune and normal mice to nucleic acid antigens. *J. Immunol.* 132:872.
72. Erikson, J., M. Z. Radic, S. A. Camper, R. R. Hardy, C. Carmack, and M. Weigert. 1991. Expression of anti-DNA inimunoglobulin transgenes in non-autoimmune mice. *Nature* 349:331.
73. Watanabe-Fukunaga, R., C. I. Brannan, N. G. Copeland, N. A. Jenkins, and S. Nagata. 1992. Lymphoproliferation disorder in mice explained by defects in Fas antigen that mediates apoptosis. *Nature* 296:314.
74. Strasser, A., S. Whittingham, D. L. Vaux, M. L. Bath, J. M. Adams, S. Cory, and A. W. Harris. 199 1. Enforced bcl2 expression in B-lymphoid cells prolongs antibody responses and elicits autoimmune disease. *Proc. Natl. Acad. Sci. USA* 88:8661.
75. Polymenis, M. and B. D. Stollar. 1994. Critical binding site amino acids of anti-Z-DNA single chain Fv molecules. Role of heavy and light chain CDR3 and relationship to autoantibody activity. *J. Immunol.* 152:5318.
76. Rumbley, C. A., L. K. Denzin, L. Yantz, S. Y. Tetin, and E. W. Voss, Jr. 1993. Construction, characterization, and selected site-specific mutagenesis of an anti-single-stranded DNA single-chain autoantibody. *J. Biol. Chem.* 268:13667.
77. Sharon, J. 1990. Structural correlates of high antibody affinity: three engineered amino acid substitutions can increase the affinity of an anti-p-azophenylarsonate antibody 200-fold. *Proc. Natl. Acad. Sci. USA* 87:4814.
78. Schillbach, J. F., R. I. Near, R. E. Bruccoleri, E. Haber, P. D. Jeffrey, J. Novotny, S. Sheriff, and M. N. Margolies. 1993. Modulation of antibody affinity by a non-contact residue. *Protein Science* 2:206.
79. Shefner, R., G. Kleiner, A. Turken, L. Papazian, and B. Diamond. 1991. A novel class of anti-DNA antibodies identified in BALB/c mice. *J. Exp. Med.* 173:287.
80. Foster, M. H., M. P. Madaio, and K. J. Baffett. 1992. Variable region sequence analysis of anti-DNA antibodies: evidence for a family of closely related germ-line VH genes encoding lupus autoantibodies. *DNA Cell Biol.* 11:175.
81. Sanger, W. and U. Heinemann. 1989. *Protein-Nucleic Acid Interaction*. CRC Press, Boca Raton, Fla.
82. Stevens, S. Y., P. C. Swanson, and G. D. Glick. 1994. Application of the gel shift assay to study the affinity and specificity of anti-DNA antibodies. *J. Immunol. Methods* 177:185.
83. Polymenis, M. and B. D. Stollar. 1995. Domain interactions and antigen binding of recombinant anti-Z-DNA antibody variable domains. The role of heavy and light chains measured by surface plasmon resonance. *J. Immunol.* 154:2198.
84. Sanford, S. G., and B. D. Stollar. 1990. Characterization of anti-Z-DNA antibody binding sites on Z-DNA by nuclear magnetic resonance spectroscopy. *J. Biol. Chem.* 265:18608.
85. Cygler, M., A. Boodhoo, J. S. Iee, and W. F. Anderson. 1987. Crystallization and structure of an autoimmune anti-poly(dT) immunoglobulin Fab fragment at 3.0 A resolution. *J. Biol. Chem.* 262:643.
86. Record, M. T., Jr. and R. S. Spolar. 1990. Some thermodyna~mic principles of nonspecific and site specific protein-DNA interactions. In *The biology of nonspecific DNA-protein interactions*. A. Rezvin, ed. CRC Press, Boca Raton, Fla., p. 33.
87. Bhat, T. N., G. A. Bently, G. Boulot, M. I. Greene, D. Tello, W. Dall'Acqua, H. Souchon, F. P. Schwartz, R. A. Mariuzza, and R. J. Poljak. 1994. Bound water molecules and conformational stabilization mediate an antigen-antibody association. *Proc. Natl. Acad. Sci.* 91:1089.
88. Mol, C. D., A. K. Muir, J. S. Lee, and W. F. Anderson. 1994. Structure of an immunoglobulin Fab fragment specific for poly(dG)-poly(dC). *J. Biol. Chem.* 269:3605.
89. Lohman, T. M. and W. Bujalowski. 1990. *Escherichia coli* single strand binding protein: multiple single-stranded DNA binding modes and cooperativities. In *The biology of nonspecific DNA-protein interactions*. A. Rezvin, ed. CRC Press, Boca Raton, Fla., p. 131.
90. Karpel, R. L. 1990. T4 bacteriophage gene 32 protein. In *The biology of nonspecific DNA-protein interactions*. A. Rezvin, ed. CRC Press, Boca Raton, Fla., p. 103.
91. Skinner, M. M., H. Zhang, D. H. Leschnitzer, Y. Guan, H. Bellamy, R. M. Sweet, C. W. Gray, R. N. Konings, A. H. Wang, and T. C. Terwilliger. 1994. Structure of the gene V protein of bacteriophage f1 detemined by multiwavelength x-ray diffraction on the selenomethionyl protein. *Proc. Natl. Acad. Sci. USA* 91:2071.
92. Pabo, C. O., and R. T. Sauer. 1992. Transcription factors: structural families and principles of DNA recognition. *Annu. Rev. Biochem.* 61:1053.

What is claimed is:

1. A method of inhibiting or preventing a pathology associated with the binding of DNA-antibodies to DNA in a subject by administering to the subject an effective amount of a 1,4 benzodiazepine derivative.

2. The method of claim 1, wherein the pathology associated with the binding of DNA-antibodies to DNA is inflammatory glomerulonephritis or systemic lupus erythematosus.

3. The method of claim 1 through 2, wherein the DNA is ssDNA.

* * * * *

UNITED STATES PATENT AND TRADEMARK OFFICE
CERTIFICATE OF CORRECTION

PATENT NO.   : 6,080,588
DATED        : June 27, 2000
INVENTOR(S)  : Gary D. Glick It is certified that error appears in the above-identified patent and that said Letters Patent is hereby corrected as shown below:

On the cover sheet, first column, line 31, replace "Antigen-Binding" with -- Antigen-binding --.

On the cover sheet, first column, line 36, replace "anti-DNA Autoantibodies" with -- anti-DNA autoantibodies --.

On page 2, under Other Publications, first column, line 20, replace "DNA Ligands" with -- DNA ligands --.

On page 2, second column, line 11, replace "Crc Press" with -- CRC Press --.

Signed and Sealed this

First Day of May, 2001

Attest:

NICHOLAS P. GODICI

Attesting Officer       Acting Director of the United States Patent and Trademark Office

SEQUENCE LISTING (1) GENERAL INFORMATION:

(iii) NUMBER OF SEQUENCES: 113

(2) INFORMATION FOR SEQ ID NO:1:

```
        (i) SEQUENCE CHARACTERISTICS:
             (A) LENGTH: 12 base pairs
             (B) TYPE: nucleic acid
             (C) STRANDEDNESS: single
             (D) TOPOLOGY: linear (ix) FEATURE:
             (A) NAME/KEY: misc_feature
             (B) LOCATION: 1
             (D) OTHER INFORMATION: /note= "Disulfide linkage with the
                 first nucleotide of SEQ ID NO:2"

(ix) FEATURE:
             (A) NAME/KEY: misc_feature
             (B) LOCATION: 12
             (D) OTHER INFORMATION: /note= "Disulfide linkage with the
                 last nucleotide of SEQ ID NO:2"

(xi) SEQUENCE DESCRIPTION: SEQ ID NO:1:

TGCGAATTCG CT                                                               12

(2) INFORMATION FOR SEQ ID NO:2:

(i) SEQUENCE CHARACTERISTICS:
             (A) LENGTH: 12 base pairs
             (B) TYPE: nucleic acid
             (C) STRANDEDNESS: single
             (D) TOPOLOGY: linear (ix) FEATURE:
             (A) NAME/KEY: misc_feature
             (B) LOCATION: 1
             (D) OTHER INFORMATION: /note= "Disulfide linkage with the
                 first nucleotide of SEQ ID NO:1"

(ix) FEATURE:
             (A) NAME/KEY: misc_feature
             (B) LOCATION: 12
             (D) OTHER INFORMATION: /note= "Disulfide linkage with the
                 last nucleotide of SEQ ID NO:1"

(xi) SEQUENCE DESCRIPTION: SEQ ID NO:2:

TCGCTTAAGC GT                                                               12

(2) INFORMATION FOR SEQ ID NO:3:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ix) FEATURE:
             (A) NAME/KEY: misc_feature
             (B) LOCATION: 1-8
             (D) OTHER INFORMATION: /note= "This is a 1 to 8 nucleotide
                 stretch of Adenine"

(ix) FEATURE:
             (A) NAME/KEY: misc_feature
             (B) LOCATION: 14-21
             (D) OTHER INFORMATION: /note= "This is a 1 to 8 nucleotide
                 stretch of Adenine"

(xi) SEQUENCE DESCRIPTION: SEQ ID NO:3:

AAAAAAAATT TTTAAAAAAA A                                                     21

(2) INFORMATION FOR SEQ ID NO:4:

(i) SEQUENCE CHARACTERISTICS:
             (A) LENGTH: 21 base pairs
             (B) TYPE: nucleic acid
```

(C) STRANDEDNESS: single
            (D) TOPOLOGY: both (ix) FEATURE:
            (A) NAME/KEY: stem_loop
            (B) LOCATION: 9..13

(xi) SEQUENCE DESCRIPTION: SEQ ID NO:4:

AGCAATCCTT TTTGGATTGC T                                              21

(2) INFORMATION FOR SEQ ID NO:5:

(i) SEQUENCE CHARACTERISTICS:
            (A) LENGTH: 334 base pairs
            (B) TYPE: nucleic acid
            (C) STRANDEDNESS: single
            (D) TOPOLOGY: linear (xi) SEQUENCE DESCRIPTION: SEQ ID NO:5:

GGCTGAACTG GTGAAGCCTG GGGCTTCAGT GAAGCTGTCC TGCAAGGCTT CTGGATACAC       60

CTTCACTAGT TACTGGATGC ACTGGGTGAA GCAGAGGCCT GGACAAGGCC TTGAGTGGAT      120

CGGAGAGATT GATCCTTCTG ATAGTTATAC TTACTACAAT CAAAAGTTCA AGGGCAAGGC      180

CACATTGACT GTAGACAAAT CCTCCAGCAC AGCCTACATG CAACTCAGCA GCCTGACATC      240

TGAGGACTCT GCGGTCTATT ACTGTGCAAA GGGGAGGCTC CGTTACTTTG CTATGGACTA      300

CTGGGGTCAA GGAACCTCAG TCACCGTCTC CTCA                                 334

(2) INFORMATION FOR SEQ ID NO:6:

(i) SEQUENCE CHARACTERISTICS:
            (A) LENGTH: 334 base pairs
            (B) TYPE: nucleic acid
            (C) STRANDEDNESS: single
            (D) TOPOLOGY: linear (xi) SEQUENCE DESCRIPTION: SEQ ID NO:6:

GGCTGAACTG GTGAAGCCTG GGGCTTCAGT GAAGCTGTCC TGCAAGGCTT CTGGATACAC       60

CTTCACTAGC TACTGGATTC ACTGGGTGAA GCAGAGGCCT GGACAAGGCC TTGAGTGGAT      120

CGGAGAGATT GATCCTTCTG ATAATTATAC TTACTACAAT CAAAAGTTCA AGGGCAAGGC      180

CACATTGACT GTAGACAAAT CCTCCAGCAC AGCCTACATG CAACTCAGCA GCCTGACATC      240

TGAGGACTCT GCGGTCTATT ACTGTGCAAA GGGGAGGCTC CGTTACTTTG CTATGGACTA      300

CTGGGGTCGA GGAACCTCAG TCACCGTCTC CTCA                                 334

(2) INFORMATION FOR SEQ ID NO:7:

(i) SEQUENCE CHARACTERISTICS:
            (A) LENGTH: 334 base pairs
            (B) TYPE: nucleic acid
            (C) STRANDEDNESS: single
            (D) TOPOLOGY: linear (xi) SEQUENCE DESCRIPTION: SEQ ID NO:7:

GGTTGAATTG GTGAAACCTG GGGCTTCAGT GAAGCTGTCC TGCAAGGCTT CTGGATACAC       60

CTTCACTAGC TACTGGATGC ATTGGGTGAA GCAGAAGCCT GGACAAGGCC TTGAGTGGAT      120

CGGAGAGATT GATCCTTCTG ATAGTTATAC TTACTACAAT CAAAAGTTCA AGGGCAAGGC      180

CACATTGACT GTAGACAAAT CCTCCAGCAC AGCCTACATG CAACTCAGCA GCCTGACATC      240

TGAGGACTCT GCGGTCTATT ACTGTGCAAA GGGGAGGCTC CGTTACTTTG CTATGGACTA      300

CTGGGGTCAA GGAACCTCAG TCACCGTCTC CTCA                                 334

(2) INFORMATION FOR SEQ ID NO:8:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (xi) SEQUENCE DESCRIPTION: SEQ ID NO:8:

GGCTGAACTG GTGAAGCCTG GGGCTTCAGT GAAGCTGTCC TGCAAGGCTT CTGGATACAC      60

GTTCACTAGA TACTGGATGC ACTGGGTGAA GCAGAGGCCT GGACAAGGCC TTGAGTGGAT     120

CGGAGAGATT GATCCTTCTG ATAGTTATAC TTACTACAAT CAAAAGTTCA AGGGCAAGGC     180

CACATTGACT GTAGACAAAT CCTCCACCAC AGCCTACATG CAACTCAGCA GCCTGACATC     240

TGAGGACTCT GCGGTCTATT ACTGTGCAAA GGGGAGGCTC CGTTACTTTG CTATGGACTA     300

CTGGGGTCAA GGAACCTCAG TCACCGTCTC CTCA                                 334

(2) INFORMATION FOR SEQ ID NO:9:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (xi) SEQUENCE DESCRIPTION: SEQ ID NO:9:

GGCTGAGCTG GCGAGGCCTG GGGCTTCAGT GAAGCTGTCC TGCAAGGCTT CTGGCTACAC      60

CTTCACAAGT TATGGTATAA GCTGGGTGAA GCAGAGAACT GGACAGGGCC TTGAGTGGAT     120

TGGAGAGATT TATCCTAGAA GTGGTAATAC TTACTACAAT GAGAAGTTCA AGGGCAAGGC     180

CACACTGACT GCAGACAAAT CCTCCAGCAC AGCCTACATG CAGCTCAGCA GCCTGACATC     240

TGAGGACTCT GCAGTCTATT TCTGTGCAAG ACAGTCCTAC TATAGTTACT ACTCCTGGTT     300

TGCTTACTGG GGCCAAGGGA CTCTGGTCAC TGTCTCTACA                           340

(2) INFORMATION FOR SEQ ID NO:10:

(i) SEQUENCE CHARACTERISTICS:
        (A) LENGTH: 349 base pairs
        (B) TYPE: nucleic acid
        (C) STRANDEDNESS: single
        (D) TOPOLOGY: linear (xi) SEQUENCE DESCRIPTION: SEQ ID NO:10:

ACCTGAGCTG GTAAAGCCTG GGGCTTCAGT GAAGATGTCC TGCAAGGCTT CTGGATACAC      60

ATTCATTAGT TATGTTATGC ACTGGGTGAA GCAGAAGCCT GGGCAGGGCC TTGAGTGGAT     120

TGGATATATT AATCCTTACA ATGAAGGTAC TAAGTACAAT GAGAAGTTCA AAGGCAAGGC     180

CACACTGACT TCAGATAAAT CCTCCAGCAC AGCCTACATG GAGCTCAGCA GCCTGACCTC     240

TGAGGACTCT GCGGTCTATT ACTGTGCAAG ATCGAGAACT CCTGCCTATT ATAGTAACTA     300

TCCCTGGTTT GCTTACTGGG GCCAAGGGAC TCTGGTCACT GTCTCTGCA                 349

(2) INFORMATION FOR SEQ ID NO:11:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (xi) SEQUENCE DESCRIPTION: SEQ ID NO:11:

```
AGCTGAGCTG GTGAAGCCTG GGGCTTCAGT GAAGATATCC TGCAAGGCTT CTGGTTACTC      60
ATTCACTGGC TACAACATGA ACTGGGTGAA GCAGAGCCAT GGAAAGAGCC TTGAGTGGAT     120
TGGAAATATT AATCCTTACT ATGGTAGTAC TAGCTACAAT CAGAAGTTCA AGGGCAAGGC     180
CACATTGACT GTAGACAAAT CTTCCAGCAC AGCCTACATG CAGCTCAACA GCCTGACATC     240
TGAGGACTCT GCAGTCTATT ACTGTGCAAG AGGCCTATGG GCTGAGAAGT ACTTTGACTA     300
CTGGGGCCAA GGCACCACTC TCACAGTCTC CTCA                                 334
```

(2) INFORMATION FOR SEQ ID NO:12:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (xi) SEQUENCE DESCRIPTION: SEQ ID NO:12:

```
ACCTGAGCTG GTGAAGCCTG GGGCTTCAGT GAAGATATCC TGCAAGGCTT CTGGATACAC      60
ATTCACTGAC TACAATATGG ACTGGGTGAA GCAGAGCCAT GGAAAGAGCC TTGAGTGGAT     120
TGGATATATT TATCCTAACA ATGGTGGTAC TGGCTACAAC CAGAAGTTAA AGAGCAAGGC     180
CACATTGACT GTAGACAAGT CCTCCAGCAC AGCCTACATG GAGCTCCACA GCCTGACATC     240
TGAGGACTCT GCAGTCTATT ACTGTGCAAG ACCGGGGTTT TACTATGCTA TGATGGACTA     300
CTGGGGTCAA GGAACCTCAG TCACCGTCTC CTCA                                 334
```

(2) INFORMATION FOR SEQ ID NO:13:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (xi) SEQUENCE DESCRIPTION: SEQ ID NO:13:

```
ACCTGTCCTG GTGGCGCCCT CACAGAGCCT GTCCATCACT TGCACTGTCT CTGGGTTTTC      60
ATTAACCAGC TATGGTGTAC ACTGGGTTCG CCAGCCTCCA GGAAAGGGTC TGGAGTGGCT     120
GGGAGTAATA TGGCCTGCTG GTGGAAGCAC AAATTATAAT TCAGCTCTCA TGTCCAGACT     180
GAGCATCAGC AAAGACAACT CCAAGAGCCA AGTTTTCTTA AAAATGAACA GTCTGCAAAC     240
TGATGACACA GCCATGTACT ACTGTGCCAA ACATCTCCCT TATGGTAACT ACGGTTACTA     300
TGCTATGGAC TACTGGGGTC AAGGAACCTC AGTCACCGTC TCCTCA                    346
```

(2) INFORMATION FOR SEQ ID NO:14:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:14:

```
Ala Glu Leu Val Lys Pro Gly Ala Ser Val Lys Leu Ser Cys Lys Ala
 1               5                  10                  15
Ser Gly Tyr Thr Phe Thr Ser Tyr Trp Met His Trp Val Lys Gln Arg
                20                  25                  30
Pro Gly Gln Gly Leu Glu Trp Ile Gly Glu Ile Asp Pro Ser Asp Ser
            35                  40                  45
```

```
Tyr Thr Tyr Tyr Asn Gln Lys Phe Lys Gly Lys Ala Thr Leu Thr Val
        50                  55                  60

Asp Lys Ser Ser Ser Thr Ala Tyr Met Gln Leu Ser Ser Leu Thr Ser
 65                  70                  75                  80

Glu Asp Ser Ala Val Tyr Tyr Cys Ala Lys Gly Arg Leu Arg Tyr Phe
                 85                  90                  95

Ala Met Asp Tyr Trp Gly Gln Gly Thr Ser Val Thr Val Ser Ser
            100                 105                 110
```

(2) INFORMATION FOR SEQ ID NO:15:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:15:

```
Ala Glu Leu Val Lys Pro Gly Ala Ser Val Lys Leu Ser Cys Lys Ala
 1               5                  10                  15

Ser Gly Tyr Thr Phe Thr Ser Tyr Trp Ile His Trp Val Lys Gln Arg
            20                  25                  30

Pro Gly Gln Gly Leu Glu Trp Ile Gly Glu Ile Asp Pro Ser Asp Asn
        35                  40                  45

Tyr Thr Tyr Tyr Asn Gln Lys Phe Lys Gly Lys Ala Thr Leu Thr Val
        50                  55                  60

Asp Lys Ser Ser Ser Thr Ala Tyr Met Gln Leu Ser Ser Leu Thr Ser
 65                  70                  75                  80

Glu Asp Ser Ala Val Tyr Tyr Cys Ala Lys Gly Arg Leu Arg Tyr Phe
                 85                  90                  95

Ala Met Asp Tyr Trp Gly Arg Gly Thr Ser Val Thr Val Ser Ser
            100                 105                 110
```

(2) INFORMATION FOR SEQ ID NO:16:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:16:

```
Val Glu Leu Val Lys Pro Gly Ala Ser Val Lys Leu Ser Cys Lys Ala
 1               5                  10                  15

Ser Gly Tyr Thr Phe Thr Ser Tyr Trp Met His Trp Val Lys Gln Lys
            20                  25                  30

Pro Gly Gln Gly Leu Glu Trp Ile Gly Glu Ile Asp Pro Ser Asp Ser
        35                  40                  45

Tyr Thr Tyr Tyr Asn Gln Lys Phe Lys Gly Lys Ala Thr Leu Thr Val
        50                  55                  60

Asp Lys Ser Ser Ser Thr Ala Tyr Met Gln Leu Ser Ser Leu Thr Ser
 65                  70                  75                  80

Glu Asp Ser Ala Val Tyr Tyr Cys Ala Lys Gly Arg Leu Arg Tyr Phe
                 85                  90                  95

Ala Met Asp Tyr Trp Gly Gln Gly Thr Ser Val Thr Val Ser Ser
            100                 105                 110
```

(2) INFORMATION FOR SEQ ID NO:17:

(i) SEQUENCE CHARACTERISTICS:
    (A) LENGTH: 111 amino acids
    (B) TYPE: amino acid
    (C) STRANDEDNESS: single
    (D) TOPOLOGY: linear (xi) SEQUENCE DESCRIPTION: SEQ ID NO:17:

Ala Glu Leu Val Lys Pro Gly Ala Ser Val Lys Leu Ser Cys Lys Ala
1               5                   10                  15

Ser Gly Tyr Thr Phe Thr Arg Tyr Trp Met His Trp Val Lys Gln Arg
            20                  25                  30

Pro Gly Gln Gly Leu Glu Trp Ile Gly Glu Ile Asp Pro Ser Asp Ser
        35                  40                  45

Tyr Thr Tyr Asn Gln Lys Phe Lys Gly Lys Ala Thr Leu Thr Val
    50                  55                  60

Asp Lys Ser Ser Thr Thr Ala Tyr Met Gln Leu Ser Ser Leu Thr Ser
65                  70                  75                  80

Glu Asp Ser Ala Val Tyr Tyr Cys Ala Lys Gly Arg Leu Arg Tyr Phe
                85                  90                  95

Ala Met Asp Tyr Trp Gly Gln Gly Thr Ser Val Thr Val Ser Ser
            100                 105                 110

(2) INFORMATION FOR SEQ ID NO:18:

(i) SEQUENCE CHARACTERISTICS:
        (A) LENGTH: 113 amino acids
        (B) TYPE: amino acid
        (C) STRANDEDNESS: single
        (D) TOPOLOGY: linear (xi) SEQUENCE DESCRIPTION: SEQ ID NO:18:

Ala Glu Leu Ala Arg Pro Gly Ala Ser Val Lys Leu Ser Cys Lys Ala
1               5                   10                  15

Ser Gly Tyr Thr Phe Thr Ser Tyr Gly Ile Ser Trp Val Lys Gln Arg
            20                  25                  30

Thr Gly Gln Gly Leu Glu Trp Ile Gly Glu Ile Tyr Pro Arg Ser Gly
        35                  40                  45

Asn Thr Tyr Tyr Asn Glu Lys Phe Lys Gly Lys Ala Thr Leu Thr Ala
    50                  55                  60

Asp Lys Ser Ser Ser Thr Ala Tyr Met Gln Leu Ser Ser Leu Thr Ser
65                  70                  75                  80

Glu Asp Ser Ala Val Tyr Phe Cys Ala Arg Gln Ser Tyr Tyr Ser Tyr
                85                  90                  95

Tyr Ser Trp Phe Ala Tyr Trp Gly Gln Gly Thr Leu Val Thr Val Ser
            100                 105                 110

Thr (2) INFORMATION FOR SEQ ID NO:19:

(i) SEQUENCE CHARACTERISTICS:
        (A) LENGTH: 116 amino acids
        (B) TYPE: amino acid
        (C) STRANDEDNESS: single
        (D) TOPOLOGY: linear (xi) SEQUENCE DESCRIPTION: SEQ ID NO:19:

Pro Glu Leu Val Lys Pro Gly Ala Ser Val Lys Met Ser Cys Lys Ala
1               5                   10                  15

Ser Gly Tyr Thr Phe Ile Ser Tyr Val Met His Trp Val Lys Gln Lys

-continued

```
                 20                  25                  30
Pro Gly Gln Gly Leu Glu Trp Ile Gly Tyr Ile Asn Pro Tyr Asn Glu
             35                  40                  45

Gly Thr Lys Tyr Asn Glu Lys Phe Lys Gly Lys Ala Thr Leu Thr Ser
     50                  55                  60

Asp Lys Ser Ser Ser Thr Ala Tyr Met Glu Leu Ser Ser Leu Thr Ser
65                  70                  75                  80

Glu Asp Ser Ala Val Tyr Tyr Cys Ala Arg Ser Arg Thr Pro Ala Tyr
                 85                  90                  95

Tyr Ser Asn Tyr Pro Trp Phe Ala Tyr Trp Gly Gln Gly Thr Leu Val
            100                 105                 110

Thr Val Ser Ala
        115
```

(2) INFORMATION FOR SEQ ID NO:20:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:20:

```
Ala Glu Leu Val Lys Pro Gly Ala Ser Val Lys Ile Ser Cys Lys Ala
1               5                  10                  15

Ser Gly Tyr Ser Phe Thr Gly Tyr Asn Met Asn Trp Val Lys Gln Ser
             20                  25                  30

His Gly Lys Ser Leu Glu Trp Ile Gly Asn Ile Asn Pro Tyr Tyr Gly
             35                  40                  45

Ser Thr Ser Tyr Asn Gln Lys Phe Lys Gly Lys Ala Thr Leu Thr Val
     50                  55                  60

Asp Lys Ser Ser Ser Thr Ala Tyr Met Gln Leu Asn Ser Leu Thr Ser
65                  70                  75                  80

Glu Asp Ser Ala Val Tyr Tyr Cys Ala Arg Gly Leu Trp Ala Glu Lys
                 85                  90                  95

Tyr Gly Asp Tyr Trp Gly Gln Gly Thr Thr Leu Thr Val Ser Ser
            100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:21:

```
Pro Glu Leu Val Lys Pro Gly Ala Ser Val Lys Ile Ser Cys Lys Ala
1               5                  10                  15

Ser Gly Tyr Thr Phe Thr Asp Tyr Asn Met Asp Trp Val Lys Gln Ser
             20                  25                  30

His Gly Lys Ser Leu Glu Trp Ile Gly Tyr Ile Tyr Pro Asn Asn Gly
             35                  40                  45

Gly Thr Gly Tyr Asn Gln Lys Leu Lys Ser Lys Ala Thr Leu Thr Val
     50                  55                  60

Asp Lys Ser Ser Ser Thr Ala Tyr Met Glu Leu His Ser Leu Thr Ser
65                  70                  75                  80

Glu Asp Ser Ala Val Tyr Tyr Cys Ala Arg Pro Gly Phe Tyr Tyr Ala
```

```
                    85                    90                    95
Met Met Asp Tyr Trp Gly Gln Gly Thr Ser Val Thr Val Ser Ser
                100                   105                   110

(2) INFORMATION FOR SEQ ID NO:22:

(i) SEQUENCE CHARACTERISTICS:
        (A) LENGTH: 115 amino acids
        (B) TYPE: amino acid
        (C) STRANDEDNESS: single
        (D) TOPOLOGY: linear (xi) SEQUENCE DESCRIPTION: SEQ ID NO:22:

Pro Val Leu Val Ala Pro Ser Gln Ser Leu Ser Ile Thr Cys Thr Val
1               5                   10                  15

Ser Gly Phe Ser Leu Thr Ser Tyr Gly Val His Trp Val Arg Gln Pro
            20                  25                  30

Pro Gly Lys Gly Leu Glu Trp Leu Gly Val Ile Trp Pro Ala Gly Gly
        35                  40                  45

Ser Thr Asn Tyr Asn Ser Ala Leu Met Ser Arg Leu Ser Ile Ser Lys
    50                  55                  60

Asp Asn Ser Lys Ser Gln Val Phe Leu Lys Met Asn Ser Leu Gln Thr
65                  70                  75                  80

Asp Asp Thr Ala Met Tyr Tyr Cys Ala Lys His Leu Pro Tyr Gly Asn
                85                  90                  95

Tyr Gly Tyr Tyr Ala Met Asp Tyr Trp Gly Gln Gly Thr Ser Val Thr
                100                 105                 110

Val Ser Ser
        115

(2) INFORMATION FOR SEQ ID NO:23:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:23:

GCCTCCCTAT CTGCATCTGT GGGAGAAACT GTCACCATCA CATGTCGAGC AAGTGAGAAT        60

ATTTACAGTT ATTTAGCATG GTATCAGCAG AAACAGGGAA AATCTCCTCA GCTCCTGGTC       120

TATAATGCAA AAATTTTAGC AGAAGGTGTG CCATCAAGGT TCAGTGGCAG TGGATCAGGC       180

ACACAGTTTT CTCTGAAGAT CAACAGCCTG CAGCCTGAAG ATTTTGGGAG TTATTACTGT       240

CAACATCATT ATGGTACTCC ATTCACGTTC GGCACGGGGA CAAAATTGGA AATAAAA         297

(2) INFORMATION FOR SEQ ID NO:24:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:24:

GCCTCCCTAT CTGCATCTGT GGGAGAAACT GTCACCATCA CATGTCGAGC AAGTGAGAAT        60

ATTTACAGTT ATTTAGCATG GTATCAGCAG AAACAGGGAA AATCTCCTCA GCTCCTGGTC       120

TATAATGCAA AAACCTTAGC AGAAGGTGTG CCATCAAGGT TCAGTGGCAG TGGATCAGGC       180

ACACAGTTTT CTCTGAAGAT CAACAGCCTG CAGCCTGAAG ATTTTGGGAG TTATTACTGT       240
```

CAACATCATT ATGGTACTCC ATTCACGTTC GGCACGGGGA CAAAATTGGA AATAAAA     297

(2) INFORMATION FOR SEQ ID NO:25:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:25:

GTTTCCCTAT CTGCATCTGT GGGAGAAACT GTCACCATCA CATGTCGAGC AAGTGAGAAT     60

ATTTACAGTT ATTTAGCATG GTATCAGCAG AAACAGGGAA AATCTCCTCA GCTCCTGGTC     120

TATAATGCAA AAACCTTAGC AGAAGGTGTG CCATCAAGGT TCAGTGGCAG TGGATCAGGC     180

ACACAGTTTT CTCTGAAGAT CAACAGCCTG CAGCCTGAAG ATTTTGGGAG TTATTACTGT     240

CAACATCATT ATGGTACTCC ATTCACGTTC GGCACGGGGA CAAAATTGGA AATAAAA     297

(2) INFORMATION FOR SEQ ID NO:26:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:26:

GCCTCCCTAT CTGCATCTGT GGGAGAAACT GTCACCATCA CATGTCGAGC AAGTGAGAAT     60

ATTTACAGTT ATTTAGCATG GTATCAGCAG AAACAGGGAA AATCTCCTCA GCTCCTGGTC     120

TATAATGCAA AAACCTTAGC AGAAGGTGTG CCATCAAGGT TCAGTGGCAG TGGATCAGGC     180

ACACAGTTTT CTCTGAAGAT CAACAGCCTG CAGCCTGAAG ATTTTGGGAG TTATTACTGT     240

CAACATCATT ATGGTACTCC ATTCACGTTC GGCACGGGGA CAAAATTGGA AATAAAA     297

(2) INFORMATION FOR SEQ ID NO:27:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO:27:

GCAATCATGG CTGCATCTCC AGGGGAGAAG GTCACCATGA CCTGCAGTGC CAGCTCAAGT     60

GTAAGTTCTG GTAACTTTCA CTGGTACCAG CAGAAGCCAG GCACTTCTCC CAAACTCTGG     120

ATTTATAGGA CATCCAACCT GGCTTCTGGA GTCCCCGCTC GCTTCAGTGG CAGTGGGTCT     180

GGGACCTCTT ACTCTCTTAC AATCAGCAGC ATGGAGGCCG AAGATGCTGC CACTTATTAC     240

TGCCAGCAGT GGAGTGGTTA CCCACGGACG TTCGGTGGAG GCACCAAGCT GGAAATCAAA     300

(2) INFORMATION FOR SEQ ID NO:28:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (xi) SEQUENCE DESCRIPTION: SEQ ID NO:28:

CTCTCCCTGC CTGTCAGTCT TGGAGATCAA GCCTCCATCT CTTGCAGATC TAGTCAGAGC     60

```
CTTGTACACA ATAATGGAAA CACCTATCTA CATTGGTACC TGCAGAAGCC AGGCCAGTCT      120

CCAAAGCTCC TAGTCTACAA AGTTTCCAAC CGATTTTCTG GGGTGCCAGA CAGGTTCAGT      180

GGCAGTGGAT CAGGGACAGA TTTCACACTC AAGATCAGCA GAGTGGAGGC TGAGGATCTG      240

GGAGTTTATT TCTGCTCTCA AAGTACACAT GTTCCTCCGA CGTTCGGTGG AGGCACCAAG      300

CTGGAAATCA AA                                                          312

(2) INFORMATION FOR SEQ ID NO:29:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (xi) SEQUENCE DESCRIPTION: SEQ ID NO:29:

GCATCTTTGG CTGAGTCTCT AGGGCAGAAG GCCACCATCT CCTGCAAGGC CAGCAAAAAA       60

GTCACTATAT TTGGCTCTAT AAGTGCTCTA CACTGGTACC AACAGAAACC AGGACAGCCA      120

CCCAAACTCN NNATCTATAA TGGAGCCAAA CTAGAATCTG GGGTCAGTGC CAGGTTCAGT      180

GACAGTGGGT CTNNNNNNNN NTTCACCCTC ACCATTGATC CTGTGGAGGC TGATGATGCA      240

GCAACCTATT ACTGTCTGCA AAATAAAGAG GTTCCGTATA CGTTCGGATC GGGGACCAAG      300

CTGGAAATAA AA                                                          312

(2) INFORMATION FOR SEQ ID NO:30:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (xi) SEQUENCE DESCRIPTION: SEQ ID NO:30:

GCAATCATGG CTGCATCTCC AGGGGAGAAG GTCACCATGA CCTGCAGTGC CAGCTCAAGT       60

GTAAGTCCTG GTAACTTTCA CTGGTACCAG CAGAAGCCAG GCCCTTCTCC CAAACTCTGG      120

ATTTATAGGA CATCCAACCT GGCTTCTGGA GTCCCCGCTC GCTTCAGTGG CAGTGGGTCT      180

GGGACCTCTT ACTCTCTTAC AATCAGCAGT ATGGAGGCCG AAGACGCTGC CACTTATTAC      240

TGCCAGCAGT GGAGTGGTTA CCCACGGACG TTCGGTGGAG GCACCAAGCT GGAAATCAAA      300

(2) INFORMATION FOR SEQ ID NO:31:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO:31:

GCTTCTTTGG CTGTGTCTCT AGGGCAGAGT GTCACCATCT CCTGCAGAGC CAGTGAAAGT       60

GTTGAATATT ATGGCACTAG TTTAATGCAG TGGTACCAAC AGAAACCAGG ACAGCCACCC      120

AAACTCCTCA TCTATGGTGC ATCCAACGTA GAATCTGGGG TCCCTGCCAG GTTTAGTGGC      180

AGTGGGTCTG GGACAGACTT CAGCCTCAAC ATCCATCCTG TGGAGGAGGA TGATATTGCA      240

ATGTATTTCT GTCAGCAAAG TAGGAAGGTT CCTTCGACGT TCGGTGGAGG CACCAAGCTG      300

GAAATCAAA                                                              309

(2) INFORMATION FOR SEQ ID NO:32:
```

(i) SEQUENCE CHARACTERISTICS:
    (A) LENGTH: 99 amino acids
    (B) TYPE: amino acid
    (C) STRANDEDNESS: single
    (D) TOPOLOGY: linear (xi) SEQUENCE DESCRIPTION: SEQ ID NO:32:

```
Ala Ser Leu Ser Ala Ser Val Gly Glu Thr Val Thr Ile Thr Cys Arg
1               5                   10                  15

Ala Ser Glu Asn Ile Tyr Ser Tyr Leu Ala Trp Tyr Gln Gln Lys Gln
            20                  25                  30

Gly Lys Ser Pro Gln Leu Leu Val Tyr Asn Ala Lys Ile Leu Ala Glu
            35                  40                  45

Gly Val Pro Ser Arg Phe Ser Gly Ser Gly Ser Gly Thr Gln Phe Ser
    50                  55                  60

Leu Lys Ile Asn Ser Leu Gln Pro Glu Asp Phe Gly Ser Tyr Tyr Cys
65                  70                  75                  80

Gln His His Tyr Gly Thr Pro Phe Thr Phe Gly Thr Gly Thr Lys Leu
                85                  90                  95

Glu Ile Lys
```

(2) INFORMATION FOR SEQ ID NO:33:

(i) SEQUENCE CHARACTERISTICS:
    (A) LENGTH: 99 amino acids
    (B) TYPE: amino acid
    (C) STRANDEDNESS: single
    (D) TOPOLOGY: linear (xi) SEQUENCE DESCRIPTION: SEQ ID NO:33:

```
Ala Ser Leu Ser Ala Ser Val Gly Glu Thr Val Thr Ile Thr Cys Arg
1               5                   10                  15

Ala Ser Glu Asn Ile Tyr Ser Tyr Leu Ala Trp Tyr Gln Gln Lys Gln
            20                  25                  30

Gly Lys Ser Pro Gln Leu Leu Val Tyr Asn Ala Lys Thr Leu Ala Glu
            35                  40                  45

Gly Val Pro Ser Arg Phe Ser Gly Ser Gly Ser Gly Thr Gln Phe Ser
    50                  55                  60

Leu Lys Ile Asn Ser Leu Gln Pro Glu Asp Phe Gly Ser Tyr Tyr Cys
65                  70                  75                  80

Gln His His Tyr Gly Thr Pro Phe Thr Phe Gly Thr Gly Thr Lys Leu
                85                  90                  95

Glu Ile Lys
```

(2) INFORMATION FOR SEQ ID NO:34:

(i) SEQUENCE CHARACTERISTICS:
    (A) LENGTH: 99 amino acids
    (B) TYPE: amino acid
    (C) STRANDEDNESS: single
    (D) TOPOLOGY: linear (xi) SEQUENCE DESCRIPTION: SEQ ID NO:34:

```
Val Ser Leu Ser Ala Ser Val Gly Glu Thr Val Thr Ile Thr Cys Arg
1               5                   10                  15

Ala Ser Glu Asn Ile Tyr Ser Tyr Leu Ala Trp Tyr Gln Gln Lys Gln
            20                  25                  30

Gly Lys Ser Pro Gln Leu Leu Val Tyr Asn Ala Lys Thr Leu Ala Glu
            35                  40                  45
```

Gly Val Pro Ser Arg Phe Ser Gly Ser Gly Ser Gly Thr Gln Phe Ser
    50                  55                  60

Leu Lys Ile Asn Ser Leu Gln Pro Glu Asp Phe Gly Ser Tyr Tyr Cys
65                  70                  75                  80

Gln His His Tyr Gly Thr Pro Phe Thr Phe Gly Thr Gly Thr Lys Leu
                85                  90                  95

Glu Ile Lys (2) INFORMATION FOR SEQ ID NO:35:

(i) SEQUENCE CHARACTERISTICS:
        (A) LENGTH: 99 amino acids
        (B) TYPE: amino acid
        (C) STRANDEDNESS: single
        (D) TOPOLOGY: linear (xi) SEQUENCE DESCRIPTION: SEQ ID NO:35:

Ala Ser Leu Ser Ala Ser Val Gly Glu Thr Val Thr Ile Thr Cys Arg
1               5                   10                  15

Ala Ser Glu Asn Ile Tyr Ser Tyr Leu Ala Trp Tyr Gln Gln Lys Gln
                20                  25                  30

Gly Lys Ser Pro Gln Leu Leu Val Tyr Asn Ala Lys Thr Leu Ala Glu
            35                  40                  45

Gly Val Pro Ser Arg Phe Ser Gly Ser Gly Ser Gly Thr Gln Phe Ser
    50                  55                  60

Leu Lys Ile Asn Ser Leu Gln Pro Glu Asp Phe Gly Ser Tyr Tyr Cys
65                  70                  75                  80

Gln His His Tyr Gly Thr Pro Phe Thr Phe Gly Thr Gly Thr Lys Leu
                85                  90                  95

Glu Ile Lys (2) INFORMATION FOR SEQ ID NO:36:

(i) SEQUENCE CHARACTERISTICS:
        (A) LENGTH: 100 amino acids
        (B) TYPE: amino acid
        (C) STRANDEDNESS: single
        (D) TOPOLOGY: linear (xi) SEQUENCE DESCRIPTION: SEQ ID NO:36:

Ala Ile Met Ala Ala Ser Pro Gly Glu Lys Val Thr Met Thr Cys Ser
1               5                   10                  15

Ala Ser Ser Ser Val Ser Ser Gly Asn Phe His Trp Tyr Gln Gln Lys
                20                  25                  30

Pro Gly Thr Ser Pro Lys Leu Trp Ile Tyr Arg Thr Ser Asn Leu Ala
            35                  40                  45

Ser Gly Val Pro Ala Arg Phe Ser Gly Ser Gly Ser Gly Thr Ser Tyr
    50                  55                  60

Ser Leu Thr Ile Ser Ser Met Glu Ala Glu Asp Ala Ala Thr Tyr Tyr
65                  70                  75                  80

Cys Gln Gln Trp Ser Gly Tyr Pro Arg Thr Phe Gly Gly Gly Thr Lys
                85                  90                  95

Leu Glu Ile Lys
            100

(2) INFORMATION FOR SEQ ID NO:37:

(i) SEQUENCE CHARACTERISTICS:

(A) LENGTH: 104 amino acids
(B) TYPE: amino acid
(C) STRANDEDNESS: single
(D) TOPOLOGY: linear (xi) SEQUENCE DESCRIPTION: SEQ ID NO:37:

```
Leu Ser Leu Pro Val Ser Leu Gly Asp Gln Ala Ser Ile Ser Cys Arg
1               5                  10                  15

Ser Ser Gln Ser Leu Val His Asn Asn Gly Asn Thr Tyr Leu His Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
50                  55                  60

Gly Thr Asp Phe Thr Leu Lys Ile Ser Arg Val Glu Ala Glu Asp Leu
65                  70                  75                  80

Gly Val Tyr Phe Cys Ser Gln Ser Thr His Val Pro Pro Thr Phe Gly
                85                  90                  95

Gly Gly Thr Lys Leu Glu Ile Lys
            100
```

(2) INFORMATION FOR SEQ ID NO:38:

(i) SEQUENCE CHARACTERISTICS:
(A) LENGTH: 104 amino acids
(B) TYPE: amino acid
(C) STRANDEDNESS: single
(D) TOPOLOGY: linear (ix) FEATURE:
(A) NAME/KEY: Modified-site
(B) LOCATION: group(44, 65, 66, 67)
(D) OTHER INFORMATION: /product= "OTHER"
/note= "Unknown amino acids"

(xi) SEQUENCE DESCRIPTION: SEQ ID NO:38:

```
Ala Ser Leu Ala Glu Ser Leu Gly Gln Lys Ala Thr Ile Ser Cys Lys
1               5                  10                  15

Ala Ser Lys Lys Val Thr Ile Phe Gly Ser Ile Ser Ala Leu His Trp
            20                  25                  30

Tyr Gln Gln Lys Pro Gly Gln Pro Pro Lys Leu Xaa Ile Tyr Asn Gly
        35                  40                  45

Ala Lys Leu Glu Ser Gly Val Ser Ala Arg Phe Ser Asp Ser Gly Ser
50                  55                  60

Xaa Xaa Xaa Phe Thr Leu Thr Ile Asp Pro Val Glu Ala Asp Asp Ala
65                  70                  75                  80

Ala Thr Tyr Tyr Cys Leu Gln Asn Lys Glu Val Pro Tyr Thr Phe Gly
                85                  90                  95

Ser Gly Thr Lys Leu Glu Ile Lys
            100
```

(2) INFORMATION FOR SEQ ID NO:39:

(i) SEQUENCE CHARACTERISTICS:
(A) LENGTH: 100 amino acids
(B) TYPE: amino acid
(C) STRANDEDNESS: single
(D) TOPOLOGY: linear (xi) SEQUENCE DESCRIPTION: SEQ ID NO:39:

```
Ala Ile Met Ala Ala Ser Pro Gly Glu Lys Val Thr Met Thr Cys Ser
1               5                  10                  15
```

```
Ala Ser Ser Ser Val Ser Pro Gly Asn Phe His Trp Tyr Gln Gln Lys
            20                  25                  30

Pro Gly Pro Ser Pro Lys Leu Trp Ile Tyr Arg Thr Ser Asn Leu Ala
        35                  40                  45

Ser Gly Val Pro Ala Arg Phe Ser Gly Ser Gly Ser Gly Thr Ser Tyr
    50                  55                  60

Ser Leu Thr Ile Ser Ser Met Glu Ala Glu Asp Ala Ala Thr Tyr Tyr
65                  70                  75                  80

Cys Gln Gln Trp Ser Gly Tyr Pro Arg Thr Phe Gly Gly Gly Thr Lys
                85                  90                  95

Leu Glu Ile Lys
            100

(2) INFORMATION FOR SEQ ID NO:40:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO:40:

Ala Ser Leu Ala Val Ser Leu Gly Gln Ser Val Thr Ile Ser Cys Arg
1               5                   10                  15

Ala Ser Glu Ser Val Glu Tyr Tyr Gly Thr Ser Leu Met Gln Trp Tyr
            20                  25                  30

Gln Gln Lys Pro Gly Gln Pro Pro Lys Leu Leu Ile Tyr Gly Ala Ser
        35                  40                  45

Asn Val Glu Ser Gly Val Pro Ala Arg Phe Ser Gly Ser Gly Ser Gly
    50                  55                  60

Thr Asp Phe Ser Leu Asn Ile His Pro Val Glu Glu Asp Asp Ile Ala
65                  70                  75                  80

Met Tyr Phe Cys Gln Gln Ser Arg Lys Val Pro Ser Thr Phe Gly Gly
                85                  90                  95

Gly Thr Lys Leu Glu Ile Lys
            100

(2) INFORMATION FOR SEQ ID NO:41:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:41:

CAGGTCCAGC TGCAGCAGCC TGGGGCTGAA CTGGTGAAGC CTGGGGCTTC AGTGAAGCTG      60

TCCTGCAAGG CTTCTGGATA CACCTTCACT AGCTACTGGA TGCACTGGGT GAAGCAGAGG     120

CCTGGACAAG GCCTTGAGTG GATCGGAGAG ATTGATCCTT CTGATAGTTA TACTTACTAC     180

AATCAAAAGT TCAAGGGCAA GGCCACATTG ACTGTAGACA AATCCTCCAG CACAGCCTAC     240

ATGCAACTCA GCAGCCTGAC ATCTGAGGAC TCTGCGGTCT ATTACTGTGC AAAG           294

(2) INFORMATION FOR SEQ ID NO:42:

(i) SEQUENCE CHARACTERISTICS:
        (A) LENGTH: 357 base pairs
        (B) TYPE: nucleic acid
        (C) STRANDEDNESS: single
```

(D) TOPOLOGY: linear (xi) SEQUENCE DESCRIPTION: SEQ ID NO:42:

```
CAGGTCCAGC TGCTCGAGTC TGGGGCTGAA CTGGTGAAGC CTGGGGCTTC AGTGAAGCTG      60

TCCTGCAAGG CTTCTGGATA CACCTTCACT AGCTACTGGA TTCACTGGGT GAAGCAGAGG     120

CCTGGACAAG GCCTTGAGTG GATCGGAGAG ATTGATCCTT CTGATAATTA TACTTACTAC     180

AATCAAAAGT TCAAGGGCAA GGCCACATTG ACTGTAGACA AATCCTCCAG CACAGCCTAC     240

ATGCAACTCA GCAGCCTGAC ATCTGAGGAC TCTGCGGTCT ATTACTGTGC AAAGGGGAGG     300

CTCCGTTACT TTGCTATGGA CTACTGGGGT CGAGGAACCT CAGTCACCGT CTCCTCA       357
```

(2) INFORMATION FOR SEQ ID NO:43:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (xi) SEQUENCE DESCRIPTION: SEQ ID NO:43:

```
CAGGTCCAGC TGCTCGAGTC TGGGGTTGAA TTGGTGAAAC CTGGGGCTTC AGTGAAGCTG      60

TCCTGCAAGG CTTCTGGATA CACCTTCACT AGCTACTGGA TGCATTGGGT GAAGCAGAAG     120

CCTGGACAAG GCCTTGAGTG GATCGGAGAG ATTGATCCTT CTGATAGTTA TACTTACTAC     180

AATCAAAAGT TCAAGGGCAA GGCCACATTG ACTGTAGACA AATCCTCCAG CACAGCCTAC     240

ATGCAACTCA GCAGCCTGAC ATCTGAGGAC TCTGCGGTCT ATTACTGTGC AAAGGGGAGG     300

CTCCGTTACT TTGCTATGGA CTACTGGGGT CAAGGAACCT CAGTCACCGT CTCCTCA       357
```

(2) INFORMATION FOR SEQ ID NO:44:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (xi) SEQUENCE DESCRIPTION: SEQ ID NO:44:

```
CAGGTCCAGC TGCTCGAGTC TGGGGCTGAA CTGGTGAAGC CTGGGGCTTC AGTGAAGCTG      60

TCCTGCAAGG CTTCTGGATA CACCTTCACT AGTTACTGGA TGCACTGGGT GAAGCAGAGG     120

CCTGGACAAG GCCTTGAGTG GATCGGAGAG ATTGATCCTT CTGATAGTTA TACTTACTAC     180

AATCAAAAGT TCAAGGGCAA GGCCACATTG ACTGTAGACA AATCCTCCAG CACAGCCTAC     240

ATGCAACTCA GCAGCCTGAC ATCTGAGGAC TCTGCGGTCT ATTACTGTGC AAAGGGGAGG     300

CTCCGTTACT TTGCTATGGA CTACTGGGGT CAAGGAACCT CAGTCACCGT CTCCTCA       357
```

(2) INFORMATION FOR SEQ ID NO:45:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (xi) SEQUENCE DESCRIPTION: SEQ ID NO:45:

```
CAGGTCCAGC TGCTCGAGTC TGGGGCTGAA CTGGTGAAGC CTGGGGCTTC AGTGAAGCTG      60

TCCTGCAAGG CTTCTGGATA CACGTTCACT AGATACTGGA TGCACTGGGT GAAGCAGAGG     120

CCTGGACAAG GCCTTGAGTG GATCGGAGAG ATTGATCCTT CTGATAGTTA TACTTACTAC     180
```

```
AATCAAAAGT TCAAGGGCAA GGCCACATTG ACTGTAGACA AATCCTCCAC CACAGCCTAC      240

ATGCAACTCA GCAGCCTGAC ATCTGAGGAC TCTGCGGTCT ATTACTGTGC AAAGGGGAGG      300

CTCCGTTACT TTGCTATGGA CTACTGGGGT CAAGGAACCT CAGTCACCGT CTCCTCA         357
```

(2) INFORMATION FOR SEQ ID NO:46:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:46:

```
CAGGTCCAGC TGCAGCAGTC TGGAGCTGAG CTGGCGAGGC CTGGGGCTTC AGTGAAGCTG       60

TCCTGCAAGG CTTCTGGCTA CACCTTCACA AGCTATGGTA TAAGCTGGGT GAAGCAGAGA      120

ACTGGACAGG GCCTTGAGTG GATTGGAGAG ATTTATCCTG GAAGTGGTAA TACTTACTAC      180

AATGAGAAGT TCAAGGGCAA GGCCACACTG ACTGCAGACA AATCCTCCAG CACAGCCTAC      240

ATGCAGCTCA GCAGCCTGAC ATCTGAGGAC TCTGCAGTCT ATTTCTGTGC AAGA            294
```

(2) INFORMATION FOR SEQ ID NO:47:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (xi) SEQUENCE DESCRIPTION: SEQ ID NO:47:

```
CAGGTCCAGC TGCTCGAGTC TGGGGCTGAG CTGGCGAGGC CTGGGGCTTC AGTGAAGCTG       60

TCCTGCAAGG CTTCTGGCTA CACCTTCACA AGTTATGGTA TAAGCTGGGT GAAGCAGAGA      120

ACTGGACAGG GCCTTGAGTG GATTGGAGAG ATTTATCCTA GAAGTGGTAA TACTTACTAC      180

AATGAGAAGT TCAAGGGCAA GGCCACACTG ACTGCAGACA AATCCTCCAG CACAGCCTAC      240

ATGCAGCTCA GCAGCCTGAC ATCTGAGGAC TCTGCAGTCT ATTTCTGTGC AAGACAGTCC      300

TACTATAGTT ACTACTCCTG GTTTGCTTAC TGGGGCCAAG GGACTCTGGT CACTGTCTCT      360

ACA                                                                   363
```

(2) INFORMATION FOR SEQ ID NO:48:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (xi) SEQUENCE DESCRIPTION: SEQ ID NO:48:

```
CAGGTGCAGC TGAAGGAGTC AGGACCTGGC CTGGTGGCGC CCTCACAGAG CCTGTCCATC       60

ACTTGCACTG TCTCTGGGTT TTCATTAACC AGCTATGGTG TACACTGGGT TCGCCAGCCT      120

CCAGGAAAGG GTCTGGAGTG GCTGGGAGTA ATATGGGCTG GTGGAAGCAC AAATTATAAT      180

TCGGCTCTCA TGTCCAGACT GAGCATCAGC AAAGACAACT CCAAGAGCCA AGTTTTCTTA      240

AAAATGAACA GTCTGCAAAC TGATGACACA GCCATGTACT ACTGTGCCAG A               291
```

(2) INFORMATION FOR SEQ ID NO:49:

(i) SEQUENCE CHARACTERISTICS:
        (A) LENGTH: 366 base pairs
        (B) TYPE: nucleic acid

```
            (C) STRANDEDNESS: single
            (D) TOPOLOGY: linear (xi) SEQUENCE DESCRIPTION: SEQ ID NO:49:

CAGGTCCAGC TGCTCGAGTC AGGACCTGTC CTGGTGGCGC CCTCACAGAG CCTGTCCATC      60

ACTTGCACTG TCTCTGGGTT TTCATTAACC AGCTATGGTG TACACTGGGT TCGCCAGCCT     120

CCAGGAAAGG GTCTGGAGTG GCTGGGAGTA ATATGGGCTG GTGGAAGCAC AAATTATAAT     180

TCAGCTCTCA TGTCCAGACT GAGCATCAGC AAAGACAACT CCAAGAGCCA AGTTTTCTTA     240

AAAATGAACA GTCTGCAAAC TGATGACACA GCCATGTACT ACTGTGCCAA ACATCTCCCT     300

TATGGTAACT ACGGTTACTA TGCTATGGAC TACTGGGGTC AAGGAACCTC AGTCACCGTC     360

TCCTCA                                                                366

(2) INFORMATION FOR SEQ ID NO:50:

(i) SEQUENCE CHARACTERISTICS:
            (A) LENGTH: 284 base pairs
            (B) TYPE: nucleic acid
            (C) STRANDEDNESS: single
            (D) TOPOLOGY: linear (xi) SEQUENCE DESCRIPTION: SEQ ID NO:50:

GACATCCAGA TGACTCAGTC TCCAGCCTCC CTATCTGCAT CTGTGGGAGA AACTGTCACC      60

ATCACATGTC GAGCAAGTGA GAATATTTAC AGTTATTTAG CATGGTATCA GCAGAAACAG     120

GGAAAATCTC CTCAGCTCCT GGTCTATAAT GCAAAAACCT TAGCAGAAGG TGTGCCATCA     180

AGGTTCAGTG GCAGTGGATC AGGCACACAG TTTTCTCTGA AGATCAACAG CCTGCAGCCT     240

GAAGATTTTG GGAGTTATTA CTGTCAACAT CATTATGGTA CTCC                      284

(2) INFORMATION FOR SEQ ID NO:51:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (xi) SEQUENCE DESCRIPTION: SEQ ID NO:51:

GAGCTCGTGA TGACCCAGTC TCCAGCCTCC CTATCTGCAT CTGTGGGAGA AACTGTCACC      60

ATCACATGTC GAGCAAGTGA GAATATTTAC AGTTATTTAG CATGGTATCA GCAGAAACAG     120

GGAAAATCTC CTCAGCTCCT GGTCTATAAT GCAAAAACCT TAGCAGAAGG TGTGCCATCA     180

AGGTTCAGTG GCAGTGGATC AGGCACACAG TTTTCTCTGA AGATCAACAG CCTGCAGCCT     240

GAAGATTTTG GGAGTTATTA CTGTCAACAT CATTATGGTA CTCCATTCAC GTTCGGCACG     300

GGGACAAAAT TGGAAATAAA A                                               321

(2) INFORMATION FOR SEQ ID NO:52:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (xi) SEQUENCE DESCRIPTION: SEQ ID NO:52:

GAGCTCGTGA TGACCCAGTC TCCAGTTTCC CTATCTGCAT CTGTGGGAGA AACTGTCACC      60

ATCACATGTC GAGCAAGTGA GAATATTTAC AGTTATTTAG CATGGTATCA GCAGAAACAG     120

GGAAAATCTC CTCAGCTCCT GGTCTATAAT GCAAAAACCT TAGCAGAAGG TGTGCCATCA     180
```

```
AGGTTCAGTG GCAGTGGATC AGGCACACAG TTTTCTCTGA AGATCAACAG CCTGCAGCCT      240

GAAGATTTTG GGAGTTATTA CTGTCAACAT CATTATGGTA CTCCATTCAC GTTCGGCACG      300

GGGACAAAAT TGGAAATAAA A                                                321
```

(2) INFORMATION FOR SEQ ID NO:53:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:53:

```
GAGCTCGTGA TGACCCAGTC TCCAGCCTCC CTATCTGCAT CTGTGGGAGA AACTGTCACC       60

ATCACATGTC GAGCAAGTGA GAATATTTAC AGTTATTTAG CATGGTATCA GCAGAAACAG      120

GGAAAATCTC CTCAGCTCCT GGTCTATAAT GCAAAAATTT TAGCAGAAGG TGTGCCATCA      180

AGGTTCAGTG GCAGTGGATC AGGCACACAG TTTTCTCTGA AGATCAACAG CCTGCAGCCT      240

GAAGATTTTG GGAGTTATTA CTGTCAACAT CATTATGGTA CTCCATTCAC GTTCGGCACG      300

GGGACAAAAT TGGAAATAAA A                                                321
```

(2) INFORMATION FOR SEQ ID NO:54:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:54:

```
GAGCTCGTGA TGACCCAGTC TCCAGCCTCC CTATCTGCAT CTGTGGGAGA AACTGTCACC       60

ATCACATGTC GAGCAAGTGA GAATATTTAC AGTTATTTAG CATGGTATCA GCAGAAACAG      120

GGAAAATCTC CTCAGCTCCT GGTCTATAAT GCAAAAACCT TAGCAGAAGG TGTGCCATCA      180

AGGTTCAGTG GCAGTGGATC AGGCACACAG TTTTCTCTGA AGATCAACAG CCTGCAGCCT      240

GAAGATTTTG GGAGTTATTA CTGTCAACAT CATTATGGTA CTCCATTCAC GTTCGGCACG      300

GGGACAAAAT TGGAAATAAA A                                                321
```

(2) INFORMATION FOR SEQ ID NO:55:

(i) SEQUENCE CHARACTERISTICS:
        (A) LENGTH: 287 base pairs
        (B) TYPE: nucleic acid
        (C) STRANDEDNESS: single
        (D) TOPOLOGY: linear (xi) SEQUENCE DESCRIPTION: SEQ ID NO:55:

```
GAAAATGTGC TGACCCAGTC TCCAGCAATC ATGGCTGCAT CTCCAGGGGA GAAGGTCACC       60

ATGACCTGCA GTGCCAGCTC AAGTGTAAGT TCTGGTAACT TCACTGGTA CCAGCAGAAG       120

CCAGGCACTT CTCCCAAACT CTGGATTTAT AGGACATCCA ACCTGGCTTC TGGAGTCCCC      180

GCTCGCTTCA GTGGCAGTGG GTCTGGGACC TCTTACTCTC TTACAATCAG CAGCATGGAG      240

GCCGAAGATG CTGCCACTTA TTACTGCCAG CAGTGGAGTG GTTACCC                    287
```

(2) INFORMATION FOR SEQ ID NO:56:

(i) SEQUENCE CHARACTERISTICS:
        (A) LENGTH: 324 base pairs (B) TYPE: nucleic acid
            (C) STRANDEDNESS: single
            (D) TOPOLOGY: linear (xi) SEQUENCE DESCRIPTION: SEQ ID NO:56:

GAGCTCGTGA TGACCCAGTC TCCAGCAATC ATGGCTGCAT CTCCAGGGGA GAAGGTCACC      60

ATGACCTGCA GTGCCAGCTC AAGTGTAAGT TCTGGTAACT TTCACTGGTA CCAGCAGAAG     120

CCAGGCACTT CTCCCAAACT CTGGATTTAT AGGACATCCA ACCTGGCTTC TGGAGTCCCC     180

GCTCGCTTCA GTGGCAGTGG GTCTGGGACC TCTTACTCTC TTACAATCAG CAGCATGGAG     240

GCCGAAGATG CTGCCACTTA TTACTGCCAG CAGTGGAGTG GTTACCCACG ACGTTCGGT      300

GGAGGCACCA AGCTGGAAAT CAAA                                            324

(2) INFORMATION FOR SEQ ID NO:57:

(i) SEQUENCE CHARACTERISTICS:
            (A) LENGTH: 295 base pairs
            (B) TYPE: nucleic acid
            (C) STRANDEDNESS: single
            (D) TOPOLOGY: linear (xi) SEQUENCE DESCRIPTION: SEQ ID NO:57:

GACATTGTGC TCACCCAATC TCCAGCTTCT TTGGCTGTGT CTCTAGGGCA GAGTGTCACC      60

ATCTCCTGCA GAGCCAGTGA AAGTGTTGAA TATTATGGCA CAAGTTTAAT GCAGTGGTAC     120

CAACAGAAAC CAGGACAGCC ACCCAAACTC CTCATCTATG CTGCATCCAA CGTAGAATCT     180

GGGGTCCCTG CCAGGTTTAG TGGCAGTGGG TCTGGACAGA CTTCAGCCTC AACATCCATC     240

CTGTGGAGGA GGATGATATT GCAATGTATT TCTGTCAGCA AAGTAGGAAG GTTCC          295

(2) INFORMATION FOR SEQ ID NO:58:

(i) SEQUENCE CHARACTERISTICS:
            (A) LENGTH: 332 base pairs
            (B) TYPE: nucleic acid
            (C) STRANDEDNESS: single
            (D) TOPOLOGY: linear (xi) SEQUENCE DESCRIPTION: SEQ ID NO:58:

GACATCGAGC TCACTCAGTC TCCAGCTTCT TTGGCTGTGT CTCTAGGGCA GAGTGTCACC      60

ATCTCCTGCA GAGCCAGTGA AAGTGTTGAA TATTATGGCA CTAGTTTAAT GCAGTGGTAC     120

CAACAGAAAC CAGGACAGCC ACCCAAACTC CTCATCTATG GTGCATCCAA CGTAGAATCT     180

GGGGTCCCTG CCAGGTTTAG TGGCAGTGGG TCTGGACAGA CTTCAGCCTC AACATCCATC     240

CTGTGGAGGA GGATGATATT GCAATGTATT TCTGTCAGCA AAGTAGGAAG GTTCCTTCGA     300

CGTTCGGTGG AGGCACCAAG CTGGAAATCA AA                                   332

(2) INFORMATION FOR SEQ ID NO:59:

(i) SEQUENCE CHARACTERISTICS:
            (A) LENGTH: 98 amino acids
            (B) TYPE: amino acid
            (C) STRANDEDNESS: single
            (D) TOPOLOGY: linear (xi) SEQUENCE DESCRIPTION: SEQ ID NO:59:

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
              35                  40                  45

Gly Glu Ile Asp Pro Ser Asp Ser Tyr Thr Tyr Tyr Asn Gln Lys Phe
         50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
              85                  90                  95

Ala Lys (2) INFORMATION FOR SEQ ID NO:60:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:60:

Gln Val Gln Leu Leu Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
              20                  25                  30

Trp Ile His Trp Val Lys Gln Arg Pro Gly Gln Gly Leu Glu Trp Ile
              35                  40                  45

Gly Glu Ile Asp Pro Ser Asp Asn Tyr Thr Tyr Tyr Asn Gln Lys Phe
         50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
              85                  90                  95

Ala Lys Gly Arg Leu Arg Tyr Phe Ala Met Asp Tyr Trp Gly Arg Gly
              100                 105                 110

Thr Ser Val Thr Val Ser Ser
         115

(2) INFORMATION FOR SEQ ID NO:61:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:61:

Gln Val Gln Leu Leu Glu Ser Gly Val Glu Leu Val Lys Pro Gly Ala
1               5                   10                  15

Ser Val Lys Leu Ser Cys Lys Ala Ser Gly Tyr Thr Phe Thr Ser Tyr
              20                  25                  30

Trp Met His Trp Val Lys Gln Lys Pro Gly Gln Gly Leu Glu Trp Ile
              35                  40                  45

Gly Glu Ile Asp Pro Ser Asp Ser Tyr Thr Tyr Tyr Asn Gln Lys Phe
         50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
              85                  90                  95

Ala Lys Gly Arg Leu Arg Tyr Phe Ala Met Asp Tyr Trp Gly Gln Gly

-continued (2) INFORMATION FOR SEQ ID NO:62:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:62:

```
Gln Val Gln Leu Leu Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Lys Gly Arg Leu Arg Tyr Phe Ala Met Asp Tyr Trp Gly Gln Gly
            100                 105                 110

Thr Ser Val Thr Val Ser Ser
            115
```

(2) INFORMATION FOR SEQ ID NO:63:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:63:

```
Gln Val Gln Leu Leu Glu Ser Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Val Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Lys Gly Arg Leu Arg Tyr Phe Ala Met Asp Tyr Trp Gly Gln Gly
            100                 105                 110

Thr Ser Val Thr Val Ser Ser
            115
```

(2) INFORMATION FOR SEQ ID NO:64:

(i) SEQUENCE CHARACTERISTICS:

(A) LENGTH: 98 amino acids
(B) TYPE: amino acid
(C) STRANDEDNESS: single
(D) TOPOLOGY: linear (xi) SEQUENCE DESCRIPTION: SEQ ID NO:64:

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg (2) INFORMATION FOR SEQ ID NO:65:

(i) SEQUENCE CHARACTERISTICS:
        (A) LENGTH: 121 amino acids
        (B) TYPE: amino acid
        (C) STRANDEDNESS: single
        (D) TOPOLOGY: linear (xi) SEQUENCE DESCRIPTION: SEQ ID NO:65:

Gln Val Gln Leu Leu Glu Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gln Ser Tyr Tyr Ser Tyr Tyr Ser Trp Phe Ala Tyr Trp Gly
            100                 105                 110

Gln Gly Thr Leu Val Thr Val Ser Thr
        115                 120

(2) INFORMATION FOR SEQ ID NO:66:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO:66:

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Gly Lys Gly Leu Glu Trp Leu
            35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg (2) INFORMATION FOR SEQ ID NO:67:

(i) SEQUENCE CHARACTERISTICS:
        (A) LENGTH: 121 amino acids
        (B) TYPE: amino acid
        (C) STRANDEDNESS: single
        (D) TOPOLOGY: linear (xi) SEQUENCE DESCRIPTION: SEQ ID NO:67:

Gln Val Gln Leu Leu Glu Ser Gly Pro Val Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Pro Gly Lys Gly Leu Glu Trp Leu
            35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys His Leu Pro Tyr Gly Asn Tyr Gly Tyr Tyr Ala Met Asp Tyr Trp
                100                 105                 110

Gly Gln Gly Thr Ser Val Thr Val Ser
            115                 120

(2) INFORMATION FOR SEQ ID NO:68:

(i) SEQUENCE CHARACTERISTICS:
        (A) LENGTH: 94 amino acids
        (B) TYPE: amino acid
        (C) STRANDEDNESS: single
        (D) TOPOLOGY: linear (xi) SEQUENCE DESCRIPTION: SEQ ID NO:68:

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr
                85                  90

(2) INFORMATION FOR SEQ ID NO:69:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:69:

```
Glu Leu Val Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Thr Gly Thr Lys Leu Glu Ile Lys
                100                 105
```

(2) INFORMATION FOR SEQ ID NO:70:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:70:

```
Glu Leu Val Met Thr Gln Ser Pro Val Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Thr Gly Thr Lys Leu Glu Ile Lys
                100                 105
```

(2) INFORMATION FOR SEQ ID NO:71:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:71:

```
Glu Leu Val Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30
```

```
Leu Ala Trp Tyr Gln Gln Lys Gln Gly Lys Ser Pro Gln Leu Leu Val
        35                  40                  45

Tyr Asn Ala Lys Ile Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
65                   70                  75                  80

Glu Asp Phe Gly Ser Tyr Tyr Cys Gln His His Tyr Gly Thr Pro Phe
                85                  90                  95

Thr Phe Gly Thr Gly Thr Lys Leu Glu Ile Lys
                100                 105

(2) INFORMATION FOR SEQ ID NO:72:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:72:

Glu Leu Val Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
65                   70                  75                  80

Glu Asp Phe Gly Ser Tyr Tyr Cys Gln His His Tyr Gly Thr Pro Phe
                85                  90                  95

Thr Phe Gly Thr Gly Thr Lys Leu Glu Ile Lys
                100                 105

(2) INFORMATION FOR SEQ ID NO:73:

(i) SEQUENCE CHARACTERISTICS:
        (A) LENGTH: 95 amino acids
        (B) TYPE: amino acid
        (C) STRANDEDNESS: single
        (D) TOPOLOGY: linear (xi) SEQUENCE DESCRIPTION: SEQ ID NO:73:

Glu Asn Val Leu Thr Gln Ser Pro Ala Ile Met Ala Ala Ser Pro Gly
 1               5                  10                  15

Glu Lys Val Thr Met Thr Cys Ser Ala Ser Ser Ser Val Ser Ser Gly
                20                  25                  30

Asn Phe His Trp Tyr Gln Gln Lys Pro Gly Thr Ser Pro Lys Leu Trp
        35                  40                  45

Ile Tyr Arg Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
65                   70                  75                  80

Ala Glu Asp Ala Ala Thr Tyr Tyr Cys Gln Gln Trp Ser Gly Tyr
                85                  90                  95

(2) INFORMATION FOR SEQ ID NO:74:
```

(i) SEQUENCE CHARACTERISTICS:
    (A) LENGTH: 108 amino acids
    (B) TYPE: amino acid
    (C) STRANDEDNESS: single
    (D) TOPOLOGY: linear (xi) SEQUENCE DESCRIPTION: SEQ ID NO:74:

Glu Leu Val Met Thr Gln Ser Pro Ala Ile Met Ala Ala Ser Pro Gly
1               5                   10                  15

Glu Lys Val Thr Met Thr Cys Ser Ala Ser Ser Val Ser Ser Gly
                20                  25                  30

Asn Phe His Trp Tyr Gln Gln Lys Pro Gly Thr Ser Pro Lys Leu Trp
            35                  40                  45

Ile Tyr Arg Thr Ser Asn Leu Ala Ser Gly Val Pro Ala Arg Phe Ser
50                      55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Gly Tyr Pro
                85                  90                  95

Arg Thr Phe Gly Gly Gly Thr Lys Leu Glu Ile Lys
            100                 105

(2) INFORMATION FOR SEQ ID NO:75:

(i) SEQUENCE CHARACTERISTICS:
        (A) LENGTH: 98 amino acids
        (B) TYPE: amino acid
        (C) STRANDEDNESS: single
        (D) TOPOLOGY: linear (xi) SEQUENCE DESCRIPTION: SEQ ID NO:75:

Asp Ile Val Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro
            35                  40                  45

Lys Leu Leu Ile Tyr Ala Ala Ser Asn Val Glu Ser Gly Val Pro Ala
50                      55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val (2) INFORMATION FOR SEQ ID NO:76:

(i) SEQUENCE CHARACTERISTICS:
        (A) LENGTH: 111 amino acids
        (B) TYPE: amino acid
        (C) STRANDEDNESS: single
        (D) TOPOLOGY: linear (xi) SEQUENCE DESCRIPTION: SEQ ID NO:76:

Asp Ile Glu Leu Thr Gln Ser Pro Ala Ser Leu Ala Val Ser Leu Gly
1               5                   10                  15

Gln Ser Val Thr Ile Ser Cys Arg Ala Ser Glu Ser Val Glu Tyr Tyr
                20                  25                  30

Gly Thr Ser Leu Met Gln Trp Tyr Gln Gln Lys Pro Gly Gln Pro Pro

```
              35                  40                  45
Lys Leu Leu Ile Tyr Gly Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Thr Phe Gly Gly Gly Thr Lys Leu Glu Ile Lys
                100                 105                 110
```

(2) INFORMATION FOR SEQ ID NO:77:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..9
        (D) OTHER INFORMATION: /note= "Portion of the germline
            gene incorporated into the CDR3 construct"

(xi) SEQUENCE DESCRIPTION: SEQ ID NO:77:

TGTGCAAAG                                                9

(2) INFORMATION FOR SEQ ID NO:78:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 6..9
        (D) OTHER INFORMATION: /note= "Portion of the germline
            gene incorporated into the CDR3 construct"

(xi) SEQUENCE DESCRIPTION: SEQ ID NO:78:

CAACTGGGAC CAC                                    13

(2) INFORMATION FOR SEQ ID NO:79:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 4..9
        (D) OTHER INFORMATION: /note= "Portion of the germline
            gene incorporated into the CDR3 construct"

(xi) SEQUENCE DESCRIPTION: SEQ ID NO:79:

TACGGCTACC AC                                     12

(2) INFORMATION FOR SEQ ID NO:80:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
              (A) NAME/KEY: misc_feature
              (B) LOCATION: 4..12
              (D) OTHER INFORMATION: /note= "Portion of the germline
                    gene incorporated into the CDR3 construct"

(xi) SEQUENCE DESCRIPTION: SEQ ID NO:80:

GATTACTATG CT                                                               12

(2) INFORMATION FOR SEQ ID NO:81:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ix) FEATURE:
              (A) NAME/KEY: CDS
              (B) LOCATION: 1..30

(ix) FEATURE:
              (A) NAME/KEY: misc_feature
              (B) LOCATION: group(18, 26)
              (D) OTHER INFORMATION: /note= "Positions that have mutated
                    away from the putative germline gene"

(xi) SEQUENCE DESCRIPTION: SEQ ID NO:81:

TGT GCA AAG GGG AGG CTC CGT TAC TTT GCT                                     30
Cys Ala Lys Gly Arg Leu Arg Tyr Phe Ala
 1               5                  10

(2) INFORMATION FOR SEQ ID NO:82:

(i) SEQUENCE CHARACTERISTICS:
              (A) LENGTH: 10 amino acids
              (B) TYPE: amino acid
              (D) TOPOLOGY: linear (ii) MOLECULE TYPE: protein (xi) SEQUENCE DESCRIPTION: SEQ ID NO:82:

Cys Ala Lys Gly Arg Leu Arg Tyr Phe Ala
 1               5                  10

(2) INFORMATION FOR SEQ ID NO:83:

(i) SEQUENCE CHARACTERISTICS:
              (A) LENGTH: 9 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1..9
              (D) OTHER INFORMATION: /note= "Portion of the germline
                    gene incorporated into the CDR3 construct"

(xi) SEQUENCE DESCRIPTION: SEQ ID NO:83:

TGTGCCAAA                                                                    9

(2) INFORMATION FOR SEQ ID NO:84:

(i) SEQUENCE CHARACTERISTICS:
              (A) LENGTH: 14 base pairs
              (B) TYPE: nucleic acid
              (C) STRANDEDNESS: single
              (D) TOPOLOGY: linear

```
    (ix) FEATURE:
          (A) NAME/KEY: misc_feature
          (B) LOCATION: 4..11
          (D) OTHER INFORMATION: /note= "Portion of the germline
              gene incorporated into the CDR3 construct"

(xi) SEQUENCE DESCRIPTION: SEQ ID NO:84:

GTGCCTACTA TGGT                                                              14

(2) INFORMATION FOR SEQ ID NO:85:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 4..15
          (D) OTHER INFORMATION: /note= "Portion of the germline
              gene incorporated into the CDR3 construct"

(xi) SEQUENCE DESCRIPTION: SEQ ID NO:85:

TACTATGGTA ACTACCAC                                                          18

(2) INFORMATION FOR SEQ ID NO:86:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 4..9
          (D) OTHER INFORMATION: /note= "Portion of the gerline gene
              incorporated into the CDR3 construct"

(xi) SEQUENCE DESCRIPTION: SEQ ID NO:86:

GATTACTAT                                                                     9

(2) INFORMATION FOR SEQ ID NO:87:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ix) FEATURE:
          (A) NAME/KEY: CDS
          (B) LOCATION: 1..39

(ix) FEATURE:
          (A) NAME/KEY: misc_feature
          (B) LOCATION: group(10, 14, 15)
          (D) OTHER INFORMATION: /note= "Positions that have mutated
              away from the putative germline gene"

(xi) SEQUENCE DESCRIPTION: SEQ ID NO:87:

TGT GCC AAA CAT CTC CCT TAT GGT AAC TAC GGT TAC TAT                          39
Cys Ala Lys His Leu Pro Tyr Gly Asn Tyr Gly Tyr Tyr
                15                  20

(2) INFORMATION FOR SEQ ID NO:88:

(i) SEQUENCE CHARACTERISTICS:
          (A) LENGTH: 13 amino acids
          (B) TYPE: amino acid
```

(D) TOPOLOGY: linear (ii) MOLECULE TYPE: protein (xi) SEQUENCE DESCRIPTION: SEQ ID NO:88:

Cys Ala Lys His Leu Pro Tyr Gly Asn Tyr Gly Tyr Tyr
 1               5                  10

(2) INFORMATION FOR SEQ ID NO:89:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..9
        (D) OTHER INFORMATION: /note= "Portion of the germline
            gene incorporated into the CDR3 construct"

(xi) SEQUENCE DESCRIPTION: SEQ ID NO:89:

TGTGCAAGA                                                              9

(2) INFORMATION FOR SEQ ID NO:90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 4..20
        (D) OTHER INFORMATION: /note= "Portion of the germline
            gene incorporated into the CDR3 construct"

(xi) SEQUENCE DESCRIPTION: SEQ ID NO:90:

GTGCCTACTA TGGTAACTAC CAC                                             23

(2) INFORMATION FOR SEQ ID NO:91:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 5..12
        (D) OTHER INFORMATION: /note= "Portion of the germline
            gene incorporated into the CDR3 construct"

(xi) SEQUENCE DESCRIPTION: SEQ ID NO:91:

TGTGCCTGGT TT                                                         12

(2) INFORMATION FOR SEQ ID NO:92:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..39

```
    (ix) FEATURE:
          (A) NAME/KEY: misc_feature
          (B) LOCATION: group(22, 25)
          (D) OTHER INFORMATION: /note= "Positions that have mutated
              away from the putative germline gene"

(xi) SEQUENCE DESCRIPTION: SEQ ID NO:92:

TGT GCA AGA CAG TCC TAC TAT AGT TAC TAC TCC TGG TTT                    39
Cys Ala Arg Gln Ser Tyr Tyr Ser Tyr Tyr Ser Trp Phe
 15                  20                  25

(2) INFORMATION FOR SEQ ID NO:93:

(i) SEQUENCE CHARACTERISTICS:
          (A) LENGTH: 13 amino acids
          (B) TYPE: amino acid
          (D) TOPOLOGY: linear (ii) MOLECULE TYPE: protein (xi) SEQUENCE DESCRIPTION: SEQ ID NO:93:

Cys Ala Arg Gln Ser Tyr Tyr Ser Tyr Tyr Ser Trp Phe
  1               5                  10

(2) INFORMATION FOR SEQ ID NO:94:

(i) SEQUENCE CHARACTERISTICS:
          (A) LENGTH: 8 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 1..8
          (D) OTHER INFORMATION: /note= "Portion of the germline
              gene incorporated into the CDR3 construct"

(xi) SEQUENCE DESCRIPTION: SEQ ID NO:94:

GGTTACCC                                                                8

(2) INFORMATION FOR SEQ ID NO:95:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ix) FEATURE:
          (A) NAME/KEY: misc_feature
          (B) LOCATION: 8..20
          (D) OTHER INFORMATION: /note= "Portion of the germline
              gene incorporated into the CDR3 construct"

(xi) SEQUENCE DESCRIPTION: SEQ ID NO:95:

CACTGTGGTG GACGTTCGGT                                                  20

(2) INFORMATION FOR SEQ ID NO:96:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ix) FEATURE:
          (A) NAME/KEY: CDS
          (B) LOCATION: 1..21

(ix) FEATURE:
```

```
            (A) NAME/KEY: misc_feature
            (B) LOCATION: group(9, 10)
            (D) OTHER INFORMATION: /note= "Positions that have mutated
                away from the putative germline gene"

(xi) SEQUENCE DESCRIPTION: SEQ ID NO:96:

GGT TAC CCA CGG ACG TTC GGT                                              21
Gly Tyr Pro Arg Thr Phe Gly
    15                  20

(2) INFORMATION FOR SEQ ID NO:97:

(i) SEQUENCE CHARACTERISTICS:
            (A) LENGTH: 7 amino acids
            (B) TYPE: amino acid
            (D) TOPOLOGY: linear (ii) MOLECULE TYPE: protein (xi) SEQUENCE DESCRIPTION: SEQ ID NO:97:

Gly Tyr Pro Arg Thr Phe Gly
  1               5

(2) INFORMATION FOR SEQ ID NO:98:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..8
            (D) OTHER INFORMATION: /note= "Portion of the germline
                gene incorporated into the CDR3 construct"

(xi) SEQUENCE DESCRIPTION: SEQ ID NO:98:

GGTACTCC                                                                  8

(2) INFORMATION FOR SEQ ID NO:99:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 8..20
            (D) OTHER INFORMATION: /note= "Portion of the germline
                gene incorporated into the CDR3 construct"

(xi) SEQUENCE DESCRIPTION: SEQ ID NO:99:

TGATTCACGT TCGGC                                                         15

(2) INFORMATION FOR SEQ ID NO:100:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 1..21

(xi) SEQUENCE DESCRIPTION: SEQ ID NO:100:
```

```
GGT ACT CCA TTC ACG TTC GGC                                              21
Gly Thr Pro Phe Thr Phe Gly
         10

(2) INFORMATION FOR SEQ ID NO:101:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:101:

Gly Thr Pro Phe Thr Phe Gly
  1               5

(2) INFORMATION FOR SEQ ID NO:102:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..8
        (D) OTHER INFORMATION: /note= "Portion of the germline
              gene incorporated into the CDR3 construct"

(xi) SEQUENCE DESCRIPTION: SEQ ID NO:102:

AAGGTTCC                                                                  8

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 8..20
        (D) OTHER INFORMATION: /note= "Portion of the germline
              gene incorporated into the CDR3 construct"

(xi) SEQUENCE DESCRIPTION: SEQ ID NO:103:

CACTGTGGTG GACGTTCGGT                                                    20

(2) INFORMATION FOR SEQ ID NO:104:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..21

(ix) FEATURE:
        (A) NAME/KEY: misc_feature
        (B) LOCATION: group(9, 11)
        (D) OTHER INFORMATION: /note= "Positions that have mutated
              away from the putative germline gene"

(xi) SEQUENCE DESCRIPTION: SEQ ID NO:104:

AAG GTT CCT TCG ACG TTC GGT                                              21
```

```
Lys Val Pro Ser Thr Phe Gly
  1               5
```

(2) INFORMATION FOR SEQ ID NO:105:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:105:

```
Lys Val Pro Ser Thr Phe Gly
  1               5
```

(2) INFORMATION FOR SEQ ID NO:106:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:106:

GTGCCAGATG TGAGCTCGTG ATGACCCAGT CTCCA                        35

(2) INFORMATION FOR SEQ ID NO:107:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:107:

TCCTTCTAGA TTACTAACAC TCTCCCCTGT TGAA                         34

(2) INFORMATION FOR SEQ ID NO:108:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:108:

GATATCACTA GTGGGCCCGC TGGGCTC                                27

(2) INFORMATION FOR SEQ ID NO:109:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:109:

TGGGCAACTA GTACCTGGGG GGGTACTGGG CTTGG                        35

(2) INFORMATION FOR SEQ ID NO:110:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (xi) SEQUENCE DESCRIPTION: SEQ ID NO:110:

AGGTCCAGCT KCTCGAGTCW GG 22

(2) INFORMATION FOR SEQ ID NO:111:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:111:

Gly Gly Gly Gly Ser Gly Gly Gly Gly Ser Gly Gly Gly Gly Ser
1               5                   10                  15

(2) INFORMATION FOR SEQ ID NO:112:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:112:

Gly Ala Pro Val Pro Tyr Pro Asp Pro Leu Glu Pro Arg
1               5                   10

(2) INFORMATION FOR SEQ ID NO:113:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:113:

Met Lys Lys Leu Leu Phe Ala Ile Pro Leu Val Val Pro Phe Tyr Ala
1               5                   10                  15

Ala Gln Pro Ala
            20